US008247423B2

(12) United States Patent
Estok et al.

(10) Patent No.: US 8,247,423 B2
(45) Date of Patent: Aug. 21, 2012

(54) METHODS AND COMPOSITIONS FOR THE TREATMENT OF CANCER, TUMORS, AND TUMOR-RELATED DISORDERS

(75) Inventors: Thomas M. Estok, Carlsbad, CA (US); Sara L. Zaknoen, Carlsbad, CA (US); Robert K. Mansfield, Carlsbad, CA (US); Tracy Lawhon, Encinitas, CA (US)

(73) Assignee: Tragara Pharmaceuticals, Inc., San Diego, CA (US)

( * ) Notice: Subject to any disclaimer, the term of this patent is extended or adjusted under 35 U.S.C. 154(b) by 720 days.

(21) Appl. No.: 12/172,202

(22) Filed: Jul. 11, 2008

(65) Prior Publication Data

US 2009/0017024 A1    Jan. 15, 2009

Related U.S. Application Data

(60) Provisional application No. 60/949,483, filed on Jul. 12, 2007, provisional application No. 60/990,900, filed on Nov. 28, 2007, provisional application No. 61/044,425, filed on Apr. 11, 2008.

(51) Int. Cl.
*A01N 43/54* (2006.01)
*A01N 43/00* (2006.01)
*A01N 43/36* (2006.01)
*A61K 31/517* (2006.01)
*A61K 31/535* (2006.01)
*A61K 31/33* (2006.01)
*A61K 31/40* (2006.01)
*C07D 239/72* (2006.01)

(52) U.S. Cl. ............... 514/266.4; 514/234.5; 514/183; 514/427; 544/283

(58) Field of Classification Search ............ 514/234.5, 514/266.4, 427, 183; 544/283
See application file for complete search history.

(56) References Cited

U.S. PATENT DOCUMENTS

| | | |
|---|---|---|
| 3,168,531 A | 2/1965 | Short |
| 3,168,532 A | 2/1965 | Short |
| 3,285,931 A | 11/1966 | Huisgen |
| 3,427,305 A | 2/1969 | Chinn et al. |
| 3,536,809 A | 10/1970 | Applezweig |
| 3,551,571 A | 12/1970 | Pachter et al. |
| 3,598,123 A | 8/1971 | Zaffaroni |
| 3,644,399 A | 2/1972 | Brown et al. |
| 3,714,232 A | 1/1973 | Sarett et al. |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,010,273 A | 3/1977 | Bormann et al. |
| 4,161,531 A | 7/1979 | Bormann et al. |
| 4,176,190 A | 11/1979 | Habicht |
| 4,328,245 A | 5/1982 | Yu et al. |
| 4,409,239 A | 10/1983 | Yu |
| 4,410,545 A | 10/1983 | Yu et al. |
| 4,560,769 A | 12/1985 | Menig et al. |
| 4,694,018 A | 9/1987 | Chinn |
| 4,792,568 A | 12/1988 | Auerbach |
| 4,906,758 A | 3/1990 | Hoelderich et al. |
| 4,962,119 A | 10/1990 | Boschelli et al. |
| 4,992,462 A | 2/1991 | Hubsch et al. |
| 5,010,098 A | 4/1991 | Brown et al. |
| 5,059,595 A | 10/1991 | LeGrazie |
| 5,073,543 A | 12/1991 | Marshall et al. |
| 5,096,919 A | 3/1992 | Wasley et al. |
| 5,112,848 A | 5/1992 | Brooks et al. |
| 5,120,548 A | 6/1992 | McClelland et al. |
| 5,128,485 A | 7/1992 | Kameswaran |
| 5,144,041 A | 9/1992 | Doehner et al. |
| 5,208,018 A | 5/1993 | Gough |
| 5,210,218 A | 5/1993 | Kagabu et al. |
| 5,236,943 A | 8/1993 | Heitsch et al. |
| 5,254,713 A | 10/1993 | Kagabu et al. |
| 5,310,938 A | 5/1994 | Brown et al. |
| 5,317,019 A | 5/1994 | Bender et al. |
| 5,344,991 A | 9/1994 | Reitz et al. |
| 5,354,556 A | 10/1994 | Sparks et al. |
| 5,380,738 A | 1/1995 | Norman et al. |
| 5,418,254 A | 5/1995 | Huang et al. |
| 5,434,178 A | 7/1995 | Talley et al. |
| 5,455,263 A | 10/1995 | Doscher et al. |
| 5,466,823 A | 11/1995 | Talley et al. |
| 5,474,995 A | 12/1995 | Ducharme et al. |
| 5,486,534 A | 1/1996 | Lee et al. |
| 5,496,845 A | 3/1996 | Martin et al. |
| 5,502,051 A | 3/1996 | Scharfenberg et al. |
| 5,521,207 A | 5/1996 | Graneto |
| 5,521,213 A | 5/1996 | Prasit et al. |
| 5,536,752 A | 7/1996 | Ducharme et al. |

(Continued)

FOREIGN PATENT DOCUMENTS

CA     2180624     1/1997

(Continued)

OTHER PUBLICATIONS

Vippagunta et al. Advanced Drug Delivery Reviews, 2001, vol. 48, pp. 3-26.*
Collins et al. American Family Physician, Jan. 2007, vol. 75, Iss. 1, pp. 56-63.*
Anonymous, "Bevacizumab and gemcitabine combined with either cetuximab or erlotinib in treating patients with advanced pancreatic cancer," Clinical Trials Dec. 1, 2006, http://www.clinicaltrials.gov/ct/gui/show/NCT00091026.
Burris, "Dual kinase inhibition in the treatment of breast cancer: Initial experience with the EDGR/ErbB-2 inhibitor lapatinib," The Oncologist 9(Suppl 3):10-15 (2004).
Hanai et al., "Studies on the antitumor activities of CS-706 (R-109339), a novel COX-2 inhibitor: Influence of the administration schedule and combination effects with cisplatin," Proceedings of Annual Meeting of American Association for Cancer Research 44:919-920 (2003).

(Continued)

*Primary Examiner* — Samira Jean-Louis
(74) *Attorney, Agent, or Firm* — Wilson, Sonsini, Goodrich & Rosati

(57) ABSTRACT

Described herein are compositions and methods for using these compositions in the treatment of cancer, tumors, and tumor-related disorders in a subject.

24 Claims, 3 Drawing Sheets

U.S. PATENT DOCUMENTS

| | | | |
|---|---|---|---|
| 5,550,142 A | 8/1996 | Ducharme et al. |
| 5,583,148 A | 12/1996 | Anderson et al. |
| 5,591,767 A | 1/1997 | Mohr et al. |
| 5,593,991 A | 1/1997 | Adams et al. |
| 5,612,059 A | 3/1997 | Cardinal et al. |
| 5,616,601 A | 4/1997 | Khanna et al. |
| 5,620,999 A | 4/1997 | Weier et al. |
| 5,633,272 A | 5/1997 | Talley et al. |
| 5,639,476 A | 6/1997 | Oshlack et al. |
| 5,639,480 A | 6/1997 | Bodmer et al. |
| 5,643,933 A | 7/1997 | Talley et al. |
| 5,663,195 A | 9/1997 | Scolnick |
| 5,674,533 A | 10/1997 | Santus et al. |
| 5,698,220 A | 12/1997 | Cardinal et al. |
| 5,700,816 A | 12/1997 | Isakson et al. |
| 5,709,874 A | 1/1998 | Hanson et al. |
| 5,710,140 A | 1/1998 | Ducharme et al. |
| 5,733,566 A | 3/1998 | Lewis |
| 5,739,108 A | 4/1998 | Mitchell |
| 5,747,498 A | 5/1998 | Schnur et al. |
| 5,759,542 A | 6/1998 | Gurewich |
| 5,792,778 A | 8/1998 | De Laszlo et al. |
| 5,798,119 A | 8/1998 | Herbig et al. |
| 5,840,674 A | 11/1998 | Yatvin et al. |
| 5,891,474 A | 4/1999 | Busetti et al. |
| 5,900,252 A | 5/1999 | Calanchi et al. |
| 5,908,858 A | 6/1999 | Kimura et al. |
| 5,922,356 A | 7/1999 | Koseki et al. |
| 5,928,635 A | 7/1999 | Schmidt |
| 5,932,598 A | 8/1999 | Talley et al. |
| 5,935,990 A | 8/1999 | Khanna et al. |
| 5,972,366 A | 10/1999 | Haynes et al. |
| 5,972,891 A | 10/1999 | Kamei et al. |
| 5,972,986 A | 10/1999 | Seibert et al. |
| 5,980,945 A | 11/1999 | Ruiz |
| 5,985,307 A | 11/1999 | Hanson et al. |
| 5,990,148 A | 11/1999 | Isakson et al. |
| 5,993,855 A | 11/1999 | Yoshimoto et al. |
| 6,004,534 A | 12/1999 | Langer et al. |
| 6,025,353 A | 2/2000 | Masferrer et al. |
| 6,039,975 A | 3/2000 | Shah et al. |
| 6,042,620 A | 3/2000 | Braun et al. |
| 6,045,773 A | 4/2000 | Isakson et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,110,948 A | 8/2000 | Momose et al. |
| 6,113,943 A | 9/2000 | Okada et al. |
| 6,114,359 A | 9/2000 | Elliott |
| 6,120,751 A | 9/2000 | Unger |
| 6,131,570 A | 10/2000 | Schuster et al. |
| 6,136,839 A | 10/2000 | Isakson et al. |
| 6,139,865 A | 10/2000 | Friend et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,264,970 B1 | 7/2001 | Hata et al. |
| 6,267,981 B1 | 7/2001 | Okamoto et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,350,458 B1 | 2/2002 | Modi |
| 6,376,461 B1 | 4/2002 | Igari et al. |
| 6,403,630 B1 | 6/2002 | Dannenberg et al. |
| 6,407,244 B1 | 6/2002 | Murthy et al. |
| 6,419,961 B1 | 7/2002 | Igari et al. |
| 6,469,040 B2 | 10/2002 | Seibert et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,887,893 B1* | 5/2005 | Kurakata et al. ............... 514/427 |
| 6,900,221 B1 | 5/2005 | Norris et al. |
| RE39,420 E | 12/2006 | Kimura et al. |
| 7,411,095 B2 | 8/2008 | Okazaki |
| 7,745,481 B2 | 6/2010 | Kutakta |
| 2003/0100605 A1 | 5/2003 | Grupp et al. |
| 2004/0082557 A1 | 4/2004 | Wajszczuk et al. |
| 2004/0127470 A1 | 7/2004 | Masferrer |
| 2005/0004109 A1 | 1/2005 | Kurakata |
| 2005/0014814 A1 | 1/2005 | Kurakata et al. |
| 2005/0187278 A1 | 8/2005 | Taylor |
| 2005/0272755 A1* | 12/2005 | Denis et al. .................. 514/283 |
| 2006/0094012 A1 | 5/2006 | Lenz et al. |
| 2006/0135490 A1 | 6/2006 | Fitzgerald et al. |
| 2006/0154941 A1 | 7/2006 | Huang |
| 2007/0015787 A1 | 1/2007 | Bruncko et al. |
| 2007/0092940 A1 | 4/2007 | Eigenbrot et al. |
| 2007/0100148 A1 | 5/2007 | Murki et al. |
| 2007/0112202 A1 | 5/2007 | Friedman et al. |
| 2008/0166358 A1* | 7/2008 | Tung ....................... 424/158.1 |
| 2009/0163428 A1 | 6/2009 | Chiu et al. |
| 2009/0258886 A1 | 10/2009 | Blanchard et al. |

FOREIGN PATENT DOCUMENTS

| | | |
|---|---|---|
| DE | 1938904 | 2/1970 |
| EP | 0038536 | 10/1981 |
| EP | 0303206 | 2/1989 |
| EP | 0530147 | 3/1993 |
| EP | 0745596 A | 12/1996 |
| EP | 0799823 | 10/1997 |
| EP | 0688723 B1 | 7/1998 |
| EP | 0863134 A | 9/1998 |
| EP | 0927555 A1 | 7/1999 |
| EP | 0949793 A | 10/1999 |
| FR | 1356901 | 7/1964 |
| FR | 2054474 | 4/1971 |
| GB | 1271082 | 4/1972 |
| JP | 2-240058 | 9/1990 |
| JP | 3-141261 | 6/1991 |
| JP | Kokai 5-163293 | 12/1991 |
| JP | 5001027 | 5/1993 |
| WO | WO-92-10190 | 6/1992 |
| WO | WO-92-10498 | 6/1992 |
| WO | WO-94-13635 | 6/1994 |
| WO | WO-94-15932 | 7/1994 |
| WO | WO-94-27980 | 12/1994 |
| WO | WO-95-00501 | 1/1995 |
| WO | WO -95-02600 | 1/1995 |
| WO | WO-95-11883 | 5/1995 |
| WO | WO-95-15316 | 6/1995 |
| WO | WO-95-18799 | 7/1995 |
| WO | WO-95-30656 | 11/1995 |
| WO | WO-95-32194 | 11/1995 |
| WO | WO-96-03385 | 2/1996 |
| WO | WO-96-03387 | 2/1996 |
| WO | WO-96-03388 | 2/1996 |
| WO | WO-96-03392 | 2/1996 |
| WO | WO-96-19463 | 6/1996 |
| WO | WO-96-25405 | 8/1996 |
| WO | WO-96-36617 | 11/1996 |
| WO | WO-96-38418 | 12/1996 |
| WO | WO-97-13755 | 4/1997 |
| WO | WO-97-27181 | 7/1997 |
| WO | WO 97/36497 | 10/1997 |
| WO | WO-97-38986 | 10/1997 |
| WO | WO-98-06708 | 2/1998 |
| WO | WO-98-16227 | 4/1998 |
| WO | WO-98-22101 | 5/1998 |
| WO | WO-98-25896 | 6/1998 |
| WO | WO 99/18960 | 4/1999 |
| WO | WO-00-38716 A1 | 7/2000 |
| WO | WO-02-02552 A1 | 1/2002 |
| WO | WO 02/17918 | 3/2002 |
| WO | WO-02-20020 A1 | 3/2002 |
| WO | WO-2004-093868 A1 | 11/2004 |
| WO | WO-2005-020895 A2 | 3/2005 |
| WO | WO-2005-020926 A2 | 3/2005 |
| WO | WO 2005/037259 | 4/2005 |
| WO | WO-2005-048979 A2 | 6/2005 |
| WO | WO-2005-102358 A2 | 11/2005 |
| WO | WO 2006-124113 A | 11/2006 |
| WO | WO-2009-009778 A1 | 1/2009 |
| WO | WO-2009-042618 | 4/2009 |

OTHER PUBLICATIONS

Jani et al., "CP-724714, a novel erbB2 receptor tyrosine kinase inhibitor for cancer therapy," Proceedings of the Annual Meeting of the American Association for Cancer Research 45:1071 (2004).
Kiguchi et al., "Therapeutic effect of CS-706, a specific cyclooxygenase-2 inhibitor, on gallbladder carcinoma in BK5. ErbB-2 mice," Mol Cancer Ther 6(6):1709-1717 (2007).
Rabindran, "Antitumor activity of HER-2 inhibitors," Cancer Letters 227:9-23 (2005).
Tiseo et al., "Epidermal growth factor receptor inhibitors: a new prospective in the treatment of lung cancer," Curr Med Chem, Anti-Cancer Agents 4(2):139-148 (2004).
Zaknoen et al., "Activity of TGO1, a selective COX-2 inhibitor, alone and in combination with standard agents in humna breast carcinoma xenografts," Proceedings o fhte Annual Meeting of the American Association for Cancer Research 49:1345 (2008).
EP08826106.0 Supplementary Search Report mailed Oct. 20, 2010.
EP08834280.3 Supplementary Search Report and Written Opinion mailed Dec. 1, 2010.
EP08834597.0 Supplementary Search Report and Written Opinion mailed Dec. 1, 2010.
EP08833936.1 Supplementary Search Report and Written Opinion mailed Dec. 1, 2010.
PCT/US11/23810 Search Report and Written Opinion mailed Feb. 4, 2011.
PCT/US08/84586 Search Report dated Feb. 18, 2009.
Argiles et al., "The Metabolic Basis of Cancer Cachexia," Medicinal Res. Rev. 17(5):477-498 (1997).
Breuille et al., "A Sustained Rat Model for Studying the Long-Lasting Catabolic State of Sepsis," Infection and Immunity 67(3):1079-1085 (1999).
Cunningham et al., "Final results of a randomized trial comparing "Tomudex" (raltitrexed) with 5-fluorouracil plus leucovorin in advanced colorectal cancer," Annals of Oncology 7:961-965 (1996).
Damas et al., "Inhibition De L'Action Hypotensive De L'Acide Arachidonique Chez Le Rat," J. Pharmacol. (Paris):9(1):13-23 (1978).
Denny et al., "Phenyl Ester of Lactic Acid," J. Med. Chem. 11(2):403-404 (1968).
DeWitt et al., "Yes, but Do They Still Get Headaches?" Cell 83:345-348 (1995).
Elder et al., "Induction of Aopototic Cell Death in Human Colorectal Carcinoma Cell Lines by a Cyclooxygeanse-2 (COS)-2)-selective Nonsteroidal Anti-Inflammatory Drug: Independence from COX-2 Protein Expression," Clin. Cancer Res. 3:1679-1683 (1997).
Ferrari et al., "Estimation of the in vivo effect of cyclooxygenase inhibitors on protaglandin E2 levels in mouse brain," Eur. J. Pharmacol. 179:25-34 (1990).
Futaka et al., "NS-398, A new anti-infllamtory agent, selectively inhibits prostaglandin G/H synthase/cyclooxygenase (COX-2) activity in vitro," Prostaglandins 47:55-59 (1994).
Hida et al., Cyclooxygenase-2 Inhibitor Induces Aopotosis and Enhances Cytotoxicity of Various Anticancer Agents in Non-Small Cell Lung Cancer Cell Lines, Clin. Cancer Res. 6:2006-2011 (2000).
Hla et al., "Role of the early response gene cyclooxygenase (COX)-2 in angiogenesis, Molecular, Cellular, and Clinical Aspects of Angiogensis," M.E. Maragoudakis, ed., Plenum Press, Nato ASI Series, Series A: Life Series, vol. 285:191-198 (1966).
Huang et al., "Cyclooxygenase and 5-lipoxygenase inhibitors for the prevention and treatment of cancer,Oncologic, Endocrine and Metabolic Monthly Update,", Exp. Op. ;Invest. Drugs 4(3):243-249 (1995).
Katori, "Solid tumor, plasma exudation arachidonic acid metabolism," Igaku no Ayumi 175(8):527-531 (1995).
Katritzky et al., "A—CH2CH:C+NR2 Synthon: Novel Preparations of 1,3-disubstituted Allylamines and of 1,2-diaryl Pyrroles," Tetrahedron Lett. 36(3):343-346 (1995).
Kesari et al., "Phase II study of metronomic chemotherapy for recurrent malignant gliomas in adults," Neuro-Oncology 9:354-363 (2007).
Khanna et al., 1,2-Diarylimidazoles as Potent, Cyclooxygenase-2 Selective, and Orally Active Antiinflammatory Agents,"J. Med. Chem 40:1634-1647 (1997)".

Khanna et al., "1,2-Diarylpyrroles as Potent and Selective Inhibitors of Cyclooxygenase-2," J. Med. Chem. 40:1619-1633 (1997).
Konturek et al., "Distribution of prostaglandins in gastric and duodenal mucosa of healthy subjects and duodenal ulcer patients: effects of aspirin and paracetamol," Gut 22:283-289 (1981).
Lala et al., Effects of chronic indomethacin therapy on the development and progression of spontaneous mammary tumors in C3H/HEJ mice, Int. J. Cancer 73:371-380 (1997).
Lehmann et al., "Meloxicam: A Toxicology Overview," Inflammopharmacology 4:105-123 (1996).
Li et al., "1,2-Diarylcyclopentenes as selective cyclooxygenase-2 inhibitors and orally active anti-inflammatory agents," J. Med. Chem. 38(22):4570-4578 (1995).
Li et al., "Synthesis and properties of 1-aryl-3-benzoyl-2-,5-diphenylpyrroles," Chemical Abstracts, vol. 105(17):677, Oct. 27, 1986, Columbus, Ohio, abstract No. 152868p.
Li et al., "Synthesis and properties of polysubstituted pyrroles (II)," Chemical Abstract vol. 104 (15):684 Apr. 14, 1986, Columbus, Ohio, abstract No. 129728p.
Malmberg et al., "Capsaicin-evoked prostaglandin E2 release in spinal cord slices: relative effect of cyclooxygenase inhibitors," Eur. J. Pharmacol. 271:293-299 (1994).
Masferrer et al., "Selective inhibition of inducible cyclooxygenase 2 in vivo is antiinflammatory and nonulcerogenic," PNAS USA 91:3228-3232 (1994).
Mattammal et al., "Mechanism of Inhibition of Renal Prostaglandin Production by Acetaminophen," J. Pharmacol. Exp. Ther. 210:405-409 (1979).
McCarthy, "Inhibitors of Prostaglandin Synthesis Do Not Improve Food Intake of Body Weight of Tumor-Bearing Rats," Research in Nursing and Health, 1999, pp. 380-387, vol. 22.
Misset et al., "Phase 1 and pharmacokinetic study of the multitargeted antifolate pemetrexed in combination with oxaliplatin in patients with advanced solid tumors," Annals of Onocology 15:1123-1129 (2004).
Mori et al., "Purification of a Lipoprotein Lipase-Inhibiting Protein Produced by a Melanoma Cell Line Associated with Cancer Cachexia," Biochem. Biophys. Res. Comm. 160(3):1085-1092 (1989).
Nakanishi et al., Inhibitors of cyclooxygenase-2 (COX-2) suppressed the proliferation and differentiation of human leukaemia cell lines, Eur. J. Cancer 37:1570-1578 (2001).
Oshima et al., Suppression of intestinal polyposis in Apx 716 knockout mice by inhibition of cylcooxygenase 2 (COX-2),: Cell 87:803-809 (1996).
Parrett et al., "Cyclooxygenase-2 gene expression in human breast cancer," Int. J. Oncol. 10:503-507 (1997).
Pitot et al., "Facts and Theories Concerning Mechanisms of Carcinogenesis,"FASEB J. 5:2280-2286 (1991).
Pold et al., "Cyclooxygenase-2 Modulates the Insulin-Like Growth Factor Axis in Non-Small-Cell Lung Cancer," Cancer Res. 64:6549-6555 (2004).
Poortmans et al., "High-Dose Methotrexate-Based Chemotherapy Followed by Consolidating Radiotherapy in Non-AIDS-Related Primary Central Nervous System Lymphoma: European Organization for Research and Treatment of Cancer Lymphoma Group Phase II Trial 20962," J. Clin. Onc. 21:4483-4488 (2003).
Porretta et al., "Ricerch su sostanze ad attivita antibatterica ed antifungina," Farmaco 44(1):65-76 (1989).
PCT/US08/69892 Search Report dated Dec. 12, 2008.
PCT/US08/77042 Search Report dated Mar. 3, 2009.
PCT/US08/77410 Search Report dated Feb. 12, 2009.
PCT/US08/84588 Search Report dated Mar. 4, 2009.
PCT/US08/77401 Search Report dated Feb. 13, 2009.
Rao et al., "Differential Activity of Aspirin, Ketoprofen, and Sulindac as Cancer Chemopreventive Agents in the Mouse Urinary Bladder," Carcinogenisis 17:1435-1438 (1996).
Reddy et al., "Evaluation of Cyclooxygenase-2 Inhibitor for Potential Chemopreventive Properties in Colon Carcinogenesis," Cancer Res. 56:4566-4569 (1996).

Rioux et al., "Recovery from 4-(MethylInitrosamino)-1-(3-pyridyl)-1-butanone-Induced Immunosuppression in A/J Mice by Treatment with Nonsteroidal Anti-inflammatory Drugs," J. National Cancer Instutute 89(12):874-880 (1997).

Ristimaki et al., "Expression of cyclooxygenase-2 in human gastric carcinoma," Cancer Res. 57(7):1276-1280 (1997).

Ruff et al., "Inhibitors of Prostaglandin Synthesis or Cathepsin B Prevent Muscle Wasting Due to Sepsis in the Rat,"J. Clin. Investigat. 73:1483-1486 (1984).

Shaffer et al., "Attenuation by Acetaminophen o fArachidonic Acid-Induced Coronary Vasodilation and Output of Prostaglandins in the Isolated Rat Heart," Eur. J. Pharmacol. 72:57-61 (1981).

Sheng et al., "Inhibition of Human Colon Cancer Cell Growth by Selective Inhibition of Cyclooxygenase-2," J. Clin. Investig. 99(9):2254-2259 (1997).

Sheng et al., A Selective Cyclooxygenase 2 Inhibitor Suppresses the Growth of H-ras-Transformed Rat Intestinal Epithelial Cells, Gastroenterology 113(6):1883-1891 (1997).

Singh et al., Methotrexate Induced Differentiation in Colon Cancer Cells is Primarily Due to Purine Deprivation, J. Cell. Biochem. 99:146-155 (2006).

Strassmann et al., "Inhibition of experimental cancer cachexia by anti-cytokine and anti-cytokine-receptor therapy," Cytokines and Molecular Therapy 1:107-113 (1995).

Strelkov et al., "Effects of systemic inhibition of prostaglandin production on protein metabolism in tumor-bearing rats," Am. J. Physiol. 257:C261-67 (1989).

Takahashi et al., "Suppression of azoxymethane-induced aberrant crypt foci in rat colon by nimesulide, a selective Inhibitor of cyclooxygenase 2," J. Cancer Res. Clin. Oncol. 122:219-222 (1996).

Tanaka et al., "T-614, A novel antirheumatic drug, inhibits both the activity and induction of cyclooxygenase-2 (COX-2) in cultured fibroblasts," Japanese J. Pharmacology 67(4):305-314 (1995).

Teicher et al., "Cyclooxygenase and lipoxygenase inhibitors as modulators of cancer therapies," Cancer Chemother. Pharmacol. 33:515-522 (1994).

Thiault et al., "Derives N-Aryl Pyrroliques a Acativite Analgesique Et Anti-Inflammatoire," Farmaco [Sci] vol. 39(6):524-537 (1984).

Tracey et al., "Anti-cachectin/TNF monoclonal antibodies prevent septic shock during letahl bacteraemia," Nature 330:662-664 (1987).

Tsujii et al., "Cyclooxygenase-2 expression in human colon cancer cells increases metastatic potential," PNAS USA 94(7):B9533, 36-40 Abstract, Medline (on-line) Department of Medicine USA, No. 97250538 (1997).

Tsujii et al., "Alterations in Cellular Adhesion and Apoptosis in Epithelial Cells Overexpressing Prostaglandin Endoperoxide Synthase 2," Cell 83:493-501 (1995).

Wallerstein et al., "The Return of Antimetabolite Sensistivity in Methotrexate- and 6-Mercaptopurine-resistant L1210 Murine Leukemia by the Process of Adaptive Selection," Cancer Res. 32:2235-2240 (1972).

Wilkerson et al., "Antiinflammatory 4,5-Diarylpyrroles: Synthesis and QSAR," J. Med. Chem. 37(7):988-998 (1994).

Wu, "Cyclooxygenase 2 Induction: Moleular mechanism and pathophysiologic roles," J. Lab. Clin. Med. 128(3):242-245 (1996).

Xu, "COX-2 inhibitors in cancer treatment and prevention, a recent development," Anti-Cancer Drugs 13:127-137 (2002).

Yoshimi et al., "Inhibitory Effect of NS-398, a Selective Cyclooxygenase-2 Inhibitor, on Azoxymethane-induced Aberrant Crypt Foci in Colon Carcinogenesis of F344 Rats," Jpn. J. Cancer Res. 88:1044-1051 (1997).

Zenser et al., "Effect of Acetaminophen on Prostaglandin E2 and Prostaglandin F21 Synthesis in the Renal Inner Medulla of Rat," Biochim. Biophys. Acta 542:486-495 (1978).

Anonymous, "Statement on a nonproprietary name adopted by the USAN Council," AMA retrieved Jul. 2, 2010, http://www.ama-assn.org/ama1/pub/upload/mm/365/apricoxib.pdf.

Moberly et al., "A randomized, double-blind, celecoxib- and placebo-controlled study of the effectiveness of CS-706 in acute postoperative dental pain," Clin. Therapeutics, Excerpta Medica, 29 (3):399-412 (2007).

Murphey et al., "Quantification of the major urinary metabolite of PGE2 by a liquid chromatographic/mass spectrometric assay: determination of cyclooxygenase-specific PGE2 synthesis in healthy humans and those with lung cancer," Anal. Biochem. 334(2):266-275 (2004).

Samad et al., "Interleukin-1Beta-mediated induction of COX-2 in the CNS contributes to inflammatory pain hypersensitivity," Nature 410:471-475 (2001).

Ushiyama et al., "Preclinical pharmacology profile of CS-706, a novel cyclooxygenase-2 selective inhibitor, with potent antinociceptive and anti-inflammatory effects," Eur. J. Pharmacology 578(10):76-86 (2007).

EP08781744 Supplementary Search Report mailed Jul. 22, 2010.

Ann. Chem. 589, 176 (1954).

Asghamejad in "Transport Processes in Pharmaceutical Systems," Amidon et al., Ed., Marcell Dekker, 185-218, 2000.

Balant et al., "Prodrugs for the Improvement of Drug Absorption via Different Routes of Administration," Eur. J. Drug Metab. Pharmacokinet. 15:143-153 (1990).

Balimane and Sinko, "Involvement of Multiple Transporters in the Oral Absorption of Nucleoside Analogues," Adv. Drug Delivery Rev. 39:183-209 (1999).

Berge et al., "Pharmaceutical Salts," J. Pharma. Sci. 66:1-19 (1977).

Browne, "Fosphenytoin (Cerebyx)," Clin. Neuropharmacol. 20:1-12 (1997).

Bundgaard, "Bioreversible Derivatization of Drags-Principle and Applicability to Improve the Therapeutic Effects of Drugs," Arch. Pharm. Chem. 86:1:1-39 (1979).

Bundgaard, "Improved Drug Delivery by the Prodrug Approach," Controlled Drug Delivery 17:179-96 (1987).

Bundgaard, H., "Means to Enhance Penetration: Prodrugs as a Means to Improve the Delivery of Peptide Drugs," Advanced Drug Delivery Reviews 8: 1-38, 1992.

Farquhar et al., "Biologically Reversible Phosphate-Protective Groups," J. Pharm. Sci. 72:324-325 (1983).

Fleisher et al., "Improved Oral Drug Delivery: Solubility Limitations Overcome by the Use of Prodrugs," Advanced Drug Delivery Reviews 19(2):115-130, 1996.

Fleisher et al., "Design of Prodrugs for Improving Gastrointestinal Absorption by Intestinal Enzyme Targeting," Methods Enzymol. 112:360-381 (1985).

Freeman et al., "Bioreversible Protection for the Phospho Group: Chemical Stability and Bioactivation of Di(4-acetoxybenzyl) Methylphosphonate with Carboxyesterase," J. Chem. Soc. Chem. Commun. 875-877 (1991).

Friis and Bundgaard, "Prodrugs of Phosphates and Phosphonates: Novel Lipophilic α-Acyloxyalkyl Ester Derivatives of Phosphate- or Phosphonate Containing Drugs Masking the Negative Charges of These Groups," Eur. J. Pharm. Sci. 4:1:49-59 (1996).

Gaignault et al., "Designing Prodrugs and Bioprecursors I. Carrier Prodrugs," Pract. Med. Chem. 671-696 (1996).

Gangwar et al., "Prodrug, Molecular Structure and Percutaneous Delivery," Des. Biopharm. Prop. Prodrugs Analogs, 409-421 (1977).

Gill, G. N., et al., "Purification of Functionally Active Epidermal Growth Factor Receptor Protein Using a Competitive Antagonist Monoclonal Antibody and Competitive Elution with Epidermal Growth Factor," Methods in Enzymology, 146:82-86 (1987).

Harper, "Drug Latentiation," Progress in Drug Research 4:221-294 (1962).

Henry et al., "NSAIDs and Risk of Upper Gastrointestinal Bleeding," Lancet, 337:730 (1991).

Higuchi, "Pro-drug, molecular structure and percutaneous delivery," Design of Biopharmaceutical Properties through Prodrugs and Analogs, Chapter 14, pp. 409-421, ed. Roche.

Ihde, D. C. "Current Status of Therapy for Small Cell Carcinoma of the Lung," Cancer 54:2722-2728 (1984).

Koki et al., "Potential Utility of COX-2 Inhibitors in Chemoprevention and Chemotherapy," Exp. Opin., Invest. Drugs, 8:10:1623-38 (1999).

Lax et al., "Localization of a Major Receptor-Binding Domain for Epidermal Growth Factor by Affinity Labeling," Mol. And Cell Biol., 8:4:1831-1834 (1988).

Masferrer et al., "Celecoxib: A Specific Cox-2 Inhibitor with Anti-Angiogenic and Anti-Cancer Activities," Proc. Am. Assoc. Cancer Research, 40:396 (1999).

Mizen et al., "The Use of Esters as Prodrugs for Oral Delivery of β-Lactam Antibiotics," Pharm. Biotech. 11:345-365 (1998).
Nathwani and Wood, "A Current Review of Their Clinical Pharmacology and Therapeutic Use," Drugs 45:6:866-894 (1993).
Neal et al., "Epidermal Growth Factor Receptor in Human Bladder Cancer: Comparison of Invasive and Superficial Tumors," Lancet, 1:366-367 (1985).
Pauletti et al., "Improvement of Oral Peptidomimetics and Prodrug Strategies," Adv. Drug. Delivery Rev. 27:235-256 (1997).
PCT/US08/069894 Search Report Dated Oct. 5, 2008.
Posner et al., "Kinetic Model of the Epidermal Growth Factor (EGF) Receptor Tyrosine Kinase and a Possible Mechanism of its Activation by EGF," J. Biol. Chem., 267:29:20638-20647 (1992).
Sainsbury et al., "Epidermal-Growth-Factor Receptors and Estrogen Receptors in Human Breast Cancer," Lancet, 1: 364-366 (1985).
Santus and Baker, J. "Osmotic drug delivery: a review of the patent Literature," Controlled Release 35:1-21 (1995).
Santon et al., "Effects of Epidermal Growth Factor Receptor Concentration on Tumorigenicity of A431 Cells in Nude Mice," Cancer Res., 46:4701-4705 (1986).
Sinhababu and Thakker, "Prodrugs of Anticancer Agents," Adv. Drug Delivery Rev. 19:241-273 (1996).
Slamon et. al., "Studies of the HER-2/neu Proto-Oncogene in Human Breast and Ovarian Cancer," Science, 244:707-712 (1989).
Stella et al., "Prodrugs, Do they have Advantages in Clinical Practice?" Drugs 29:455-473 (1985).
Strauss, et al. "Multimodality Treatment of Stage IIIA Non-Small-Cell Lung Carcinoma: a Critical Review of the Literature and Strategies for Future Research," Journal of Clinical Oncology, 10: 829-838 (1992).
Subbaramaiah et al., "Cyclooxygenase 2: A Molecular Target for Cancer Prevention and Treatment," Trends Pharmacol. Sci., 24:96-102 (2003).
Tan et al., "Development and Optimization of Anti-HIV Nucleoside Analogs and Prodrugs:—A review of their cellular pharmacology, structure-activity relationships and pharmacokinetics," Adv. Drug Delivery Rev. 39:117-151 (1999).
Taylor, "Improved Passive Oral Drug Delivery via Prodrugs," Adv. Drug Delivery Rev. 19:131-148 (1996).
Thun et al., "Nonsteroidal Anti-inflammatory Drugs as Anticancer Agents: Mechanistic, Pharmacologic, and Clinical Issues" J. National Cancer Inst., 94:4:252-266 (2002).
Tripathy, D. et al., "Phenotypic and Proteomic Alterations of Acquired Trastuzumab Resistance," Journal of Clinical Oncology, 23:16S:3121 (2005).
Tsujii and DuBois, "Alterations in Cellular Adhesion and Apoptosis in Epithelial Cells Overexpressing Prostaglandin Endoperoxide Synthase 2," Cell, 83:493-501 (1995).
Ullrich et al., "Human Epidermal Growth Factor Receptor cDNA Sequence to Aberrant Expression of the Amplified Gene in A431 Epidermoid Carcinoma Cells," Nature, 309:418-25 (1986).
Valentino and Borchardt, "Prodrug Strategies to Enhance the Intestinal Absorption of Peptides," Drug Discovery Today 2:4:148-155 (1997).
Verma et al., "Osmotically Controlled Oral Drug Delivery," Drug Development and Industrial Pharmacy 26:7:695-708 (2000).
Verma et al., "Formulation Aspects in the Development of Osmotically Controlled Oral Drug Delivery Systems," J. Controlled Release 79:7-27 (2002).
Waller et al., "Prodrugs," Br. J. Clin. Pharmac. 28:5:497-507 (1989).
Wang et al., "Prodrug Approaches to the Improved Delivery of Peptide Drugs," Curr. Pharm. Design 5:265-287 (1999).
Wiebe and Knaus, "Concepts for the Design of Anti-HIV Nucleoside Prodrugs for Treating Cephalic HIV Infection," Adv. Drug Delivery Rev. 39:1:63-80 (1999).
Wilks, "Protein Tyrosine Kinase Growth Factor Receptors and their Ligands in Development, Differentiation, and Cancer," Adv. Cancer Res., 60:43 (1993).
Hadfield et al., "Tubulin and microtubules as targets for anticancer drugs," Progress in Cell Cycle Research 2003 LNKD-PUBMED:14593726, vol. 5, 2003, pp. 309-325, CP009151077, ISSN: 1087-2957.
Lu et al., "NSAID-Induced Apoptosis in Rous Sarcoma Virus-Transformed Chicken Embryo Fibroblasts is Dependent on v-src and c-myc and is Inhibited by bcl-2," Prostaglandins 54:549-568 (1997).
Whitehead et al., "A Phase II trial of epothilone B analoge BMS-247550 (NSC #710428) 1 xabepilone, in patients with advances pancreas cancer: A Southwest Oncology Group Study," Investigational New Drugs; The Journal of New Anticancer Agents, Kluwer Academic Publishers, BO, VO1. 24, No. 6, May 11, 2006, pp. 515-520, CP019394428, ISSN: 1573-0646.
EP 08854265 Supplementary Search Report dated Aug. 11, 2011.

* cited by examiner

METHODS AND COMPOSITIONS FOR THE TREATMENT OF CANCER, TUMORS, AND TUMOR-RELATED DISORDERS

CROSS-REFERENCE

This application claims the benefit of U.S. Provisional Application No. 60/949,483, filed Jul. 12, 2007; U.S. Provisional Application No. 60/990,900, filed Nov. 28, 2007; and U.S. Provisional Application No. 61/044,425, filed Apr. 11, 2008, the contents of which are incorporated herein by reference in their entirety.

FIELD

The present invention relates to combination compositions and the use of such combinations for the treatment of cancer, tumors, and tumor-related disorders.

BACKGROUND

Cancer, tumors, tumor-related disorders, and neoplastic disease states are serious and often times life-threatening conditions. These diseases and disorders, which are characterized by rapidly-proliferating cell growth, continue to be the subject of research efforts directed toward the identification of therapeutic agents which are effective in the treatment thereof. Such agents prolong the survival of the patient, inhibit the rapidly-proliferating cell growth associated with the neoplasm, or effect a regression of the neoplasm.

Generally, surgery and radiation therapy are the first modalities considered for the treatment of cancer that is considered locally confined, and offer the best prognosis. Chemotherapy treatment of certain cancers typically results in disappointing survival rates but still offer a survival benefit. For example, in patients with non-small cell lung cancer, platinum-based chemotherapy regimens, such as the use of either cisplatin or carboplatin plus one of either paclitaxel, docetaxel, gemcitabine, vinorelbine, irinotecan, etoposide, vinblastine, or bevacizumab is employed. If patients cannot tolerate this therapy, a single agent, such as N-(3-ethynylphenyl)-6,7-bis(2-methoxyethoxy)quinazolin-4-amine, commonly known as erlotinib (Tarceva®), can be used. Erlotinib targets the epidermal growth factor receptor tyrosine kinase which is highly expressed and occasionally mutated in various forms of cancer. If patients fail to respond to an erlotinib treatment, additional conventional treatment offers limited benefit.

Despite erlotinib's approval for the treatment of stage IIIB and IV non-small cell lung cancer, as with most therapeutic agents, side-effects result from its use. For example, common side effects, occurring in greater than 30% of patients taking erlotinib, include, rash, diarrhea, poor appetite, fatigue, shortness of breath, cough, nausea and vomiting. Additionally, less common side effects include infection, mouth sores, itching, dry skin, eye irritation, pulmonary fibrosis, and abdominal pain. Of greater concern, is the growing view that, while utilization of erlotinib for the treatment of tumors may initially shrink the size of the tumor, the tumor may eventually enlarge in size, indicating, among other things, the development of resistance. Erlotinib may be representative of the types of therapeutic agents being used for cancer treatment; in that its use has an effect on cancer, but because of other factors, which are not entirely known, the tumor develops resistance and progresses.

What is needed, therefore, are compositions and/or methods of treatment for cancer which take advantage of the synergy found in a therapeutic combination that could increase the effectiveness of the agents and reduce and/or eliminate the side effects typically associated with conventional treatments.

SUMMARY OF THE INVENTION

The present invention is based at least in part on a synergistic effect obtained in treating conditions such as cancer by a combination comprising a COX-2 selective inhibitor and an EGFR inhibitor. Some of the possible favorable outcomes for synergism include 1) increasing the efficacy of the therapeutic effect, 2) decreasing the dosage but increasing or maintaining the same efficacy to avoid toxicity, 3) minimizing or slowing down the development of drug resistance, and 4) providing selective synergism against target (or efficacy synergism) versus host (or toxicity antagonism).

While some embodiments of the invention are illustrated through a fixed dose combination comprising a COX-2 inhibitor and an EGFR inhibitor, the embodiments of the invention cover compositions and methods wherein the COX-2 inhibitor and the EGFR inhibitor are provided in separate dosage forms.

The present invention is based, at least in part on the discovery that combinations of a 1,2-diphenylpyrrole derivative and an EGFR inhibitor provide numerous advantages in the treatment of cancer, tumors, and tumor-related disorders. These combinations may allow for lesser amounts of each particular agent to be delivered and may produce the same or better effect as a greater amount of each particular agent. For example, a combination of a 1,2-diphenylpyrrole derivative and an EGFR inhibitor (provided in one fixed dose or in two separate dosage forms) will increase therapeutic efficacy, reduce side effects, reduce resistance, and when a fixed dose is used reduce the pill burden, enhance patient compliance, and thus, support a more favorable treatment setting and outcome. Such combinations can further increase the benefit of each particular agent which otherwise would be only marginally effective. As such, this synergistic or enhancement effect can be employed in the treatment of cancer, tumors, and tumor-related disorders, and may overcome resistance of tumors to drugs at conventional doses.

Methods of Use

The present invention provides a method for treating cancer, tumors, and tumor-related disorders. For example, the method comprises administering to a subject in a combination therapy an amount of a COX-2 selective inhibitor and an EGFR inhibitor, wherein the COX-2 selective inhibitor and the EGFR inhibitor combine to give a therapy suitable for treating a cancer, tumor, and tumor-related disorders.

The invention further provides combinations of COX-2 selective inhibitors and EGFR inhibitors for antineoplastic, anti-tumor, anti-cancer combination therapy. In one embodiment the invention provides compositions comprising a combination of a COX-2 selective inhibitor and an EGFR inhibitor. The invention also provides for the use of combinations of 1,2-diphenylpyrrole derivatives and an EGFR inhibitor and/or their pharmaceutically acceptable salt, solvate, or prodrug, as antineoplastic, anti-tumor, or anti-cancer combination therapy.

In one embodiment, the invention provides a method for treating a subject having cancer, comprising administering to the subject, a therapeutically effective amount of a combination comprising a 1,2-diphenylpyrrole derivative and an EGFR inhibitor or their respective pharmaceutically acceptable salt, solvate or prodrug.

In one embodiment, the 1,2-diphenylpyrrole derivative of the combination composition has the following formula:

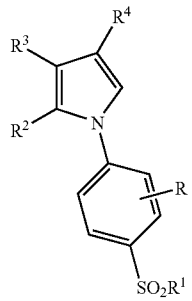

wherein:

R is a hydrogen atom, a halogen atom or an alkyl group having from 1 to 6 carbon atoms;

$R^1$ is an alkyl group having from 1 to 6 carbon atoms or an amino group;

$R^2$ is a phenyl group which is unsubstituted or is substituted by at least one substituent selected from the group consisting of substituents α and substituents β;

$R^3$ is a hydrogen atom, a halogen atom or an alkyl group which has from 1 to 6 carbon atoms and which is unsubstituted or is substituted by at least one substituent selected from the group consisting of a hydroxy group, a halogen atom, an alkoxy group having from 1 to 6 carbon atoms and an alkylthio group having from 1 to 6 carbon atoms;

$R^4$ is a hydrogen atom; an alkyl group which has from 1 to 6 carbon atoms and which is unsubstituted or is substituted by at least one substituent selected from the group consisting of a hydroxy group, a halogen atom, an alkoxy group having from 1 to 6 carbon atoms and an alkylthio group having from 1 to 6 carbon atoms; a cycloalkyl group having from 3 to 8 carbon atoms, an aryl group; or an aralkyl group; said aryl group having from 6 to 14 ring carbon atoms in a carbocyclic ring and are unsubstituted or are substituted by at least one substituent selected from the group consisting of substituents α and substituents β;

said aralkyl group are an alkyl group having from 1 to 6 carbon atoms and which are substituted by at least one aryl group as defined above;

said substituents α are selected from the group consisting of a hydroxy group, a halogen atom, an alkoxy group having from 1 to 6 carbon atoms and an alkylthio group having from 1 to 6 carbon atoms;

said substituents β are selected from the group consisting of an alkyl group which has from 1 to 6 carbon atoms and which is unsubstituted or are substituted by at least one substituent selected from the group consisting of a hydroxy group, a halogen atom, an alkoxy group having from 1 to 6 carbon atoms and an alkylthio group having from 1 to 6 carbon atoms; an alkanoyloxy group having from 1 to 6 carbon atoms; a mercapto group; an alkanoylthio group having from 1 to 6 carbon atoms; an alkylsulfinyl group having from 1 to 6 carbon atoms; a cycloalkloxy group having from 3 to 8 carbon atoms; a haloalkoxy group having from 1 to 6 carbon atoms; and an alkylenedioxy group having from 1 to 6 carbon atoms; or a pharmaceutically acceptable salt, solvate, or prodrug.

In another embodiment, a 1,2-diphenylpyrrole derivative of the combination composition has the following formula:

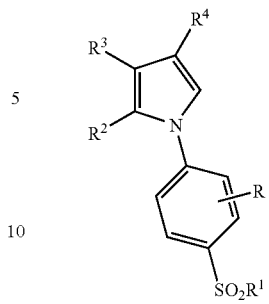

R is a hydrogen atom, a halogen atom or an alkyl group having from 1 to 4 carbon atoms;

$R^1$ is a methyl group or an amino group;

$R^2$ is an unsubstituted phenyl group or a phenyl group which is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and which is substituted by at least one substituent selected from the group consisting of a halogen atom, an alkoxy group having from 1 to 4 carbon atoms and an alkylthio group having from 1 to 4 carbon atoms; a haloalkoxy group having from 1 to 4 carbon atoms; and an alkylenedioxy group having from 1 to 4 carbon atoms;

$R^3$ is a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;

$R^4$ is a hydrogen atom; an unsubstituted alkyl group having from 1 to 4 carbon atoms; a substituted alkyl group having from 1 to 4 carbon atoms and substituted by at least one substituent selected from the group consisting of a hydroxy group, a halogen atom, an alkoxy group having from 1 to 4 carbon atoms and an alkylthio group having from 1 to carbon atoms; a cycloalkyl group having from 3 to 6 carbon atoms; an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and substituted by at least one substituent selected from the group consisting of a hydroxy group, a halogen atom, an alkoxy group having from 1 to 4 carbon atoms and an alkylthio group having from 1 to 4 carbon atoms; and a cycloalkyloxy group having from 3 to 7 carbon atoms; an aralkyl group having from 1 to 4 carbon atoms in the alkyl part and containing at least one said aryl group; or a pharmaceutically acceptable salt, solvate, or prodrug.

In a further embodiment, the invention provides a 1,2-diphenylpyrrole derivative of the combination composition wherein:

R is a hydrogen atom;

$R^1$ is an amino group;

$R^2$ is an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a haloalkoxy group having from 1 to 4 carbon atoms and a alkylenedioxy group having from 1 to 4 carbon atoms;

$R^3$ is a hydrogen atom, a halogen atom, an alkyl group having from 1 to 4 carbon atoms or a haloalkyl group having from 1 to 4 carbon atoms;

$R^4$ is a hydrogen atom; an unsubstituted alkyl group having from 1 to 4 carbon atoms; a substituted alkyl group having from 1 to 4 carbon atoms and substituted by at least one substituent selected from the group consisting of a hydroxy group and an alkoxy group having from 1 to 4 carbon atoms; a cycloalkyl group having from 3 to 6 carbon atoms; an aryl group which has from 6 to 10 ring carbon atoms and which is unsubstituted or is substituted by at least one substituent selected from the group consisting of a hydroxy group; a halogen atom; an alkoxy group having from 1 to 4 carbon atoms; an unsubstituted alkyl group having from 1 to 4 carbon atoms; an alkyl group having from 1 to 4 carbon atoms and which is unsubstituted or substituted by at least one halogen atom; and a cycloalkyloxy group having from 3 to 7 carbon atoms; and an aralkyl group having from 1 to 4 carbon atoms in the alkyl part and containing at least one said aryl group; or a pharmaceutically acceptable salt, solvate, or prodrug.

In yet a further embodiment, the 1,2-diphenylpyrrole derivative is selected from the group consisting of: 4-methyl-2-(4-methylphenyl)-1-(4-sulfamoylphenyl)pyrrole; 2-(4-methoxyphenyl)-4-methyl-1-(4-sulfamoylphenyl)pyrrole; 2-(4-chlorophenyl)-4-methyl-1-(4-sulfamoylphenyl)pyrrole; 4-methyl-2-(4-methylthiophenyl)-1-(4-sulfamoylphenyl)pyrrole; 2-(4-ethoxyphenyl)-4-methyl-1-(4-sulfamoylphenyl)pyrrole; 2-(4-methoxy-3-methylphenyl)-4-methyl-1-(4-sulfamoylphenyl)pyrrole; 2-(3-fluoro-4-methoxyphenyl)-4-methyl-1-(4-sulfamoylphenyl)pyrrole; 2-(3,4-dimethylphenyl)-4-methyl-1-(4-sulfamoylphenyl)pyrrole; 4-methyl-1-(4-methylthiophenyl)-2-(4-sulfamoylphenyl)pyrrole; 1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole.

In one embodiment the 1,2-diphenylpyrrole derivative is 2-(4-ethoxyphenyl)-4-methyl-1-(4-sulfamoylphenyl)-pyrrole2-(4-ethoxyphenyl)-4-methyl-1-(4-sulfamoylphenyl)-pyrrole.

In another embodiment the EGFR inhibitor is erlotinib.

In a further embodiment, the 1,2-diphenylpyrrole derivative is 2-(4-ethoxyphenyl)-4-methyl-1-(4-sulfamoylphenyl)-pyrrole2-(4-ethoxyphenyl)-4-methyl-1-(4-sulfamoylphenyl)-pyrrole and the EGFR inhibitor is erlotinib.

In yet a further embodiment the 1,2-diphenylpyrrole derivative and the EGFR inhibitor are administered sequentially in either order or simultaneously.

In one embodiment the 1,2-diphenylpyrrole derivative is administered first.

In another embodiment the EGFR inhibitor is administered first.

In one embodiment, the invention provides a method for treating cancer, tumors, and tumor-related disorders, comprising administering the combination by a mode of administration comprising oral, parenteral, buccal, intranasal, epidural, sublingual, pulmonary, local, rectal, or transdermal administration.

In another embodiment, the invention provides a method for treating cancer, tumors, and tumor-related disorders wherein the combination is orally administered as a single dosage form.

In another embodiment, the invention provides a method for treating cancer, tumors, and tumor-related disorders wherein the single dosage form enhances patient compliance and/or reduces pill burden.

In a further embodiment, the invention provides a method for treating cancer, tumors, and tumor-related disorders wherein the single dosage form is a single capsule or a single tablet.

In yet a further embodiment, the invention provides a method for treating cancer, tumors, and tumor-related disorders wherein the composition is provided as a single tablet.

In a further embodiment, the invention provides a method for treating cancer, tumors, and tumor-related disorders, comprising administering the combination by a mode of parenteral administration selected from intravenous, subcutaneous, intrathecal, and intramuscular administration.

Dosages

In one embodiment, the invention provides a method for treating cancer, tumors, and tumor-related disorders comprising administering the combination in a single tablet wherein the single tablet comprises from about 1 mg to about 1200 mg of 2-(4-ethoxyphenyl)-4-methyl-1-(4-sulfamoylphenyl)-pyrrole and from about 25 mg to about 450 mg of erlotinib.

In another embodiment, the invention provides a method for treating cancer, tumors, and tumor-related disorders wherein the single tablet comprises from about 1 mg to about 1200 mg 2-(4-ethoxyphenyl)-4-methyl-1-(4-sulfamoylphenyl)-pyrrole and about 25 mg of erlotinib.

In a further embodiment, the invention provides a method for treating cancer, tumors, and tumor-related disorders wherein the single tablet comprises from about 1 mg to about 1200 mg 2-(4-ethoxyphenyl)-4-methyl-1-(4-sulfamoylphenyl)-pyrrole and about 100 mg of erlotinib.

In yet a further embodiment, the invention provides a method for treating cancer, tumors, and tumor-related disorders wherein the single tablet comprises from about 1 mg to about 1200 mg 2-(4-ethoxyphenyl)-4-methyl-1-(4-sulfamoylphenyl)-pyrrole and about 150 mg of erlotinib.

In another embodiment, the invention provides a method for treating cancer, tumors, and tumor-related disorders wherein the single tablet comprises from about 1 mg to about 1200 mg 2-(4-ethoxyphenyl)-4-methyl-1-(4-sulfamoylphenyl)-pyrrole and about 200 mg of erlotinib.

In yet another embodiment, the invention provides a method for treating cancer, tumors, and tumor-related disorders wherein the single tablet comprises from about 1 mg to about 1200 mg 2-(4-ethoxyphenyl)-4-methyl-1-(4-sulfamoylphenyl)-pyrrole and about 300 mg of erlotinib.

In a further embodiment, the invention provides a method for treating cancer, tumors, and tumor-related disorders wherein the single tablet comprises from about 1 mg to about 1200 mg 2-(4-ethoxyphenyl)-4-methyl-1-(4-sulfamoylphenyl)-pyrrole and about 450 mg of erlotinib.

In one embodiment, the invention provides a method for treating cancer, tumors, and tumor-related disorders wherein the single tablet comprises about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 25 mg of erlotinib.

In one embodiment, the invention provides a method for treating cancer, tumors, and tumor-related disorders wherein the single tablet comprises about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 100 mg of erlotinib.

In another embodiment, the invention provides a method for treating cancer, tumors, and tumor-related disorders wherein the single tablet comprises about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 150 mg of erlotinib.

In one embodiment, the invention provides a method for treating cancer, tumors, and tumor-related disorders wherein the single tablet comprises about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 200 mg of erlotinib.

In another embodiment, the invention provides a method for treating cancer, tumors, and tumor-related disorders wherein the single tablet comprises about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 300 mg of erlotinib.

In a further embodiment, the invention provides a method for treating cancer, tumors, and tumor-related disorders wherein the single tablet comprises about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 450 mg of erlotinib.

In one embodiment, the invention provides a method of treating cancer, tumors, and tumor-related disorders comprising administering a composition comprising a combination of a 1,2-diphenylpyrrole derivative and an EGFR inhibitor wherein the composition is suitable for once-daily administration.

In a further embodiment, the invention provides a method wherein administering the combination enhances treatment of the subject compared to administering one component of the combination alone.

Types of Cancer

In yet a further embodiment, the invention provides a method wherein administering the combination reduces the side effects of treatment for a cancer, tumor, and tumor-related disorders.

In one embodiment the cancer is selected from the group consisting of: oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, glioma; parathyroid cancer, penile cancer, vaginal cancer, thyroid cancer, pancreatic cancer, esophageal cancer, Hodgkin's lymphoma, leukemia-related disorders, mycosis fungoides, and myelodysplastic syndrome.

In another embodiment the cancer is non-small cell lung cancer, pancreatic cancer, breast cancer, ovarian cancer, colorectal cancer, or head and neck cancer.

In yet another embodiment the cancer is a carcinoma, a tumor, a neoplasm, a lymphoma, a melanoma, a glioma, a sarcoma, or a blastoma.

In one embodiment the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In another embodiment the tumor is selected from the group consisting of: astrocytic tumors, malignant mesothelial tumors, ovarian germ cell tumors, supratentorial primitive neuroectodermal tumors, Wilms tumors, pituitary tumors, extragonadal germ cell tumors, gastrinoma, germ cell tumors, gestational trophoblastic tumors, brain tumors, pineal and supratentorial primitive neuroectodermal tumors, pituitary tumors, somatostatin-secreting tumors, endodermal sinus tumors, carcinoids, central cerebral astrocytoma, glucagonoma, hepatic adenoma, insulinoma, medulloepithelioma, plasmacytoma, vipoma, and pheochromocytoma.

In yet another embodiment the neoplasm is selected from the group consisting of: intraepithelial neoplasia, multiple myeloma/plasma cell neoplasm, plasma cell neoplasm, interepithelial squamous cell neoplasia, endometrial hyperplasia, focal nodular hyperplasia, hemangioendothelioma, and malignant thymoma.

In a further embodiment the lymphoma is selected from the group consisting of: nervous system lymphoma, AIDS-related lymphoma, cutaneous T-cell lymphoma, non-Hodgkin's lymphoma, lymphoma, and Waldenstrom's macroglobulinemia.

In another embodiment the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In yet another embodiment the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In one embodiment the glioma is selected from the group consisting of: glioma, brain stem glioma, and hypothalamic and visual pathway glioma.

In another embodiment the blastoma is selected from the group consisting of: pulmonary blastoma, pleuropulmonary blastoma, retinoblastoma, neuroblastoma, medulloblastoma, glioblastoma, and hemangiblastomas.

EGFR Inhibitors

In a further embodiment, the invention provides a method wherein the EGFR inhibitor is a small molecule compound or an antibody.

In one embodiment, the invention provides a method wherein the small molecule compound is selected from the group consisting of: ZM-254530, BIBX-1382, reveromycin A, gefitinib, CGP-57148, CGP-59326, 4-(3-chloro)-5,6-dimethyl-7H-pyrrolo[2,3-d]pyrimidine, tyrphostin, PKI-166, PD 153035, EKB-569, and 4-(phenylamino)quinazolines, or their pharmaceutically acceptable salts, solvates, or prodrugs.

In another embodiment the invention provides a method wherein the antibody is selected from the group consisting of: EGF receptor antibody, MR1scFvPE38 KDEL MDX-447, MDX-210, MD-72000, MDX-260, wayne anti-EGFR Mabs, anti-EGFr Mab, anti-EGFr MAb, Genen anti-EGFR Mab, MAb DC-101, trastuzumab, anti-VEGF monoclonal, anti-EGFR-DM1 Ab, MAb 4D5, BAB447, EMD-55900, EMD-6200, -82633, anti-EGFR Mab, MAb 4D5, cetuximab, anti-EGFr MAb, anti-flk-1, CCX, CCZ, anti-flk-1, AG-514, AG-568, nti-EGFR-DM1 Ab, MDX-447, TgDCC-E1A and C225, matuzumab, panitumumab, DWPA408, and RC-394011.

In another embodiment the EGFR inhibitor is selected from the group consisting of: muellerian-inhibiting hormone, TNP470, tecogalan sodium, EGF receptor antisense, PI-88, oligonucleotide, bromelain molecules, amphiregulin, EGF fusion toxin, EGF fusion protein, Amphiregulin hbEGF-toxin, hbEGF-toxin, and EGF fusion protein.

Further Methods of Use

In one embodiment, the invention provides a method of inducing differentiation of tumor cells, the method comprising contacting the cells with an effective amount of a combination comprising a 1,2-diphenylpyrrole derivative and an EGFR inhibitor whereby the combination induces differentiation of tumor cells.

In one embodiment, the invention provides a method of inhibiting proliferation of cancer cells, the method comprising contacting a cancer cell with a combination comprising a 1,2-diphenylpyrrole derivative and an EGFR inhibitor whereby the combination inhibits proliferation of cancer cells.

In another embodiment, the invention provides a method for reducing proliferation of cancer cells, the method comprising delivering to the cells a combination comprising a 1,2-diphenylpyrrole derivative and an EGFR inhibitor, whereby the reduction of cell proliferation is greater than a reduction caused by either a 1,2-diphenylpyrrole derivative alone or an EGFR inhibitor alone.

In one embodiment, the invention provides a method of modulating autophosphorylation with a molecule of ATP, the method comprising delivering to a cancer cell an effective amount of a combination comprising a 1,2-diphenylpyrrole derivative and an EGFR inhibitor wherein the combination inhibits autophosphorylation with a molecule of ATP.

In a further embodiment, the invention provides a method of inhibiting metastases of tumor cells, the method comprising administering an effective amount of a combination comprising a 1,2-diphenylpyrrole derivative and an EGFR inhibitor such that the combination inhibits metastatic activity of tumor cells.

In one embodiment, the invention provides a method for inducing apoptosis in cancer cells, the method comprising contacting the cancer cells with a combination comprising a 1,2-diphenylpyrrole derivative and an EGFR kinase sufficient to induce apoptosis.

In another embodiment, the invention provides a method for sensitizing EGFR-inhibitor resistant cancer cells to an EGFR inhibitor, the method comprising administering a combination comprising a 1,2-diphenylpyrrole derivative and an EGFR inhibitor wherein the combination sensitizes the cancer cells to the EGFR inhibitor.

In one embodiment, the invention provides a method of treating EGFR resistance in a cancer cell, the method comprising, administering a combination comprising a 1,2-diphenylpyrrole derivative and an EGFR inhibitor In a further embodiment, the invention provides a method of modulating prostaglandin synthesis in a cancer cell, the method comprising contacting the cell with a combination comprising a 1,2-diphenylpyrrole derivative and an EGFR inhibitor wherein the combination inhibits prostaglandin synthesis in a cancer cell.

In one embodiment, the invention provides a method of modulating cyclooxygenase expression in a cancer cell, the method comprising delivering to the cell a combination comprising a 1,2-diphenylpyrrole derivative and an EGFR inhibitor wherein the combination inhibits cyclooxygenase expression in a cancer cell.

In one embodiment, the invention provides a method of modulating angiogenesis in a cancer cell, the method comprising contacting the cell with a combination comprising a 1,2-diphenylpyrrole derivative and an EGFR inhibitor wherein the combination inhibits angiogenesis in a cancer cell.

In another embodiment, the invention provides a method of reducing the dosage in conventional treatment for neoplasia and/or neoplasia related disorders in a subject, the method comprising administering to a subject a combination of a 1,2-diphenylpyrrole derivative and an EGFR inhibitor wherein the combination reduces the dosage in conventional treatment for neoplasia and/or neoplasia-related disorders.

In one embodiment, the invention provides a method of treating neoplasia and/or neoplasia related disorders, the method comprising administering a combination of a 1,2-diphenylpyrrole derivative and an EGFR inhibitor In one embodiment, the invention provides a composition for treating cancer comprising, a combination of a 1,2-diphenylpyrrole derivative and an EGFR inhibitor or their respective pharmaceutically acceptable salt, solvate or prodrug.

In one embodiment, the invention provides a method of treatment comprising administering a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole.

In another embodiment, the invention provides a method of treatment comprising administering a composition comprising a combination of a 1,2-diphenylpyrrole derivative and an EGFR inhibitor, wherein the EGFR inhibitor is erlotinib.

In yet another embodiment, the invention provides a method of treatment comprising administering a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment, the invention provides a method of treatment comprising administering a composition comprising a combination of a 1,2-diphenylpyrrole derivative and an EGFR inhibitor wherein the composition is a single dosage form.

In a further embodiment, the invention provides a method of treatment comprising administering a composition comprising a combination of a 1,2-diphenylpyrrole derivative and an EGFR inhibitor wherein a single dosage form enhances patient compliance and/or reduces pill burden.

In one embodiment, the invention provides a method for treating cancer, tumors, and tumor-related disorders, comprising administering a combination according to the invention by a mode of administration comprising oral, parenteral, buccal, intranasal, epidural, sublingual, pulmonary, local, rectal, or transdermal administration.

In a further embodiment, the invention provides a method for treating cancer, tumors, and tumor-related disorders, comprising a combination according to the invention by parenteral administration selected from intravenous, subcutaneous, intrathecal, and intramuscular administration.

In one embodiment, the invention provides a method comprising administering the combination in a single dosage form.

In yet a further embodiment, the invention provides a method of treatment comprising administering a composition comprising a single tablet combination of a 1,2-diphenylpyrrole derivative and an EGFR inhibitor wherein a single dosage form is a single capsule or a single tablet.

In one embodiment, the invention provides a method of treatment comprising administering a composition comprising a combination of a 1,2-diphenylpyrrole derivative and an EGFR inhibitor wherein the composition is in the form of a single tablet.

In another embodiment, the invention provides a method of treatment comprising administering a composition comprising a combination of a 1,2-diphenylpyrrole derivative and an EGFR inhibitor wherein the single tablet comprises from about 1 mg to about 1200 mg of 2-(4-ethoxyphenyl)-4-methyl-1-(4-sulfamoylphenyl)-pyrrole and from about 25 mg to about 450 mg of erlotinib.

In yet another embodiment, the invention provides a method of treatment comprising administering a composition comprising a combination of a 1,2-diphenylpyrrole derivative and an EGFR inhibitor wherein the single tablet comprises from about 1 mg to about 1200 mg 2-(4-ethoxyphenyl)-4-methyl-1-(4-sulfamoylphenyl)-pyrrole and about 25 mg of erlotinib.

In one embodiment, the invention provides a method of treatment comprising administering a single tablet composition comprising a combination of a 1,2-diphenylpyrrole derivative and an EGFR inhibitor wherein the single tablet comprises from about 1 mg to about 1200 mg 2-(4-ethoxyphenyl)-4-methyl-1-(4-sulfamoylphenyl)-pyrrole and about 100 mg of erlotinib.

In another embodiment, the invention provides a method of treatment comprising administering a composition comprising a combination of a 1,2-diphenylpyrrole derivative and an EGFR inhibitor wherein the single tablet comprises from about 1 mg to about 1200 mg 2-(4-ethoxyphenyl)-4-methyl-1-(4-sulfamoylphenyl)-pyrrole and about 150 mg of erlotinib.

In another embodiment, the invention provides a method of treatment comprising administering a composition comprising a combination of a 1,2-diphenylpyrrole derivative and an EGFR inhibitor wherein the single tablet comprises from about 1 mg to about 1200 mg 2-(4-ethoxyphenyl)-4-methyl-1-(4-sulfamoylphenyl)-pyrrole and about 200 mg of erlotinib.

In another embodiment, the invention provides a method of treatment comprising administering a composition comprising a combination of a 1,2-diphenylpyrrole derivative and an EGFR inhibitor wherein the single tablet comprises from about 1 mg to about 1200 mg 2-(4-ethoxyphenyl)-4-methyl-1-(4-sulfamoylphenyl)-pyrrole and about 300 mg of erlotinib.

In another embodiment, the invention provides a method of treatment comprising administering a composition comprising a combination of a 1,2-diphenylpyrrole derivative and an EGFR inhibitor wherein the single tablet comprises from about 1 mg to about 1200 mg 2-(4-ethoxyphenyl)-4-methyl-1-(4-sulfamoylphenyl)-pyrrole and about 450 mg of erlotinib.

In a further embodiment, the invention provides a method of treatment comprising administering a single tablet composition comprising a combination of a 1,2-diphenylpyrrole derivative and an EGFR inhibitor wherein the single tablet comprises from about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 25 mg of erlotinib.

In a further embodiment, the invention provides a method of treatment comprising administering a single tablet composition comprising a combination of a 1,2-diphenylpyrrole derivative and an EGFR inhibitor wherein the single tablet comprises from about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 100 mg of erlotinib.

In a further embodiment, the invention provides a method of treatment comprising administering a single tablet composition comprising a combination of a 1,2-diphenylpyrrole derivative and an EGFR inhibitor wherein the single tablet comprises from about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 150 mg of erlotinib.

In a further embodiment, the invention provides a method of treatment comprising administering a single tablet composition comprising a combination of a 1,2-diphenylpyrrole derivative and an EGFR inhibitor wherein the single tablet comprises from about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 200 mg of erlotinib.

In a further embodiment, the invention provides a method of treatment comprising administering a single tablet composition comprising a combination of a 1,2-diphenylpyrrole derivative and an EGFR inhibitor wherein the single tablet comprises from about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 300 mg of erlotinib.

In a further embodiment, the invention provides a method of treatment comprising administering a single tablet composition comprising a combination of a 1,2-diphenylpyrrole derivative and an EGFR inhibitor wherein the single tablet comprises from about 1 mg, about 5 mg, about 10 mg, about 25 mg, about 50 mg, about 100 mg, about 200 mg, about 300 mg, about 400 mg, about 600 mg, about 800 mg, about 1000 mg, or about 1200 mg 2-(4-ethoxyphenyl)-4-methyl-1-(4-sulfamoylphenyl)-pyrrole and about 450 mg of erlotinib.

In one embodiment, the invention provides a method of treatment comprising administering a composition comprising a combination of a 1,2-diphenylpyrrole derivative and an EGFR inhibitor wherein the composition is suitable for once-daily administration.

In another embodiment, the invention provides a method of treatment comprising administering a composition comprising a combination of a 1,2-diphenylpyrrole derivative and an EGFR inhibitor wherein the EGFR inhibitor is a small molecule compound or an antibody.

In a further embodiment, the invention provides a method of treatment comprising administering a composition comprising a combination of a 1,2-diphenylpyrrole derivative and a small molecule wherein the small molecule compound is selected from the group consisting of: ZM-254530, BIBX-1382, reveromycin A, gefitinib, CGP-57148, CGP-59326, 4-(3-chloro)-5,6-dimethyl-7H-pyrrolo[2,3-d]pyrimidine, tyrphostin, PKI-166, PD 153035, EKB-569, and 4-(phenylamino)quinazolines, or their pharmaceutically acceptable salts, solvates, or prodrugs.

In another embodiment, the invention provides a method of treatment comprising administering a composition comprising a combination of a 1,2-diphenylpyrrole derivative and an EGFR inhibitor wherein the EGFR inhibitor is an antibody selected from the group consisting of: EGF receptor antibody, MR1scFvPE38 KDEL MDX-447, MDX-210, MD-72000, MDX-260, wayne anti-EGFR Mabs, anti-EGFr Mab, anti-EGFr MAb, Genen anti-EGFR Mab, MAb DC-101, trastuzumab, anti-VEGF monoclonal, anti-EGFR-DM1 Ab, MAb 4D5, BAB-447, EMD-55900, EMD-6200, -82633, anti-EGFR Mab, MAb 4D5, cetuximab, anti-EGFr MAb, anti-flk-1, CCX, CCZ, anti-flk-1, AG-514, AG-568, nti-EGFR-DM1 Ab, MDX-447, TgDCC-E1A, C225, matuzumab, panitumumab, DWP408, and RC-3940II.

In yet another embodiment, the invention provides a method of treatment comprising administering a composition comprising a combination of a 1,2-diphenylpyrrole derivative and an EGFR inhibitor wherein the composition contains a lower dose of an EGFR inhibitor than a conventional treatment for cancer.

In a further embodiment, the invention provides a method of treatment comprising administering a composition comprising a combination of a 1,2-diphenylpyrrole derivative and an EGFR inhibitor wherein the composition reduces the side effects of cancer treatment.

In yet a further embodiment, the invention provides a method of treatment comprising administering a composition comprising a combination of a 1,2-diphenylpyrrole derivative and an EGFR inhibitor wherein the composition enhances treatment of cancer.

Pharmaceutical Compositions

In one embodiment the invention provides a pharmaceutical composition for treating cancer comprising, a combination of a 1,2-diphenylpyrrole derivative and an EGFR inhibitor, and a pharmaceutically acceptable excipient or carrier.

In one embodiment, the invention provides a pharmaceutical composition for treating cancer wherein the 1,2-diphenylpyrrole derivative is 2-(4-ethoxyphenyl)-4-methyl-1-(4-sulfamoylphenyl)-pyrrole.

In another embodiment, the invention provides a pharmaceutical composition for treating cancer wherein the EGFR inhibitor is erlotinib.

In yet another embodiment, the invention provides a pharmaceutical composition for treating cancer wherein the 1,2-diphenylpyrrole derivative is 2-(4-ethoxyphenyl)-4-methyl-1-(4-sulfamoylphenyl)-pyrrole and the EGFR inhibitor is erlotinib.

Kits/Articles of Manufacture

In one embodiment the invention provides a kit for treating cancer comprising a single dosage form comprising a combination of a 1,2-diphenylpyrrole derivative and an EGFR inhibitor and instructions on administration.

In one embodiment the invention provides a kit for treating cancer having a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

INCORPORATION BY REFERENCE

All publications, patents, and patent applications described in this specification are herein incorporated by reference to the same extent as if each individual publication, patent, or patent application was specifically and individually indicated to be incorporated by reference.

DETAILED DESCRIPTION

Figure 1A:
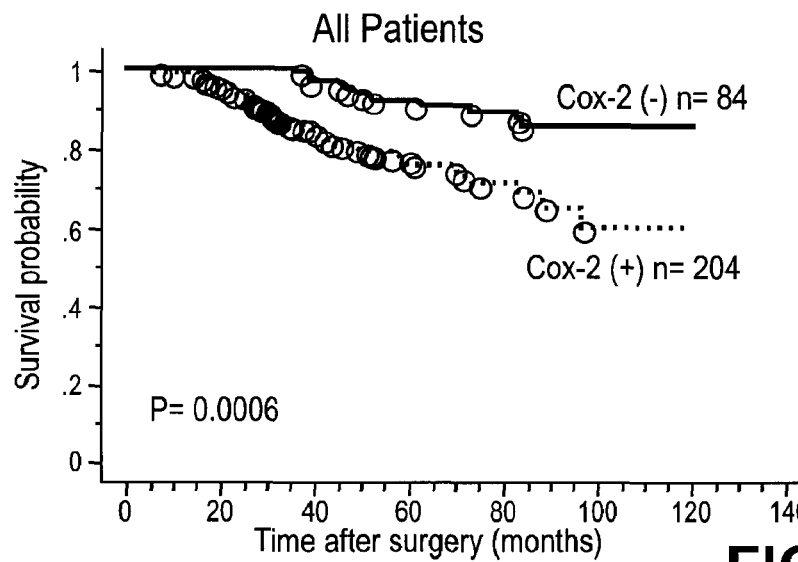
FIG. 1 provides graphs illustrating COX-2 expression levels in colorectal cancer.

To facilitate understanding of the disclosure set forth herein, a number of terms are defined below.

DEFINITIONS

As used herein, "abnormal cell growth," refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restenosis. Abnormal cell growth, also refers to and includes the abnormal growth of cells, both benign and malignant, resulting from activity of the enzymes farnesyl protein transferase, protein kinases, protein phosphatases, lipid kinases, lipid phosphatases, or activity of transcription factors, or intracellular or cell surface receptor proteins.

"Neoplasia" as described herein, is an abnormal, unregulated and disorganized proliferation of cells that is distinguished from normal cells by autonomous growth and somatic mutations. An accumulation of neoplastic cells is also known as a neoplasm, or tumor. As neoplastic cells grow and divide they pass on their genetic mutations and proliferative characteristics to progeny cells. In some embodiments, the neoplasm can be benign or malignant.

"Metastasis," as used herein, refers to the dissemination of tumor cells via lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance.

As discussed herein, "angiogenesis" is prominent in tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors such as renal cell carcinoma, hepatocellular carcinoma, and benign tumors such as acoustic neuroma, and neurofibroma, trachoma and pyogenic granulomas. Angiogenesis has been associated with blood-born tumors such as leukemias. It is believed that angiogenesis plays a role in the abnormalities in the bone marrow that give rise to leukemia.

Prevention of angiogenesis could halt the growth of cancerous tumors and the resultant damage to the subject due to the presence of the tumor.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition; or one or more of the symptoms associated with the disorder, disease, or condition; or alleviating or eradicating the cause(s) of the disorder, disease, or condition itself.

The term "therapeutically effective amount" refers to the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

Cyclooxygenase

Cyclooxygenase (COX) is an enzyme that is responsible for the formation of important biological mediators called prostanoids, including prostaglandins, prostacyclin and thromboxane. COX converts arachidonic acid, an ω-6 essential fatty acid, to prostaglandin $H_2$ ($PGH_2$), the precursor of the series-2 prostanoids. The enzyme contains two active sites: a heme with peroxidase activity, responsible for the reduction of $PGG_2$ to $PGH_2$, and a cyclooxygenase site, where arachidonic acid is converted into the hydroperoxy endoperoxide prostaglandin $G_2$ ($PGG_2$). The reaction proceeds through a hydrogen atom abstraction from arachidonic acid by a tyrosine radical generated by the peroxidase active site, then two oxygen molecules react with the arachidonic acid radical, giving $PGG_2$.

COX-1 is a constitutive enzyme responsible for biosynthesis of prostaglandins in the gastric mucosa and in the kidney among other sites. COX-2 is an enzyme that is produced by an inducible gene that is responsible for biosynthesis of prostaglandins in inflammatory cells. Inflammation causes induction of COX-2, leading to release of prostanoids (prostaglandin E2), which sensitize peripheral nociceptor terminals and produce localized pain hypersensitivity, inflammation and edema.

Historically, physicians have treated inflammation-related disorders with a regimen of NSAIDs such as, for example, aspirin and ibuprofen. Undesirably, however, some NSAIDs are known to cause gastrointestinal (GI) bleeding or ulcers in patients undergoing consistent long term regimens of NSAID therapy. Henry et al., *Lancet,* 1991, 337, 730. A reduction of unwanted side effects of common NSAIDs was made possible by the discovery that the two cyclooxygenases involved in the transformation of arachidonic acid as the first step in the prostaglandin synthesis pathway were cyclooxygenase-1 (COX-1) and cyclooxygenase-2 (COX-2).

Many common NSAIDs are now known to be inhibitors of both COX-1 and COX-2. Accordingly, when administered in sufficiently high levels, these NSAIDs not only alleviate the inflammatory consequences of COX-2 activity, but also inhibit the beneficial gastric maintenance activities of COX-1. Research into the area of arachidonic acid metabolism has resulted in the discovery of compounds that selectively inhibit the COX-2 enzyme to a greater extent than they inhibit COX-1. These COX-2 selective inhibitors are believed to offer advantages that include the capacity to prevent or reduce inflammation while avoiding harmful side effects associated with the inhibition of COX-1. Thus, COX-2 selective inhibitors have shown great promise for use in therapies, especially in therapies that require maintenance administration, such as for pain and inflammation control.

As described herein, the terms "cyclooxygenase-2 inhibitor" and "Cox-2 inhibitor", which can be used interchangeably herein, denote compounds which inhibit the cyclooxygenase-2 enzyme (COX-2) regardless of the degree of inhibition of the cyclooxygenase-1 enzyme (COX-1), and include pharmaceutically acceptable racemates, enantiomers, tautomers, salts, esters and prodrugs of those compounds. Thus, for purposes of the present disclosure, a compound is considered a COX-2 inhibitor although the compound inhibits COX-2 to an equal, greater, or lesser degree than it inhibits COX-1. COX-2 inhibitors herein therefore encompass many traditional non-selective NSAIDs.

COX-2 Selective Inhibitors

COX-2 inhibitors useful according to embodiments of the present disclosure are agents and compounds that selectively or preferentially inhibit COX-2 to a greater degree than they inhibit COX-1. Such agents and compounds are termed "COX-2 selective inhibitors" herein.

In practice, in a test for selectivity of a COX-2 selective inhibitor, the observed selectivity varies depending upon the conditions under which the test is performed and on the compound being tested. For example, selectivity of a COX-2 inhibitor can be measured as a ratio of the in vitro or in vivo $IC_{50}$ value for inhibition of COX-1, divided by the corresponding $IC_{50}$ value for inhibition of COX-2 (COX-1 $IC_{50}$/COX-2 $IC_{50}$). A COX-2 selective inhibitor herein is thus any inhibitor for which COX-1 $IC_{50}$/COX-2 $IC_{50}$ is greater than 1.

In various embodiments, this ratio is greater than about 2, greater than about 5, greater than about 10, greater than about 50, or greater than about 100.

In one embodiment, the invention provides a composition, comprising a combination of a 1,2-diphenylpyrrole derivative and an EGFR inhibitor wherein the ratio of selectivity of COX-2 over COX-1 inhibition is greater than about 1. In another embodiment, the invention provides a composition comprising a combination of a 1,2-diphenylpyrrole derivative and an EGFR inhibitor wherein the ratio of selectivity of COX-2 over COX-1 inhibition is greater than about 2. In a further embodiment, the invention provides a composition comprising combination of a 1,2-diphenylpyrrole derivative and an EGFR inhibitor wherein the ratio of selectivity of COX-2 over COX-1 inhibition is greater than about 5. In another embodiment, the invention provides a composition comprising a combination of a 1,2-diphenylpyrrole derivative and an EGFR inhibitor wherein the ratio of selectivity of COX-2 over COX-1 inhibition is greater than about 7.8. In yet a further embodiment, the invention provides a composition comprising a combination of a 1,2-diphenylpyrrole derivative and an EGFR inhibitor wherein the ratio of selectivity of COX-2 over COX-1 inhibition is greater than about 10. In another embodiment, the invention provides a composition comprising a combination of a 1,2-diphenylpyrrole derivative and an EGFR inhibitor wherein the ratio of selectivity of COX-2 over COX-1 inhibition is greater than about 20. In a further embodiment, the invention provides a composition comprising a combination of a 1,2-diphenylpyrrole derivative and an EGFR inhibitor wherein the ratio of selectivity of COX-2 over COX-1 inhibition is greater than about 50. In yet a further embodiment, the invention provides a composition comprising a combination of a 1,2-diphenylpyrrole derivative and an EGFR inhibitor wherein the ratio of selectivity of COX-2 over COX-1 inhibition is greater than about 100. In one embodiment, the invention provides a composition comprising a combination of a 1,2-diphenylpyrrole derivative and an EGFR inhibitor wherein 1-2-diphenylpyrrole derivative is 2-(4-ethoxyphenyl)-4-methyl-1-(4-sulfamoylphenyl)-pyrrole. In another embodiment, the invention provides a composition comprising a combination of a 1,2-diphenylpyrrole derivative and an EGFR inhibitor wherein the EGFR inhibitor is erlotinib. In a further embodiment, the invention provides a composition comprising a combination of a 1,2-diphenylpyrrole derivative and an EGFR inhibitor wherein the 1-2-diphenylpyrrole derivative is 2-(4-ethoxyphenyl)-4-methyl-1-(4-sulfamoylphenyl)-pyrrole and the EGFR inhibitor is erlotinib and wherein the ratio of selectivity of COX-2 over COX-1 inhibition is greater than about 1, about 2, about 5, about 7.8, about 10, about 20, about 50, and about 100.

In one embodiment, the invention provides a method for treating a tumor and/or tumor related disease comprising administering a combination of a 1,2-diphenylpyrrole derivative and an EGFR inhibitor wherein the ratio of selectivity of COX-2 over COX-1 inhibition is greater than about 1. In one embodiment, the invention provides a method for treating a tumor and/or tumor related disease comprising administering a combination of a 1,2-diphenylpyrrole derivative and an EGFR inhibitor wherein the ratio of selectivity of COX-2 over COX-1 inhibition is greater than about 2. In a further embodiment, the invention provides a method for treating a tumor and/or tumor related disease comprising administering a combination of a 1,2-diphenylpyrrole derivative and an EGFR inhibitor wherein the ratio of selectivity of COX-2 over COX-1 inhibition is greater than about 5. In yet a further embodiment, the invention provides a method for treating a tumor and/or tumor related disease comprising administering a combination of a 1,2-diphenylpyrrole derivative and an EGFR inhibitor wherein the ratio of selectivity of COX-2 over COX-1 inhibition is greater than about 10. In some embodiments, the invention provides methods for treating a tumor and/or tumor related disease comprising administering a combination of a 1,2-diphenylpyrrole derivative and an EGFR inhibitor wherein the ratio of selectivity of COX-2 over COX-1 inhibition is greater than about 20, than about 50, and about 100. In other embodiments, the invention provides methods for treating a tumor and/or tumor related disease comprising administering a combination of a 1,2-diphenylpyrrole derivative and an EGFR inhibitor wherein the 1-2-diphenylpyrrole derivative is 2-(4-ethoxyphenyl)-4-methyl-1-(4-sulfamoylphenyl)-pyrrole and the EGFR inhibitor is erlotinib wherein the ratio of selectivity of COX-2 over COX-1 inhibition is greater than about 1, about 2, about 5, about 7.8, about 10, about 20, about 50, and about 100.

As used herein, the term "$IC_{50}$" with respect to a COX-1 or COX-2 inhibitor refers to the concentration of a compound that is required to produce 50% inhibition of activity of COX-1 or COX-2. In one embodiment, 1,2-diphenylpyrrole derivatives useful in the present disclosure can have a COX-2 $IC_{50}$ of less than about 3 µM. In another embodiment, the 1,2-diphenylpyrrole derivative has a COX-2 $IC_{50}$ of less than about 2.8 µM. In yet another embodiment, the 1,2-diphenylpyrrole derivative has a COX-2 $IC_{50}$ of less than about 2 µM. In some embodiments, 1,2-diphenylpyrrole derivative useful in the present disclosure can have a COX-2 $IC_{50}$ of less than about 1 µM, less than about 0.5 µM, or less than about 0.2 µM. 1,2-diphenylpyrrole derivatives useful in the present disclosure can have a COX-1 $IC_{50}$ of greater than about 1 µM, for example greater than about 20 µM. In one embodiment, the invention provides a composition comprising a combination of a 1,2-diphenylpyrrole derivative and an EGFR inhibitor wherein the $IC_{50}$ is less than about 1 µM. In another embodiment, the invention provides a composition comprising a combination of a 1,2-diphenylpyrrole derivative and an EGFR inhibitor wherein the $IC_{50}$ is less than about 0.5 µM. In a further embodiment, the invention provides a composition comprising a combination of a 1,2-diphenylpyrrole derivative and an EGFR inhibitor wherein the $IC_{50}$ is less than about 0.2 µM. In one embodiment the 1,2-diphenylpyrrole derivative is 2-(4-ethoxyphenyl)-4-methyl-1-(4-sulfamoylphenyl)-pyrrole. In another embodiment the EGFR inhibitor is erlotinib. In a further embodiment the 1,2-diphenylpyrrole derivative is 2-(4-ethoxyphenyl)-4-methyl-1-(4-sulfamoylphenyl)-pyrrole and the EGFR inhibitor is erlotinib wherein the $IC_{50}$ is less than about 3 µM, about 2.8 µM, about 2 µM, about 1 µM, about 0.5 µM, and about 0.2 µM.

COX-2 inhibitors exhibiting a high degree of selectivity for COX-2 over COX-1 inhibition can indicate ability to reduce incidence of common NSAID-induced side effects. In one embodiment, the invention provides a composition comprising a combination of a 1,2-diphenylpyrrole derivative and an EGFR inhibitor wherein the NSAID-induced side effects are substantially diminished. For example, NSAID-induced side effects include, but are not limited to, nausea, vomiting, diarrhea, constipation, decreased appetite, rash, dizziness, headache, drowsiness, fluid retention, edema, kidney failure, liver failure, ulcers and prolonged bleeding after surgery. In another embodiment, the invention provides a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib and wherein the NSAID-induced side effects are substantially diminished.

A COX-2 selective inhibitor can be used in a form of a prodrug thereof. As described herein, a "COX-2 prodrug" is a compound that can be converted into an active COX-2 selective inhibitor by metabolic or simple chemical processes within the body of the subject. One example of a prodrug for a COX-2 selective inhibitor is parecoxib, for example in a form of a salt such as parecoxib sodium, which is a therapeutically effective prodrug of the tricyclic COX-2 selective inhibitor valdecoxib.

Overexpression of COX-2 and Cancer

The overexpression of COX-2 and also the upstream and downstream enzymes of the prostaglandin synthesis pathway has been demonstrated in multiple cancer types and some pre-neoplastic lesions. Direct interactions of prostaglandins with their receptors through autocrine or paracrine pathways to enhance cellular survival or stimulate angiogenesis have been proposed as molecular mechanisms underlying the pro-carcinogenic functions of COX enzymes. In this respect, pre-clinical studies suggest that COX-2 may be involved in the molecular pathogenesis of some types of lung cancer. Most of the studies point to its involvement in non-small cell lung cancer. Survival of patients with non-small cell lung cancer expressing high levels of COX-2 is markedly reduced. Treatment of humans with the selective COX-2 inhibitor celecoxib augments the antitumor effects of chemotherapy in patients with non-small cell lung cancer. Studies indicate that prostaglandins synthesized by cyclooxygenase play a critical role in the initiation and promotion of cancer. Aberrant COX-2 expression was reported in colorectal carcinomas and adenomas, and has been detected in various human cancers, including those of the breast. Moreover, COX-2 is overexpressed in neoplastic lesions of the colon, breast, lung, prostate, esophagus, pancreas, intestine, cervix, ovaries, urinary bladder and head and neck (see Table 1 below).

TABLE 1

COX-2 Expression in Tumors

| Tumor Type | % Tissue expressing COX-2 |
| --- | --- |
| Colorectal Cancer | 70-95 |
| Non-small Cell Lung Cancer | 70-90 |
| Gastric Cancer | 45-75 |
| Pancreatic Cancer | 40-80 |
| Glioblastoma Multiforme | 40-70 |
| Bladder Cancer | 50-60 |
| Esophageal Cancer | 50-60 |
| Breast Cancer | 40-50 |
| Ovarian Cancer | 40-60 |
| Prostate Cancer | 40-60 |

COX-2 overexpression in murine mammary glands is sufficient to cause tumor formation. In several in vitro and animal models, COX-2 inhibitors have inhibited tumor growth and metastasis.

In addition to cancers per se, COX-2 is also expressed in the angiogenic vasculature within and adjacent to hyperplastic and neoplastic lesions indicating that COX-2 plays a role in angiogenesis. In both the mouse and rat, COX-2 inhibitors markedly inhibited bFGF-induces neovascularization. The utility of COX-2 inhibitors as chemopreventive, antiangiogenic and chemotherapeutic agents is described in the literature. Koki et al., *Exp. Opin., Invest. Drugs,* 1999, 8(10) 1623-38.

COX-2 has been shown to regulate some embodiments of tumor-associated angiogenesis. Angiogenesis is an attractive therapeutic target because it is a multi-step process that occurs in a specific sequence, thus providing several possible targets for drug action. Angiogenesis is important in two stages of tumor metastasis. The first stage where angiogenesis stimulation is important is in the vascularization of the tumor which allows the tumor cells to enter the blood stream and to circulate throughout the body. After the tumor cells have left the primary site and have settled into the secondary, metastasis site, angiogenesis must occur before the new tumor can grow and expand. Therefore, prevention of angiogenesis could lead to the prevention of metastasis of tumors and possibly contain the neoplastic growth at the primary site. Examples of agents that interfere with several of these steps include, angiostatin, endostatin, interferon alpha and COX-2 selective inhibitors that prevent the growth of cells that form new blood vessels; and protein-based compounds that simultaneously interfere with several of these targets.

Additionally, several studies have suggested that COX-2 expression is associated with parameters of aggressive breast cancer, including large tumor size, positive axillary lymph node metastases, and HER2-positive tumor status. Studies of mammary tumors in mice and rats have indicated that moderate to high COX-2 expression is related to the genesis of mammary tumors that are sensitive to treatment with nonspecific and specific COX-2 inhibitors. Further studies have shown that increased amounts of prostaglandins and COX-2 are commonly found in a wide range of premalignant tissues and malignant tumors including cervical dysplasia and cancer. Elevated prostaglandin and COX-2 levels substantially contribute to carcinogenesis by inhibiting apoptosis and stimulating angiogenesis. Tsujii and DuBois, *Cell,* 1995, 83, 493-501.

Further, COX-2 is also highly expressed in prostate cancer, particularly in the epithelial cell of high-grade prostatic intraepithelial neoplasia and cancer. It was shown that treatment of human prostate cancer cell lines with a selective COX-2 inhibitor induces apoptosis both in vitro and in vivo. The in vivo results also indicate that the COX-2 inhibitor decreases tumor microvessel density and angiogenesis. COX-2 inhibitors can prevent the hypnoxic upregulation of a potent angiogenic factor, vascular endothelial growth factor.

Overexpression of COX-2 has been documented in several premalignant and malignant tissues. Subbaramaiah et al., *Trends Pharmacol. Sci.,* 2003, 24, 96-102. Without wishing to be bound by any particular theory, this increase in expression is thought to be a product of stimulation of PKC signaling, which stimulates activity of MAPK, enhancing transcription of COX-2 by nuclear factors. Additionally, enhanced stability of COX-2 mRNA transcripts in cancer cells due to augmented binding of the RNA-binding protein HuR, as well as activation of extracellular signal related kinase 1 and 2 (ERK 1 and 2) and p38, is thought to contribute to increased expression of COX-2.

These results indicate that COX-2 inhibitors may serve as effective chemopreventive and therapeutic agents in cancer of the prostate.

COX-2 Selective Inhibitors

It has recently been found that the use of nonsteroidal anti-inflammatory drugs (NSAIDs) has been associated with the prevention and treatment of several types of cancer. Thun et al., *J. National Cancer Inst.,* 2002, 94(4), 252-66. COX-2 inhibitors have been utilized for the treatment of cancer and for the treatment of tumors. For example, celecoxib, a COX-2 selective inhibitor, exerted a potent inhibition of fibroblast growth factor-induced corneal angiogenesis in rats. Masferrer et al., *Proc. Am. Assoc. Cancer Research,* 1999, 40, 396. Other COX-2 inhibitors have been described for the treatment of cancer, tumors and neoplasia. FR 27 71 005 describes compositions containing a COX-2 inhibitor and N-methyl-d- aspartate (NMDA) antagonist used to treat cancer and other diseases. Further, WO 99/18960 describes a combination comprising a COX-2 inhibitor that can be used to treat colorectal and breast cancer. Additionally, WO 97/36497 describes a combination comprising a COX-2 inhibitor and a 5-lipoxygenase inhibitor useful in treating cancer.

1,2-Diphenylpyrrole Derivatives 1,2-Diphenylpyrrole derivatives and pharmaceutically acceptable salts, solvates, or prodrugs are known to have analgesic and antiphlogistic properties. Further, they have been shown to act as COX-2 selective inhibitors and are thus effective for the prophylaxis and therapy of diseases mediated by COX-2 and/or inflammatory cytokines. In addition, 1,2-diphenylpyrrole derivatives have been shown to treat diseases involving or resulting from the resorption of bone, such as osteoporosis, rheumatoid arthritis and osteoarthritis.

These types of analgesics, anti-inflammatory agents and/or antipyretics exhibit effects not only on inflammatory diseases, such as pain, pyrexia, and edema, but also on chronic inflammatory diseases, such as chronic rheumatoid arthritis and osteoarthritis, allergic inflammatory diseases, asthma, sepsis, psoriasis, various autoimmune diseases, systemic lupus erythematosus, juvenile onset diabetes, autoimmune intestinal diseases (such as ulcerative colitis, Crohn's disease), viral infection, and glomerulonephritis.

1,2-Diphenylpyrrole derivatives described herein have the general formula:

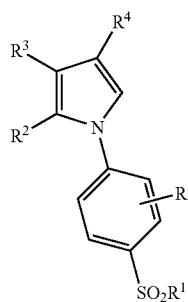

wherein:
R is a hydrogen atom, a halogen atom or an alkyl group having from 1 to 6 carbon atoms;
$R^1$ is an alkyl group having from 1 to 6 carbon atoms or an amino group;
$R^2$ is a phenyl group which is unsubstituted or is substituted by at least one substituent selected from the group consisting of substituents α and substituents β;
$R^3$ is a hydrogen atom, a halogen atom or an alkyl group which has from 1 to 6 carbon atoms and which is unsubstituted or is substituted by at least one substituent selected from the group consisting of a hydroxy group, a halogen atom, an alkoxy group having from 1 to 6 carbon atoms and an alkylthio group having from 1 to 6 carbon atoms;
$R^4$ is a hydrogen atom; an alkyl group which has from 1 to 6 carbon atoms and which is unsubstituted or is substituted by at least one substituent selected from the group consisting of a hydroxy group, a halogen atom, an alkoxy group having from 1 to 6 carbon atoms and an alkylthio group having from 1 to 6 carbon atoms; a cycloalkyl group having from 3 to 8 carbon atoms, an aryl group; or an aralkyl group; said aryl group having from 6 to 14 ring carbon atoms in a carbocyclic ring and are unsubstituted or are substituted by at least one substituent selected from the group consisting of substituents α and substituents β; said aralkyl group are an alkyl group having from 1 to 6 carbon atoms and which are substituted by at least one aryl group as defined above;
said substituents α are selected from the group consisting of a hydroxy group, a halogen atom, an alkoxy group having from 1 to 6 carbon atoms and an alkylthio group having from 1 to 6 carbon atoms;
said substituents β are selected from the group consisting of an alkyl group which has from 1 to 6 carbon atoms and which is unsubstituted or are substituted by at least one substituent selected from the group consisting of a hydroxy group, a halogen atom, an alkoxy group having from 1 to 6 carbon atoms and an alkylthio group having from 1 to 6 carbon atoms; an alkanoyloxy group having from 1 to 6 carbon atoms; a mercapto group; an alkanoylthio group having from 1 to 6 carbon atoms; an alkylsulfinyl group having from 1 to 6 carbon atoms; a cycloalkloxy group having from 3 to 8 carbon atoms; a haloalkoxy group having from 1 to 6 carbon atoms; and an alkylenedioxy group having from 1 to 6 carbon atoms; or a pharmaceutically acceptable salt, solvate, or prodrug.

In one embodiment, the invention provides a 1,2-diphenylpyrrole derivative having the formula:

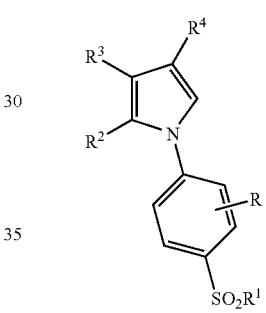

wherein:
R is a hydrogen atom, a halogen atom or an alkyl group having from 1 to 4 carbon atoms;
$R^1$ is a methyl group or an amino group;
$R^2$ is an unsubstituted phenyl group or a phenyl group which is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and which is substituted by at least one substituent selected from the group consisting of a halogen atom, an alkoxy group having from 1 to 4 carbon atoms and an alkylthio group having from 1 to 4 carbon atoms; a haloalkoxy group having from 1 to 4 carbon atoms; and an alkylenedioxy group having from 1 to 4 carbon atoms;
$R^3$ is a hydrogen atom, a halogen atom, an unsubstituted alkyl group having from 1 to 4 carbon atoms or a substituted alkyl group having from 1 to 4 carbon atoms and substituted by at least one substituent selected from the group consisting of a halogen atom, an alkoxy group having from 1 to 4 carbon atoms and an alkylthio group having from 1 to 4 carbon atoms;
$R^4$ is a hydrogen atom; an unsubstituted alkyl group having from 1 to 4 carbon atoms; a substituted alkyl group having from 1 to 4 carbon atoms and substituted by at least one substituent selected from the group consisting of a hydroxy group, a halogen atom, an alkoxy group having from 1 to 4 carbon atoms and an alkylthio group having from 1 to carbon atoms; a cycloalkyl group having from 3 to 6 carbon atoms; an aryl group which has from 6 to 10 ring carbon atoms and which is unsubstituted or is substituted by at least one substituent selected from the group consisting of a halogen atom; an alkoxy group having from 1 to 4 carbon atoms; an alkylthio group having from 1 to 4 carbon atoms; an unsubstituted alkyl group having from 1 to 4 carbon atoms; an alkyl group having from 1 to 4 carbon atoms and substituted by at least one substituent selected from the group consisting of a hydroxy group, a halogen atom, an alkoxy group having from 1 to 4 carbon atoms and an alkylthio group having from 1 to 4 carbon atoms; and a cycloalkyloxy group having from 3 to 7 carbon atoms; an aralkyl group having from 1 to 4 carbon atoms in the alkyl part and containing at least one said aryl group; or a pharmaceutically acceptable salt, solvate, or prodrug.

In one embodiment, the invention provides a 1,2-diphenylpyrrole derivative wherein:

R is a hydrogen atom;

$R^1$ is an amino group;

$R^2$ is an unsubstituted phenyl group or a phenyl group which is substituted by at least one substituent selected from the group consisting of a halogen atom, an alkoxy group having from 1 to 4 carbon atoms, an alkylthio group having from 1 to 4 carbon atoms, an alkyl group having from 1 to 4 carbon atoms, a haloalkyl group having from 1 to 4 carbon atoms, a haloalkoxy group having from 1 to 4 carbon atoms and a alkylenedioxy group having from 1 to 4 carbon atoms;

$R^3$ is a hydrogen atom, a halogen atom, an alkyl group having from 1 to 4 carbon atoms or a haloalkyl group having from 1 to 4 carbon atoms;

$R^4$ is a hydrogen atom; an unsubstituted alkyl group having from 1 to 4 carbon atoms; a substituted alkyl group having from 1 to 4 carbon atoms and substituted by at least one substituent selected from the group consisting of a hydroxy group and an alkoxy group having from 1 to 4 carbon atoms; a cycloalkyl group having from 3 to 6 carbon atoms; an aryl group which has from 6 to 10 ring carbon atoms and which is unsubstituted or is substituted by at least one substituent selected from the group consisting of a hydroxy group; a halogen atom; an alkoxy group having from 1 to 4 carbon atoms; an unsubstituted alkyl group having from 1 to 4 carbon atoms; an alkyl group having from 1 to 4 carbon atoms and which is unsubstituted or substituted by at least one halogen atom; and a cycloalkyloxy group having from 3 to 7 carbon atoms; and an aralkyl group having from 1 to 4 carbon atoms in the alkyl part and containing at least one said aryl group; or a pharmaceutically acceptable salt, solvate, or prodrug.

In one embodiment, R is a hydrogen atom. In another embodiment, R is a fluorine atom. In a further embodiment, R is a chlorine atom. In yet a further embodiment, R is a methyl group.

In one embodiment, $R^1$ is a methyl group. In another embodiment, $R^1$ is an amino group.

In one embodiment, $R^2$ is a phenyl group.

In one embodiment, $R^3$ is a hydrogen atom. In another embodiment, $R^3$ is a halogen atom.

In one embodiment, $R^4$ is a hydrogen atom.

The term "aryl" refers to a carbocyclic aromatic hydrocarbon group having from 6 to 14 carbon atoms in one or more aromatic rings or such a group which is fused to a cycloalkyl group having from 3 to 10 carbon atoms, and the group is unsubstituted or it is substituted by at least one substituent selected from the group consisting of hydroxy groups, halogen atoms, lower alkoxy groups, lower alkylthio groups, lower alkyl groups, alkanoyloxy groups, mercapto groups, alknoylthio groups, lower alkylsulfinyl groups, lower alkyl groups having at least one substituent selected from the group consisting of cycloalkloxy groups, lower haloalkoxy groups, and lower alkylenedioxy groups.

In some embodiments, the 1,2-diphenylpyrrole derivative is selected from the group consisting of compounds 2-1-2-213 of Table 2 as disclosed in U.S. Pat. No. 6,887,893, which is herein incorporated in its entirety by reference.

In one embodiment, the 1,2-diphenylpyrrole derivative is selected from the group consisting of: 4-methyl-2-(4-methylphenyl)-1-(4-sulfamoylphenyl)pyrrole; 2-(4-methoxyphenyl)-4-methyl-1-(4-sulfamoylphenyl)pyrrole; 2-(4-chlorophenyl)-4-methyl-1-(4-sulfamoylphenyl)pyrrole; 4-methyl-2-(4-methylthiophenyl)-1-(4-sulfamoylphenyl)pyrrole; 2-(4-ethoxyphenyl)-4-methyl-1-(4-sulfamoylphenyl)pyrrole; 2-(4-methoxy-3-methylphenyl)-4-methyl-1-(4-sulfamoylphenyl)pyrrole; 2-(3-fluoro-4-methoxyphenyl)-4-methyl-1-(4-sulfamoylphenyl)pyrrole; 2-(3,4-dimethylphenyl)-4-methyl-1-(4-sulfamoylphenyl)pyrrole; 4-methyl-1-(4-methylthiophenyl)-2-(4-sulfamoylphenyl)pyrrole; 1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole. In another embodiment, the invention provides a method wherein the 1,2-diphenylpyrrole derivative is 2-(4-ethoxyphenyl)-4-methyl-1-(4-sulfamoylphenyl)-pyrrole.

In another embodiment, the 1,2-diphenylpyrrole derivative is 2-(4-ethoxyphenyl)-4-methyl-1-(4-sulfamoylphenyl)-pyrrole.

The methods for synthesizing 1,2-diphenylpyrrole derivatives, illustrated herein, are described in the Examples section and in U.S. RE39,420, which is incorporated herein by reference in its entirety.

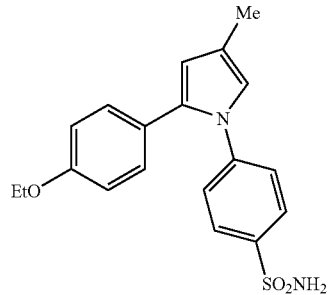

2-(4-ethoxyphenyl)-4-methyl-1-(4-sulfamoylphenyl)-pyrrole 2-(4-Ethoxyphenyl)-4-methyl-1-(4-sulfamoylphenyl)-pyrrole has alternative chemical names, including 4-[2-(4-ethoxyphenyl)-4-methyl-1H-pyrrol-1-yl benzenesulfonamide, 4-[2-(4-ethoxyphenyl)-4-methyl-1H-pyrrol-1-yl] benzenesulfonamide, TG01, CS-706 and apricoxib. It has a molecular formula of $C_{19}H_{20}N_2O_3S$, a molecular weight of 356.4 and the CAS registry number is 197904-84-0.

Receptor Tyrosine Kinases

Protein tyrosine kinases are a class of enzymes that catalyze the transfer of a phosphate group from ATP or GTP to the tyrosine residue located on protein substrates. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. Under certain conditions, however, as a result of either mutation or overexpression, these receptors can become deregulated; the result of which is uncontrolled cell proliferation which can lead to tumor growth and ultimately to the disease known as cancer. Wilks, *Adv. Cancer Res.*, 1993, 60, 43. Among the growth factor receptor kinases and their proto-oncogenes that have been identified and which are targets of the combinations presented herein are the epidermal growth factor receptor kinase (EGFR kinase, the protein product of the erbB oncogene), and the product produced by the erbB-2 (also referred to as the neu or HER2) oncogene. Since the phosphorylation event is a necessary signal for cell division to occur and since overexpressed or mutated kinases have been associated with cancer, an inhibitor of this event, a protein tyrosine inhibitor, will have therapeutic value for the treatment of cancer and other diseases characterized by uncontrolled or abnormal cell growth. For example, overexpression of the receptor kinase product of the erbB-2 oncogene has been associated with human breast and ovarian cancers. Slamon et. al., *Science*, 1989, 244, 707. Deregulation of EGFR kinase has been associated with epidermoid tumors and tumors involving other major organs. Because of the importance of the role played by deregulated receptor kinases in the pathogenesis of cancer, many recent studies have dealt with the development of specific PTK inhibitors as potential anti-cancer therapeutic agents.

Receptor tyrosine kinases span the cell membrane and possess an extracellular binding domain for growth factors such as epidermal growth factor (EGF), a transmembrane domain, and an intracellular portion which functions as a kinase to phosphorylate specific tyrosine kinase residues in proteins and hence to influence cell proliferation. The EGF receptor tyrosine kinase family has four members: EGFR (HER1, erbB1); HER2 (c-erbB2, erbB2, neu); HER3 (erbB3); and HER4 (erbB4). The ErbB receptors generally transduce signals through two pathways. It is known that such kinases are frequently and aberrantly expressed in common human cancers such as breast cancer, gastrointestinal cancer of colon, rectum or stomach, leukemia, and ovarian, bronchial or pancreatic cancer. As discussed previously, epidermal growth factor receptor (EGFR), is mutated and/or overexpressed in many human cancers such as brain, lung, squamous cell, bladder, gastric, breast, head and neck, oesophageal, gynecological and thyroid tumors.

Epidermal Growth Factor Receptors

Control of cell growth is regulated by the interaction of soluble growth factors and cell membrane receptors. The first step in the mitogenic stimulation of epidermal cells is the specific binding of epidermal growth factor (EGF) to a membrane glycoprotein known as the epidermal growth factor receptor (EGFR). The EGFR is composed of 1,186 amino acids which are divided into an extracellular portion of 621 residues and a cytoplasmic portion of 542 residues connected by a single hydrophobic transmembrane segment of 23 residues. Ullrich et al., *Nature*, 1986, vol. 309, 418-25. The external portion of the EGFR can be subdivided into four domains. Recently, it has been demonstrated that domain III, residues 333 to 460 which is flanked by two cysteine domains is likely to contain the EGFR binding site of the receptor. Lax et al., *Mol. And Cell Biol.*, 1988, vol. 8, 1831-34. The binding of EGF to domain III leads to the initiation of pleiotropic responses leading to DNA synthesis and cell proliferation.

EGFR has also been found in various types of human tumor cells and that those cells overexpress EGFR. For example, the cancerous cells of bladder tumors have been shown to have a relatively large population of EGF receptors. Neal et al., *Lancet*, 1985, vol. 1, 366-67. Breast cancer cells exhibit a positive correlation between EGFR density and tumor size and a negative correlation with the extent of differentiation. Sainsbury et al., *Lancet*, 1985, vol. 1, 364-66. The tumorigenicity of a series of human vulval epidermoid carcinoma (A431) clonal variants implanted into athymic mice having different levels of EGFR was found to correlate directly with the level of expression of the EGF receptor. Santon et al., *Cancer Res.*, 1986, vol. 46, 4700-01. Thus, it has been proposed that overexpression of EGFRs play a role in the origin or tumorigenesis of cancer cells.

EGFR and COX Pathways

Figure 2:
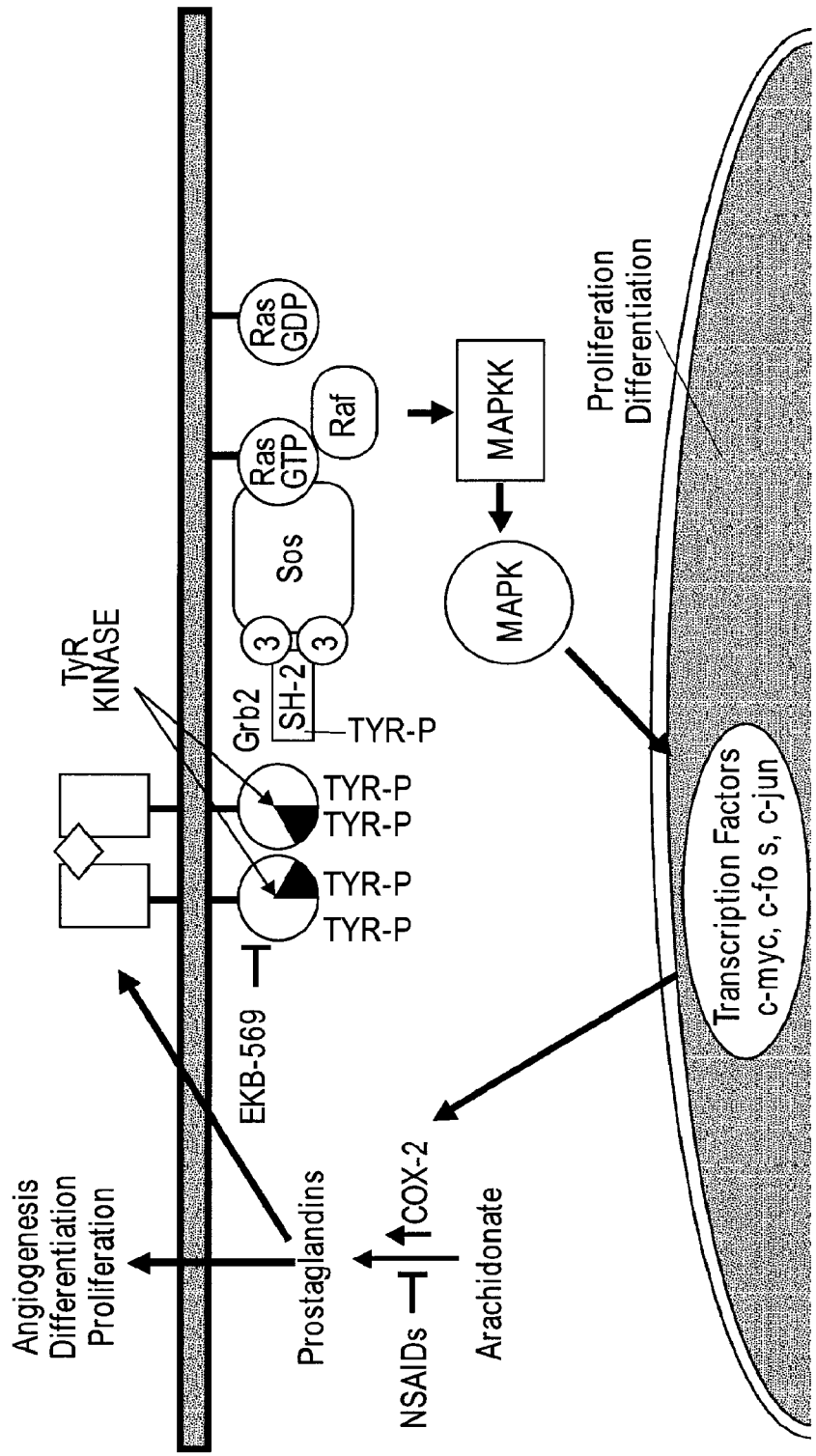
FIG. 2 provides an illustration of the interactions between the EGFR and COX pathways.

The relationship between the EGFR and COX pathways, to date, has not yet been fully elucidated. It has been submitted, however, that induction of COX-2 results in the production of increased levels of prostaglandins which then stimulate angiogenesis, cell proliferation and cell differentiation in an autocrine and/or paracrine manner. As described above, NSAIDs inhibit this process. Prostaglandins promote angiogenesis, along with cellular differention and proliferation. They also activate signaling through the EGFR. EGFR activation leads to phosphorylation on tyrosine residues by the receptor's tyrosine kinase domain, initiating a signaling pathway that includes the molecules Grb-2, SOS, the small G protein Raf. Raf activates Mitogen-Activated Protein Kinase Kinase (MAPKK) and group of nuclear transcription factors (c-myc, c-fos, c-jun); (see FIG. 2). These factors initiate transcription of genes involved in the regulation of cell proliferation and differentiation. Additionally, these factors induce transcription of the COX-2. These effects may significantly amplify the original EGFR mediated signal and lead to pro-neoplastic effects. Inhibiting both signaling pathways could lead to a significant anti-neoplastic effect.

Studies have provided support that EGFR induces COX-2 in intestinal epithelial cells and anti-HER2 antibodies can inhibit COX-2 expression in colorectal cancer cells. In addition, overexpression of COX-1 or COX-2 in colon carcinoma cells has been shown to increase EGFR expression. Thus, COX and EGFR levels appear to be linked in a positive feedback cycle during colon cancer development. While the exact mechanism by which dysregulated EGF signaling promotes colon carcinogenesis is not clearly understood, it has been submitted that EGFR activation in a variety of cell types results in stimulation of cell proliferation and alterations in cell motility and/or adhesion to extra-cellular matrix. Studies have suggested that COX can positively influence tumor growth by promoting tumor associated angiogenesis.

It has also recently been proposed that the activation and overexpression of COX-2 in adenomatous polyps is due to activation of the EGFR. EGFR stimulation by one of its ligands, amphiregulin (AR), induces the nuclear targeting of COX-2, release of prostaglandins and subsequent mitogenesis, in polarized colonic epithelial cells. COX-2 inhibitors have been shown to prevent this series of events.

EGFR Inhibitors

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma which expresses EGFR but is without effect on the growth of another carcinoma which does not express the EGFR.

Various other compounds, such as styrene derivatives, have also been shown to possess tyrosine kinase inhibitory properties. Others have disclosed that certain quinazoline derivatives possess anti-cancer properties which result from their tyrosine inhibitory properties.

As described herein, an "EGFR inhibitor" is a molecule which inhibits the kinase domain of the epidermal growth factor receptor. Compounds which are EGFR inhibitors can readily be identified by one skilled in the art using methods such as, for example, standard pharmacological test procedures which measure the inhibition of the phosphorylation of the tyrosine residue of a peptide substrate catalyzed by EGFR. Briefly, the peptide substrate (RR—SRC) has the sequence arg-arg-leu-ile-glu-asp-ala-glu-tyr-ala-ala-arg-gly. The enzyme is obtained as a membrane extract of A431 cells (American Type Culture Collection, Rockville, Md.). A431 cells are grown in T175 flasks to 80% confluency. The cells are washed twice with phosphate buffered saline (PBS) without $Ca^{2+}$. Flasks are rotated for 1.5 hours in 20 ml PBS with 1.0 mM ethylenediaminetetraacetic acid (EDTA) at room temperature and centrifuged at 600 g for 10 minutes. The cells are solubilized in 1 ml per $5 \times 10^6$ cells of cold lysis buffer {10 mM 4-(2-hydroxyethyl)-1-piperazineethanesulfonic acid (HEPES), pH 7.6, 10 mM NaCl, 2 mM EDTA, 1 mM phenylmethylsulfonyl-fluoride (PMSF), 10 mg/ml aprotinin, 10 mg/ml leupeptin, 0.1 mM sodium orthovanadate} in a Dounce homogenizer with 10 strokes on ice. The lysate is centrifuged at 600 g for 10 minutes first to clear cell debris and the supernatant further centrifuged at 100,000 g for 30 min at 4.degree.C. The membrane pellet is suspended in 1.5 ml HNG buffer (50 mM HEPES, pH 7.6, 125 mM NaCl, 10% glycerol). The membrane extract is divided into aliquots, immediately frozen in liquid nitrogen and stored at −70° C.

Compositions to be evaluated are made into 10 mg/ml stock solutions in 100% dimethylsulfoxide (DMSO). Stock solutions are diluted to 500 mM with buffer (30 mM Hepes pH 7.4) and then serially diluted to the desired concentration. An aliquot of the A431 membrane extract (10 mg/ml) is diluted in 30 mM HEPES (pH 7.4) to give a protein concentration of 50 µg/ml. To 4 µl of enzyme preparation, EGF (1 µl at 12 µg/ml) is added and incubated for 10 min on ice followed by 4 µl of the test compound or buffer; this mix is incubated on ice for 30 min. To this is added the $^{33}$P-ATP (10 mCi/ml) diluted 1:10 in assay buffer along with the substrate peptide at a concentration of 0.5 mM (control reactions get no test compound) and the reaction is allowed to proceed for 30 min at 30° C. The reaction is stopped with 10% TCA and left on ice for at least 10 min after which tubes are microcentrifuged at full speed for 15 min. A portion of the supernatants are then spotted on P81 phosphocellulose discs and washed twice in 1% acetic acid then water for 5 min each followed by scintillation counting. The results obtained can be expressed as an $IC_{50}$. The $IC_{50}$ is the concentration of test compound needed to reduce the total amount of phosphorylated substrate by 50%. The % inhibition of the test compound is determined for at least three different concentrations and the $IC_{50}$ value is evaluated from the dose response curve. The % inhibition is evaluated with the following formula:

$$\% \text{ inhibition} = 100 - [CPM(\text{drug})/CPM(\text{control})] \times 100$$

where CPM(drug) is in units of counts per minute and is a number expressing the amount of radiolabeled ATP (g-$^{33}$P) incorporated onto the RR—SRC peptide substrate by the enzyme after 30 minutes at 30° C. in the presence of test compound as measured by liquid scintillation counting. CPM (control) is in units of counts per minute and is a number expressing the amount of radiolabeled ATP (g-$^{33}$P) incorporated into the RR—SRC peptide substrate by the enzyme after 30 minutes at 30° C. in the absence of test compound as measured by liquid scintillation counting. The CPM values are corrected for the background counts produced by ATP in the absence of the enzymatic reaction. Compounds having an $IC_{50}$ of about 200 nM or less are considered to be significantly active EGFR inhibitors.

The identification of EGFR as an oncogene has led to the development of anticancer therapeutics directed against EGFR, including gefitinib and cetuximab for colon cancer. Cetuximab is an example of a monoclonal antibody inhibitor, while gefitinib is a small molecule inhibitor.

Monoclonal Antibodies

The monoclonal antibodies block the extracellular ligand binding domain. With the binding site blocked, signal molecules can no longer attach there and activate the tyrosine kinase.

Cetuximab is a chimeric monoclonal antibody generated from fusion of the variable region of the murine anti-EGFR monoclonal antibody M225 and the human IgG1 constant region. The resulting antibody retains high affinity and specificity to EGFR and reduces immunogenicity. Preclinical studies have demonstrated that cetuximab effectively inhibits the proliferation of a variety of EGFR-expressing cancer cells in vitro and that it inhibits tumor growth in xenograft models. In an orthotopic pancreatic cancer model, cetuximab significantly suppressed the growth of orthotopically implanted pancreatic tumors, and this effect was enhanced by the addition of gemcitabine. Histologic analysis of tumor specimens revealed that cetuximab induced apoptosis and suppressed proliferation of tumor cells. Interestingly, cetuximab also induced apoptosis of endothelial cells, which are not believed to be direct targets of EGFR inhibition. Moreover, an antiangiogenic effect, characterized by decreased microvascular densities associated with reduced expression of tumor-related VEGF and interleukin-8, was observed. These data suggest that, in addition to direct antiproliferative activity, antiangiogenic activity contributes significantly to the antitumor effect of EGFR inhibitors.

Panitumumab (ABX-EGF) is a fully human monoclonal antibody specific to EGFR and is produced by immunization of transgenic mice, that are able to produce human immunoglobulin light and heavy chains. Following immunization, a specific clone of B cells that produced the antibody against EGFR are selected and immortalized for the generation of the antibody.

Effective anti-EGFR monoclonal antibodies compete with endogenous ligands, primarily EGF and transforming growth factor a for receptor ligand-binding sites. Binding to EGFR blocks critical signaling pathways and interferes with the growth of tumors expressing EGFR. Anti-EGFR monoclonal antibodies that are currently under study include EMD 55900 and ICR 62.

Small Molecules

Another method is using small molecules to inhibit the EGFR tyrosine kinase, which is on the cytoplasmic side of the receptor. Without kinase activity, EGFR is unable to activate itself, which is a prerequisite for binding of downstream adaptor proteins. Ostensibly by halting the signaling cascade in cells that rely on this pathway for growth, tumor proliferation and migration is diminished.

Gefitinib is currently only indicated for the treatment of locally advanced or metastatic non-small cell lung cancer (NSCLC) in patients who have previously received chemotherapy. While gefitinib has yet to be proven to be effective in other cancers, there is potential for its use in the treatment of other cancers where EGFR overexpression is involved.

Erlotinib

N-(3-ethynylphenyl)-6,7-bis(2-methoxyethoxy)quinazolin-4-amine, also known as erlotinib (Tarceva®), is currently being used to help treat advanced non-small cell lung cancer, and in combination with gemcitabine in the treatment for advanced metastatic pancreatic cancer. U.S. Pat. No. 5,747, 498 describes the preparation of erlotinib and other chemically-related compounds. Additionally, U.S. Pat. No. 6,900,221 describes the use of a stable polymorph of erlotinib as an inhibitor of the erbB family of oncogenic and protoncogenic protein kinases such as EGFR. Also, the patent illustrates methods for the treatment of non-small cell lung cancer, pediatric malignancies, cervical and other tumors caused or promoted by human papilloma virus (HPV), melanoma, Barrett's esophagus (pre-malignant syndrome), adrenal and skin cancers and auto immune, neoplastic cutaneous diseases and atherosclerosis.

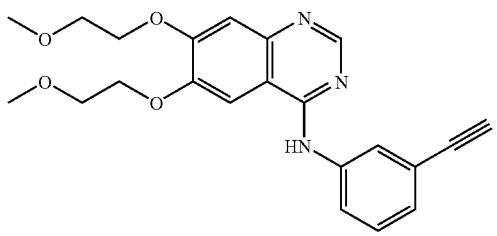

N-(3-ethynylphenyl)-6,7-bis(2-methoxyethoxy) quinazolin-4-amine

Gemcitabine

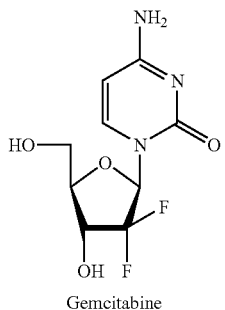

Gemcitabine

Gemcitabine is a nucleoside analog that exhibits antitumor activity. The chemical name for gemcitabine is β-2'-deoxy-2',2'-difluorocytidine and is administered as the hydrochloride salt. The cytotoxic effect of gemcitabine is attributed to two actions. First, gemcitabine diphosphate inhibits ribonucleotide reductase causing a reduction in deoxynucleotides available for DNA synthesis. Second, gemcitabine triphosphate competes with dCTP for incorporation into DNA. The two actions working in combination lead to high levels of gemcitabine nucleotide incorporation into growing DNA chains. This leads to inhibition of further DNA synthesis and chain termination.

Gemcitabine is indicated for use in the treatment of ovarian, breast, NSCL and pancreatic cancer. Gemcitabine hydrochloride is administered as an intravenous infusion of a 1000 mg/m$^2$ dose over 30 minutes once a week for up to 7 weeks. This is followed by one week of rest and then subsequent cycles of weekly infusions for 3 weeks of a 4 week cycle. Complete details are provided in the prescribing instructions for gemcitabine, which is included by reference in its entirety.

In one embodiment the invention provides a composition comprising a combination of a COX-2 selective inhibitor and an EGFR inhibitor disclosed herein for the treatment and prevention of cancer, tumors, and tumor-related disorders, and neoplastic disease states. In one embodiment, the EGFR inhibitor is a small molecule compound or an antibody.

In one embodiment, the EGFR inhibitor is selected from gefitinib, cetuximab, and erlotinib. In another embodiment, the EGFR inhibitor is erlotinib.

In another embodiment the small molecule compound is selected from the group consisting of: ZM-254530, BIBX-1382, reveromycin A, gefitinib, CGP-57148, CGP-59326, 4-(m-chloro)-5,6-dimethyl-7H-pyrrolo[2,3-d]pyrimidine, tyrphostin, PKI-166, PD 153035, EKB-569, and 4-(phenylamino)quinazolines, or their pharmaceutically acceptable salts, solvates, or prodrugs. In another embodiment, the small molecule is selected from the compounds disclosed in PCT/U.S.04/027574 which is herein incorporated by reference in its entirety.

In another embodiment, the antibody is selected from the group consisting of: EGF receptor antibody, MR1scFvPE38 KDEL MDX-447, MDX-210, MD-72000, MDX-260, wayne anti-EGFR Mabs, anti-EGFr Mab, anti-EGFr MAb, Genen anti-EGFR Mab, MAb DC-101, trastuzumab, anti-VEGF monoclonal, anti-EGFR-DM1 Ab, MAb 4D5, BAB-447, EMD-55900, EMD-6200, -82633, anti-EGFR Mab, MAb 4D5, cetuximab, anti-EGFr MAb, anti-flk-1, CCX, CCZ, anti-flk-1, AG-514, AG-568, nti-EGFR-DM1 Ab, MDX-447, TgDCC-E1A, of: muellerian-inhibiting hormone, TNP-470, tecogalan sodium, C C225, matuzumab, panitumumab, DWP408, and RC-394011. In another embodiment are provided compositions wherein the EGFR inhibitor is selected from the inhibitors disclosed in PCT/U.S.04/027574 which is herein incorporated by reference in its entirety.

In a further embodiment the EGFR inhibitor is selected from the group consisting EGF receptor antisense, PI-88, oligonucleotide, bromelain molecules, amphiregulin, EGF fusion toxin, EGF fusion protein, Amphiregulin hbEGF-toxin, hbEGF-toxin, and EGF fusion protein.

As described herein "a selective EGFR inhibitory effect" is meant that the composition comprising a combination of a 1,2-diphenylpyrrole derivative with erlotinib displays selective inhibition against EGFR than other kinases. In some embodiments, combinations presently disclosed display selective inhibition against EGFR kinase than against other tyrosine kinases such as other erbBRs such as erbB2. For example in one embodiment, the invention provides a composition comprising a combination of a 1,2-diphenylpyrrole derivative with erlotinib is at least 5 times or at least 10 times selective against EGFR than it is against erbB2, as determined from the relative $IC_{50}$ values in suitable assays (for example by comparing the $IC_{50}$ value from the KB cell assay with the $IC_{50}$ value from the Clone 24 phospho-erbB2 cell assay for a given composition as described above). In another embodiment, the invention provides a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib wherein the combination is at least 5 times or at least 10 times selective against EGFR than it is against erbB2.

The compositions provided herein may be enantiomerically pure, such as a single enantiomer or a single diastereomer, or be stereoisomeric mixtures, such as a mixture of enantiomers, a racemic mixture, or a diastereomeric mixture, or a polymorph of the active agent, for example for erlotinib, polymorphs, including but not limited to polymorphs A, B, and E, and amorphous forms or solid amorphous dispersions as disclosed in US20060154941. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When the composition described herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The composition described herein may also be provided as a prodrug, which is a functional derivative of the 1,2-diphenylpyrrole derivative and/or the EGFR inhibitor and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

Methods of Use

The invention provides a method for treating a subject having tumors, tumor-related disorders, and/or cancer, comprising administering to the subject, a therapeutically effective amount of a combination comprising 2-(4-ethoxyphenyl)-4-methyl-1-(4-sulfamoylphenyl)-pyrrole and erlotinib.

In one embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole.

In another embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the EGFR inhibitor is erlotinib.

In yet another embodiment, the invention provides a method for treating a subject having a tumors, tumor-related disorders, and/or cancer, comprising administering to the subject, a therapeutically effective amount of a combination comprising a 1,2-diphenylpyrrole derivative and an EGFR inhibitor or their respective pharmaceutically acceptable salt, solvate or prodrug.

In one embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the 1,2-diphenylpyrrole derivative is selected from the group consisting of: 4-methyl-2-(4-methylphenyl)-1-(4-sulfamoylphenyl)pyrrole; 2-(4-methoxyphenyl)-4-methyl-1-(4-sulfamoylphenyl)pyrrole; 2-(4-chlorophenyl)-4-methyl-1-(4-sulfamoylphenyl)pyrrole; 4-methyl-2-(4- methylthiophenyl)-1-(4-sulfamoylphenyl)pyrrole; 2-(4-ethoxyphenyl)-4-methyl-1-(4-sulfamoylphenyl)pyrrole; 2-(4-methoxy-3-methylphenyl)-4-methyl-1-(4-sulfamoylphenyl)pyrrole; 2-(3-fluoro-4-methoxyphenyl)-4-methyl-1-(4-sulfamoylphenyl)pyrrole; 2-(3,4-dimethylphenyl)-4-methyl-1-(4-sulfamoylphenyl)pyrrole; 4-methyl-1-(4-methylthiophenyl)-2-(4-sulfamoylphenyl)pyrrole; 1-(4-acetylaminosulfonylphenyl)-4-methyl-2-(4-methoxyphenyl)pyrrole; and 1-(4-acetylaminosulfonylphenyl)-4-methyl-2-(3,4-dimethylphenyl)pyrrole.

In yet another embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the 1,2-diphenylpyrrole derivative and the EGFR inhibitor are administered sequentially in either order or simultaneously. In a further embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the 1,2-diphenylpyrrole derivative is administered first. In one embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the EGFR inhibitor is administered first. In another embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein administering the combination enhances treatment of the subject in comparison to a treatment of either a 1,2-diphenylpyrrole derivative or an EGFR inhibitor alone. In yet another embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein administering the combination reduces the side effects of the treatment of tumors, tumor-related disorders, and/or cancer.

In one embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the cancer is selected from the group consisting of: oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, and myelodysplastic syndrome.

In another embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the cancer is non-small cell lung cancer, pancreatic cancer, breast cancer, ovarian cancer, colorectal cancer, and head and neck cancer.

In one embodiment, the invention provides a method for treating a subject having tumors, tumor-related disorders, and/or cancer, comprising administering to the subject, a therapeutically effective amount of a combination comprising a 1,2-diphenylpyrrole derivative and an EGFR inhibitor wherein the cancer is a carcinoma, a tumor, a neoplasm, a lymphoma, a melanoma, a glioma, a sarcoma, and a blastoma. In another embodiment, the invention provides a method for treating a subject having a carcinoma, comprising administering to the subject, a therapeutically effective amount of a combination comprising a 1,2-diphenylpyrrole derivative and an EGFR inhibitor wherein the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, serous carcinoma, small cell carcinoma, invasive squamous cell carcinoma, large cell carcinoma, islet cell carcinoma, oat cell carcinoma, squamous carcinoma, undifferentiated carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, basal cell carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis. In a further embodiment the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma. In yet another embodiment, the invention provides a method for treating a subject having a neoplasm, comprising administering to the subject, a therapeutically effective amount of a combination comprising a 1,2-diphenylpyrrole derivative and an EGFR inhibitor wherein the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, and malignant thymoma. In one embodiment the lymphoma is selected from the group consisting of: nervous system lymphoma, AIDS-related lymphoma, cutaneous T-cell lymphoma, non-Hodgkin's lymphoma, lymphoma, and Waldenstrom's macroglobulinemia. In another embodiment the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In a further embodiment, the invention provides a method for treating a subject having a sarcoma, comprising administering to the subject, a therapeutically effective amount of a combination comprising a 1,2-diphenylpyrrole derivative and an EGFR inhibitor wherein the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma. In one embodiment, the glioma is selected from the group consisting of: glioma, brain stem glioma, and hypothalamic and visual pathway glioma. In another embodiment, the invention provides a method for treating a subject having a blastoma, comprising administering to the subject, a therapeutically effective amount of a combination comprising a 1,2-diphenylpyrrole derivative and an EGFR inhibitor wherein the blastoma is selected from the group consisting of: pulmonary blastoma, pleuropulmonary blastoma, retinoblastoma, neuroblastoma, medulloblastoma, glioblastoma, and hemangiblastomas.

In one embodiment the EGFR inhibitor is a small molecule compound or an antibody. In another embodiment the EGFR inhibitor is a small molecule compound is selected from the group consisting of: ZM-254530, BIBX-1382, reveromycin A, gefitinib, CGP-57148, CGP-59326, 4-(m-chloro)-5,6-dimethyl-7H-pyrrolo[2,3-d]pyrimidine, tyrphostin, PKI-166, PD 153035, EKB-569, and 4-(phenylamino)quinazolines, or their pharmaceutically acceptable salts, solvates, or prodrugs. In a further embodiment, the EGFR inhibitor is an antibody is selected from the group consisting of: EGF receptor antibody, MR1scFvPE38 KDEL MDX-447, MDX-210, MD-72000, MDX-260, wayne anti-EGFR Mabs, anti-EGFr Mab, anti-EGFr MAb, Genen anti-EGFR Mab, MAb DC-101, trastuzumab, anti-VEGF monoclonal, anti-EGFR-DM1 Ab, MAb 4D5, BAB-447, EMD-55900, EMD-6200, -82633, anti-EGFR Mab, MAb 4D5, cetuximab, anti-EGFr MAb, anti-flk-1, CCX, CCZ, anti-flk-1, AG-514, AG-568, nti-EGFR-DM1 Ab, MDX-447, TgDCC-E1A, C225, matuzumab, panitumumab, DWP408, and RC-394011. In yet a further embodiment the EGFR inhibitor is selected from the group consisting of: muellerian-inhibiting hormone, TNP-470, tecogalan sodium, EGF receptor antisense, PI-88, oligonucleotide, bromelain molecules, amphiregulin, EGF fusion toxin, EGF fusion protein, Amphiregulin hbEGF-toxin, hbEGF-toxin, and EGF fusion protein.

In one embodiment the invention provides a method of inducing differentiation of tumor cells, the method comprising contacting the cells with an effective amount of a combination comprising a 1,2-diphenylpyrrole derivative and an EGFR inhibitor whereby the combination induces differentiation of tumor cells. In one embodiment, the invention provides a method of inducing differentiation of tumor cells, the method comprising contacting the cells with an effective amount of a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method of inhibiting proliferation of cancer cells, the method comprising contacting a cancer cell with a combination comprising a 1,2-diphenylpyrrole derivative and an EGFR inhibitor whereby the combination inhibits proliferation of cancer cells. In one embodiment, the invention provides a method of inhibiting proliferation of cancer cells, the method comprising contacting a cancer cell with a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In another embodiment the invention provides a method for reducing proliferation of cancer cells, the method comprising delivering to the cells a combination comprising a 1,2-diphenylpyrrole derivative and an EGFR inhibitor, whereby the reduction of cell proliferation is greater than a reduction caused by either a 1,2-diphenylpyrrole derivative alone or an EGFR inhibitor alone. In one embodiment, the invention provides a method for reducing proliferation of cancer cells, the method comprising delivering to the cells a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method of modulating autophosphorylation with a molecule of ATP, the method comprising delivering to a cancer cell an effective amount of a combination comprising a 1,2-diphenylpyrrole derivative and an EGFR inhibitor wherein the combination inhibits autophosphorylation with a molecule of ATP. In one embodiment, the invention provides a method of modulating autophosphorylation with a molecule of ATP, the method comprising delivering to a cancer cell an effective amount of a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In a further embodiment the invention provides a method of inhibiting metastases of tumor cells, the method comprising administering an effective amount of a combination comprising a 1,2-diphenylpyrrole derivative and an EGFR inhibitor such that the combination inhibits metastatic activity of tumor cells. In one embodiment, the invention provides a method of inhibiting metastases of tumor cells, the method comprising administering an effective amount of a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method for inducing apoptosis in cancer cells, the method comprising contacting the cancer cells with a combination comprising a 1,2-diphenylpyrrole derivative and an EGFR inhibitor sufficient to induce apoptosis. In one embodiment, the invention provides a method for inducing apoptosis in cancer cells, the method comprising contacting the cancer cells with a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In another embodiment the invention provides a method for sensitizing EGFR inhibitor resistant cancer cells to an EGFR inhibitor, the method comprising administering a combination comprising a 1,2-diphenylpyrrole derivative and an EGFR inhibitor wherein the combination sensitizes the cancer cells to the EGFR inhibitor. In one embodiment, the invention provides a method for sensitizing EGFR inhibitor resistant cancer cells to an EGFR inhibitor, the method comprising administering a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In a further embodiment the invention provides a method of modulating prostaglandin synthesis in a cancer cell, the method comprising contacting the cell with a combination comprising a 1,2-diphenylpyrrole derivative and an EGFR inhibitor wherein the combination inhibits prostaglandin synthesis in a cancer cell. In one embodiment, the invention provides a method of modulating prostaglandin synthesis in a cancer cell, the method comprising contacting the cell with a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method of modulating cyclooxygenase expression in a cancer cell, the method comprising delivering to the cell a combination comprising a 1,2-diphenylpyrrole derivative and an EGFR inhibitor wherein the combination inhibits cyclooxygenase expression in a cancer cell. In one embodiment, the invention provides a method of modulating cyclooxygenase expression in a cancer cell, the method comprising delivering to the cell a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method of modulating angiogenesis in a cancer cell, the method comprising contacting the cell with a combination comprising a 1,2-diphenylpyrrole derivative and an EGFR inhibitor wherein the combination inhibits angiogenesis in a cancer cell. In one embodiment the invention provides a method of modulating angiogenesis in a cancer cell, the method comprising contacting the cell with a combination comprising a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib. In another embodiment the invention provides a method of reducing the dosage in conventional treatment for neoplasia and/or neoplasia related disorders in a subject, the method comprising administering to a subject a combination of a 1,2-diphenylpyrrole derivative and an EGFR inhibitor wherein the combination reduces the dosage in conventional treatment for neoplasia and/or neoplasia-related disorders. In one embodiment, the invention provides a method of reducing the dosage in conventional treatment for neoplasia and/or neoplasia related disorders in a subject, the method comprising administering to a subject a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method of treating neoplasia and/or neoplasia related disorders, the method comprising administering a combination of a 1,2-diphenylpyrrole derivative and an EGFR inhibitor. In one embodiment, embodiment the invention provides a method of treating neoplasia and/or neoplasia related disorders, the method comprising administering a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib.

The combinations presently described herein may also be useful in the treatment of additional disorders in which aberrant expression ligand/receptor interactions or activation or signalling events related to various protein tyrosine kinases are involved. Such disorders may include those of neuronal, glial, astrocytal, hypothalamic, glandular, macrophagal, epithelial, stromal, or blastocoelic nature in which aberrant function, expression, activation or signalling of the erbB tyrosine kinases are involved. In addition, the combinations presented herein may have therapeutic utility in inflammatory, angiogenic and immunologic disorders involving both identified and as yet unidentified tyrosine kinases that are inhibited by the combinations presented herein.

Combination Therapy

In some embodiments, the composition comprising a combination of a 1,2-diphenylpyrrole derivative and an EGFR inhibitor described herein, has an effect that is additive of the effects of the 1,2-diphenylpyrrole derivative alone and the effects of the EGFR inhibitor alone. In another embodiment, the invention provides a composition comprising, a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is additive of the effects of the 2-(4-ethoxyphenyl)-4-methyl-1-(4-sulfamoylphenyl)-pyrrole alone and the effects of erlotinib alone.

In some other embodiments, the composition comprising a combination of a 1,2-diphenylpyrrole derivative and an EGFR inhibitor described herein, has an effect that is greater than the additive effects of the 1,2-diphenylpyrrole derivative alone and the effects of the EGFR inhibitor alone. In another embodiment, the invention provides a composition comprising, a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is greater than the additive effects of the 2-(4-ethoxyphenyl)-4-methyl-1-(4-sulfamoylphenyl)-pyrrole alone and the effects of erlotinib alone.

In some embodiments, the composition comprising a combination of a 1,2-diphenylpyrrole derivative and an EGFR inhibitor described herein, has an effect that is greater than the effects of the 1,2-diphenylpyrrole derivative alone (e.g., cyclooxygenase-2 inhibition alone). In another embodiment, the invention provides a composition comprising, a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is greater than the effects of the 2-(4-ethoxyphenyl)-4-methyl-1-(4-sulfamoylphenyl)-pyrrole alone.

In other embodiments, the composition comprising a combination of a 1,2-diphenylpyrrole derivative and an EGFR inhibitor described herein, has an effect that is greater than the effects of the EGFR inhibitor alone (epidermal growth factor receptor kinase inhibition alone). In another embodiment, the invention provides a composition comprising, a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is greater than the effects of erlotinib alone.

In other embodiments, the invention provides a method for treating cancer, tumors, and tumor-related disorders comprising administering a composition comprising a combination of a 1,2-diphenylpyrrole derivative and an EGFR inhibitor described herein, wherein the combination has an effect that is additive of the effects of the 1,2-diphenylpyrrole derivative alone and the effects of the EGFR inhibitor alone. In further embodiments, the invention provides a method for treating cancer, tumors, and tumor-related disorders comprising administering a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is additive of the effects of 2-(4-ethoxyphenyl)-4-methyl-1-(4-sulfamoylphenyl)-pyrrole alone and the effects of erlotinib alone.

In some other embodiments, the invention provides a method for treating cancer, tumors, and tumor-related disorders, comprising administering a composition comprising a combination of a 1,2-diphenylpyrrole derivative and an EGFR inhibitor described herein, wherein the combination has an effect that is greater than the additive effects of the effects of the 1,2-diphenylpyrrole derivative alone and the effects of the EGFR inhibitor alone. In other embodiments, the invention provides method for treating cancer, tumors, and tumor-related disorders, comprising administering a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is greater than the additive effects of 2-(4-ethoxyphenyl)-4-methyl-1-(4-sulfamoylphenyl)-pyrrole alone and the effects of erlotinib alone.

In some embodiments, the invention provides a method for treating cancer, tumors, and tumor-related disorders comprising administering a composition comprising a combination of a 1,2-diphenylpyrrole derivative and an EGFR inhibitor described herein, wherein the combination has an effect that is greater than the effects of the 1,2-diphenylpyrrole derivative alone (e.g., cyclooxygenase-2 inhibition alone). In other embodiments, the invention provides a method for treating cancer, tumors, and tumor-related disorders comprising administering a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is greater than the effects of is 2-(4-ethoxyphenyl)-4-methyl-1-(4-sulfamoylphenyl)-pyrrole alone.

In further embodiments, the invention provides a method for treating cancer, tumors, and tumor-related disorders comprising administering a composition comprising a combination of a 1,2-diphenylpyrrole derivative and an EGFR inhibitor described herein, wherein the combination has an effect that is greater than the effects of the EGFR inhibitor alone (epidermal growth factor receptor kinase inhibition alone). In other embodiments, the invention provides a method for treating cancer, tumors, and tumor-related disorders comprising administering a composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, wherein the combination has an effect that is greater than the effects of erlotinib alone.

Synergism of the composition comprising a combination of a 1,2-diphenylpyrrole derivative and an EGFR inhibitor, may be used to obtain the desired effect at doses to which side effects are minimal. For example, a patient may be treated for a disease, disorder, or condition which benefits from EGFR inhibition, such as tumors, tumor-related diseases, cancer, neoplasia, while concomitantly being treated for a side effect of the EGFR inhibition, such as inflammation, through the benefit of the 1,2-diphenylpyrrole derivative inhibitor. In one embodiment, the invention provides a combination of 2-(4-ethoxyphenyl)-4-methyl-1-(4-sulfamoylphenyl)-pyrrole and erlotinib which may be used to obtain the desired effect at doses to which side effects are minimal.

The composition comprising a combination of a 1,2-diphenylpyrrole derivative and an EGFR inhibitor, may be applied as a sole therapy or may involve one or more other materials and treatment agents such as but not limited to a combination of inhibitors of MMP (matrix-metallo-proteinase), other tyrosine kinases including VEGFR (vascular endothelial growth factor receptor), farnesyl transferase, $CTLA_4$ (cytotoxic T-lymphocyte antigen 4) and erbB2, as well as MAb to VEGFr, and other cancer-related antibodies including rhuMAb-VEGF, the erbB2 MAb, or avb3.

Thus, the composition comprising a combination of a 1,2-diphenylpyrrole derivative and an EGFR inhibitor, may be applied with one or more other anti-tumor substances, for example, those selected from, mitotic inhibitors, for example vinblastine; alkylating agents, for example, cis-platin, carboplatin, and cyclophosphamide; anti-metabolites, for example 5-fluorouracil, cytosine arabinoside and hydroxyurea, or, for example, anti-metabolites such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenyl sulphonyl)-2-hydroxy-2-methyl-3'-(trifluoromethyl)propionanilide). In one embodiment, the invention provides a combination a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, may be applied with one or more other anti-tumor substances, for example, those selected from, mitotic inhibitors, for example vinblastine; alkylating agents, for example, cis-platin, carboplatin, and cyclophosphamide; anti-metabolites, for example 5-fluorouracil, cytosine arabinoside and hydroxyurea, or, for example, anti-metabolites such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex® (tamoxifen) or, for example anti-androgens such as Casodex® (4'-cyano-3-(4-fluorophenyl sulphonyl)-2-hydroxy-2-methyl-3'-(trifluoromethyl)propionanilide).

For the combination therapies including combination therapies having pharmaceutical compositions described herein, the effective amounts of the compound presently described herein useful for inhibiting abnormal cell growth (e.g., other antiproliferative agent, anti-angiogenic, signal transduction inhibitor or immune-system enhancer) can be determined by those of ordinary skill in the art, based on the effective amounts for the compound described herein and those known or described for the chemotherapeutic or other agent. The formulations and routes of administration for such therapies and compositions can be based on the information described herein for compositions and therapies comprising the combinations presented herein as the sole active agent and on information provided for the chemotherapeutic or other agent in combination therewith.

In one embodiment, the invention provides a method for inhibiting abnormal cell growth in a subject comprising administering to the subject an effective amount of a composition comprising a combination of a 1,2-diphenylpyrrole derivative and an EGFR inhibitor, or their pharmaceutically acceptable salt, solvate or prodrug thereof, in combination with radiation therapy effective in inhibiting abnormal cell growth in the subject. Techniques for administering radiation therapy are known to a person of skill in the art and these techniques can be used in the combination therapy described herein.

Additional Therapy

Available additional treatments for cancer that may be advantageously employed in combination with the therapies and compositions disclosed herein include, without limitation, surgery, radiation therapy, chemotherapy, high dose chemotherapy with stem cell transplant; hormone therapy, and monoclonal antibody therapy.

Surgical procedure are often used in the treatment of cancer.

Radiation therapy is a cancer treatment that uses high-energy x-rays or other types of radiation to kill cancer cells or keep them from growing.

Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the spinal column, an organ, or a body cavity such as the abdomen, the drugs mainly affect cancer cells in those areas (regional chemotherapy). The way the chemotherapy is given depends on the type and stage of the cancer being treated.

Different chemotherapeutic agents are known in the art for treating cancer. Cytoxic agents used for treating cancer include doxorubicin, cyclophosphamide, methotrexate, 5-fluorouracil, mitomycin C, mitoxantrone, paclitaxel, taxane formulations such as by way of example only, Abraxane® (ABI-007), Paclitaxel-Cremophor EL, Paclitaxel poliglumex, and Paclitaxel injectable emulsion (PIE), gemcitabine, docetaxel, capecitabine and epirubicin.

Other chemotherapy against cancer includes treatment with one or more of bendamustine, carboplatin (for example, Paraplatin®), carmustine (for example, BCNU®), chlorambucil (for example, Leukeran®), cisplatin (for example, Platinol®), cyclophosphamide injection (for example, Cytoxan®), oral cyclophosphamide (for example, Cytoxan®), dacarbazine (for example, DTIC®), ifosfamide (for example, ifex®), lomustine (for example, CCNU®), mechlorethamine (for example, nitrogen mustard, Mustargen®), melphalan (for example, Alkeran®), procarbazine (for example, Matulane®), bleomycin (for example, Blenoxane®), doxorubicin (for example, Adriamycin®, Rubex®), epirubicin, Idarubicin (for example, Idamycin®), mitoxantrone (for example, Novantrone®), gemcitabine (for example, Gemzar®), oral mercaptopurine (for example, Purinethol®). methotrexate, pentostatin IV (for example, Nipent®), oral thioguanine (for example, Lanvis®), oral etoposide (for example, VP-16, VePesid®, Etopophos)—etoposide IV (for example, VP-16, VePesid®, Etopophos), vinblastine (for example, Velban®), vincristine (for example, Oncovin®), vinorelbine (for example, Navelbine®), dexamethasone (for example, Decadron®), methylprednisolone (for example, Medrol®), and prednisone (for example, Deltasone®). Erlotinib in combination with gemcitabine is indicated for the treatment of advanced pancreatic cancer.

Monoclonal antibody therapy is a cancer treatment that uses antibodies made in the laboratory, from a single type of immune system cell. These antibodies can identify substances on cancer cells or normal substances that may help cancer cells grow. The antibodies attach to the substances and kill the cancer cells, block their growth, or keep them from spreading. Monoclonal antibodies are given by infusion. They may be used alone or to carry drugs, toxins, or radioactive material directly to cancer cells. Monoclonal antibodies are also used in combination with chemotherapy as adjuvant therapy.

Trastuzumab (Herceptin®) is a monoclonal antibody that blocks the effects of the growth factor protein HER2, which transmits growth signals to breast cancer cells.

Trastuzumab leads to clinical responses as a single agent and improves survival when added to chemotherapy for advanced HER2-positive breast cancer. However, some patients do not respond to trastuzumab, and most eventually develop clinical resistance. Mechanisms of intrinsic and acquired trastuzumab resistance are poorly understood. One study which utilized a cell line-based approach to delineate genetic and protein alterations associated with resistance has been reported. (D. Tripathy et al Journal of Clinical Oncology, 2005 Vol 23, No 16S, 3121. These researchers studied two HER2-positive breast cancer cell lines (BT474 and SKBR3) that were serially passaged in the presence of trastuzumab until in vitro resistance was documented. Resistant cell lines emerged after 12 months and exhibited a 3-fold more rapid growth rate in the absence of trastuzumab. Following trastuzumab exposure, $G_0/G_1$ arrest was observed in sensitive compared to resistant cells (84 vs. 68%), with fewer cells in S-phase (3 vs. 14%). Resistant cell lines exhibited fewer changes in gene expression with trastuzumab as well as upregulation of the chemokine receptor CXCR4 and mitotic checkpoint regulators, and downregulation of PTEN compared to sensitive cells.

Additional, illustrative, treatments that may be advantageously combined with the compositions and therapies disclosed herein may include, without limitation, administration of agents including, but not limited to capecitabine, docetaxel, epirubicin, epothilone A, B or D, goserelin acetate, paclitaxel, pamidronate, bevacizumab, and trastuzumab.

EGFR Resistance

Studies have shown that after a period of about 8-12 months of EGFR-directed treatments, the cancer cells become resistant to the treatment, most commonly by 1) recruiting a mutated IGF-1 receptor to act as one of the EGFR partners in the homodimer, thus, forming a heterodimer (this allows the signal to be transmitted even in the presence of an EGFR inhibitor); 2) the presence of redundant tyrosine kinase receptors; 3) increased angiogenesis; 4) the constitutive activation of downstream mediators; and 5) the existence of specific EGFR mutations. Understanding the molecular mechanisms of resistance and sensitivity may lead to improvements in therapies that target EGFR.

IGF-1R activates many of the same downstream pathways as EGFR and can lead to tumorigenesis, increased proliferation, angiogenesis, and metastasis. PI-3K/Akt signaling is a critical component of the downstream mediation of EGFR and also plays a functional role in IGF-1R signaling. Without wishing to be bound by any particular theory, this redundancy may explain how the receptors can mimic the function of one another. Chalravarti et al., identified two glioblastoma cell lines that each overexpressed EGFR but exhibited very different responses to EGFR inhibitors. The resistant cell line significantly overexpressed IGF-1R and showed further increases in IGF-1R expression in response to EGFR inhibition by AG1478, an EGFR TKI. PI-3K/Akt signaling persisted in these resistant cell lines in response to AG1478 treatment, and these cells also maintained their invasive and antiapoptotic characteristics. These studies support the concept of redundant signaling through IGF-1R that maintains activation of critical pathways for survival in the presence of EGFR inhibition. Inhibiting both IGF-1R and EGFR may significantly reduce the growth and invasiveness of cells that are resistant to EGFR inhibitors alone. Further evidence that IGF-1R activation may bypass inhibition of other tyrosine kinase receptors comes from a study by Lu et al., who showed that the degree of overexpression of IGF-1R was inversely related to the response of breast cancer cells to trastuzumab, an antibody directed against ErbB2. SKBR3 human breast cancer cells, which normally overexpress HER2/neu and minimally express IGF-1R, showed a 42% decrease in proliferation in response to trastuzumab. Unlike the parental cell line SKBR3 cells that were engineered to overexpress IGF-1R showed no response to trastuzumab. When the IGF-1R was inhibited by IGF-binding protein-3 in the engineered cell lines, the response to trastuzumab returned to normal. These studies clearly indicate that activation of alternative tyrosine kinase receptors in tumor cells may override the effect of EGFR family inhibitors. These examples suggest that a combination may be able to overcome resistance to a single receptor inhibitor and thus more effectively inhibit pathways leading to cancer growth and survival. Recently, an enhanced response was shown in breast cancer cell lines treated with either recombinant bispecific antibodies to both EGFR and IGF-1R or a combination of single receptor antibodies compared with either antibody alone. Signaling pathways downstream of the receptors were also more effectively inhibited by the combination therapy. By combining therapies that attack multiple cell surface and intracellular signaling pathways, redundant receptor signaling might be blocked and greater clinical benefit achieved. Thus, identifying key downstream signaling molecules in which growth factor receptor signals converge may be important in the development of therapeutic agents that block signals from multiple activated growth factor receptors. Similarly, Jung et al. discloses the use of a combination of mAbs to EGFR and mAbs to VEGFR-2 to treat gastric cancer grown in nude mice. Both mAbs were modestly effective at inhibiting tumor growth, but the combination achieved significantly greater tumor growth inhibition that was also associated with decreased tumor vascularity and increased tumor cell apoptosis.

In one embodiment the invention provides a method for treating a subject having an EGFR inhibitor resistant cancer cell comprising administering to the subject a therapeutically effective amount of a composition comprising a 1,2-diphenylpyrrole derivative in combination with an EGFR inhibitor. In one embodiment, the 1,2-diphenylpyrrole derivative is 2-(4-ethoxyphenyl)-4-methyl-1-(4-sulfamoylphenyl)-pyrrole. In another embodiment the 1,2-diphenylpyrrole derivative is 2-(4-ethoxyphenyl)-4-methyl-1-(4-sulfamoylphenyl)-pyrrole and the EGFR inhibitor is erlotinib.

In one embodiment the invention provides a method for sensitizing EGFR inhibitor resistant cancer cells to an EGFR inhibitor, the method comprising administering a combination comprising a 1,2-diphenylpyrrole derivative and an EGFR inhibitor wherein the combination sensitizes the cancer cells to the EGFR inhibitor. In one embodiment, the invention provides a method for sensitizing EGFR inhibitor resistant cancer cells to erlotinib, the method comprising administering a combination comprising a 2-(4-ethoxyphenyl)-4-methyl-1-(4-sulfamoylphenyl)-pyrrole and erlotinib wherein the combination sensitizes the cancer cells erlotinib.

Lung Cancer

In many countries including Japan, Europe and America, the number of patients with lung cancer is fairly large and continues to increase year after year and is the most frequent cause of cancer death in both men and women. Although there are many potential causes for lung cancer, tobacco use, and particularly cigarette smoking, is the most important. Additionally, etiologic factors such as exposure to asbestos, especially in smokers, or radon are contributory factors. Also occupational hazards such as exposure to uranium have been identified as an important factor. Finally, genetic factors have also been identified as another factor that increases the risk of cancer.

Lung cancers can be histologically classified into non-small cell lung cancers (e.g. squamous cell carcinoma (epidermoid), adenocarcinoma, large cell carcinoma (large cell anaplastic), etc.) and small cell lung cancer (oat cell). Non-small cell lung cancer (NSCLC) has different biological properties and responses to chemotherapeutics from those of small cell lung cancer (SCLC). Thus, chemotherapeutic formulas and radiation therapy are different between these two types of lung cancer.

Non-Small Cell Lung Cancer

Where the location of the non-small cell lung cancer tumor can be easily excised (stage I and II disease) surgery is the first option of therapy and offers a relatively good chance for a cure. In more advanced disease (stage IIIa and greater), however, where the tumor has extended to tissue beyond the bronchopulmonary lymph nodes, surgery may not lead to complete excision of the tumor. In such cases, the patient's chance for a cure by surgery alone is greatly diminished. Where surgery will not provide complete removal of the NSCLC tumor, other types of therapies must be utilized. Today, chemoradiation therapy, is the standard treatment to control unresectable or inoperable NSCLC. Improved results have been seen when radiation therapy has been combined with chemotherapy, but gains have been modest and the search continues for improved methods of combining modalities.

Radiation therapy is based on the principle that high-dose radiation delivered to a target area will result in the death of reproductive cells in both tumor and normal tissues. The radiation dosage regimen is generally defined in terms of radiation absorbed dose (rad), time and fractionation, and must be carefully defined by the oncologist. The amount of radiation a patient receives will depend on various consideration but the two most important considerations are the location of the tumor in relation to other critical structures or organs of the body, and the extent to which the tumor has spread. One course of treatment for a patient undergoing radiation therapy for NSCLC will be a treatment schedule over a 5 to 6 week period, with a total dose of 50 to 60 Gy administered to the patient in a single daily fraction of 1.8 to 2.0 Gy, 5 days a week. A Gy is an abbreviation for Gray and refers to 100 rad of dose.

As NSCLC is a systemic disease, however, and radiation therapy is a local modality, radiation therapy as a single mode of therapy is unlikely to provide a cure for NSCLC, at least for those tumors that have metastasized distantly outside the zone of treatment. Thus, the use of radiation therapy with other modality regimens has important beneficial effects for the treatment of NSCLC.

Generally, radiation therapy has been combined temporally with chemotherapy to improve the outcome of treatment. There are various terms to describe the temporal relationship of administering radiation therapy in combination with COX-2 inhibitors and chemotherapy, and the following examples are the treatment regimens and are provided for illustration only and are not intended to limit the use of other combinations. "Sequential" therapy refers to the administration of a composition comprising a combination of 2-(4-ethoxyphenyl)-4-methyl-1-(4-sulfamoylphenyl)-pyrrole and erlotinib and/or radiation therapy separately in time in order to allow the separate administration of the composition, and/or radiation therapy. "Concomitant" therapy refers to the administration of the composition, and/or radiation therapy on the same day.

Finally, "alternating" therapy refers to the administration of radiation therapy on the days in which the composition would not have been administered if it was given alone. It is reported that advanced non-small cell lung cancers do not respond favorably to single-agent chemotherapy and useful therapies for advanced inoperable cancers have been limited. (Journal of Clinical Oncology, vol. 10, pp. 829-838 (1992)).

Japanese Patent Kokai 5-163293 refers to some specified antibiotics of 16-membered-ring macrolides as a drug delivery carrier capable of transporting anthracycline-type anticancer drugs into the lungs for the treatment of lung cancers. Thus, the use of a composition comprising a combination of 2-(4-ethoxyphenyl)-4-methyl-1-(4-sulfamoylphenyl)-pyrrole and erlotinib and a macrolide as a drug delivery carrier is contemplated herein for the treatment of non-small cell lung cancer.

Several chemotherapeutic agents have been shown to be efficacious against NSCLC. Chemotherapeutic agents that can be used in the present disclosure against NSCLC include cisplatin, carboplatin, paclitaxel, docetaxel, taxane formulations such as by way of example only, Abraxane® (ABI-007), Paclitaxel-Cremophor EL, Paclitaxel poliglumex, and Paclitaxel injectable emulsion (PIE), gemcitabine, navelbine, pemetrexed, etoposide, methotrexate, 5-Fluorouracil, epirubicin, doxorubicin, vinblastine, cyclophosphamide, ifosfamide, mitomycin C, epirubicin, vindesine, camptothecins, fotemustine, and edatrexate.

In one embodiment, the invention provides a method of the treatment of NSCLC which utilizes a therapeutically effective amounts of a composition comprising a combination of 2-(4-ethoxyphenyl)-4-methyl-1-(4-sulfamoylphenyl)-pyrrole and erlotinib. Further, therapy for the treatment of NSCLC utilizes a therapeutically effective amounts of a composition comprising a combination of 2-(4-ethoxyphenyl)-4-methyl-1-(4-sulfamoylphenyl)-pyrrole with erlotinib, and one of the following antineoplastic agents: bevacizumab, docetaxel, gefitinib, gemcitabine, cisplatin, carboplatin, etoposide, paclitaxel, pemetrexed, vinorelbine, or radiation therapy.

Small Cell Lung Cancer

Approximately 15 to 20 percent of all cases of lung cancer reported worldwide are small cell lung cancer (SCLC). Ihde DC: Cancer 54:2722, 1984. Currently, treatment of SCLC incorporates multi-modal therapy, including chemotherapy and radiation therapy. Response rates of localized or disseminated SCLC remain high to systemic chemotherapy, however, persistence of the primary tumor and persistence of the tumor in the associated lymph nodes has led to the integration of several therapeutic modalities in the treatment of SCLC.

Therapy for the treatment of lung cancer according to one embodiment of the invention utilizes a combination of therapeutically effective amount of a composition comprising a combination of 2-(4-ethoxyphenyl)-4-methyl-1-(4-sulfamoylphenyl)-pyrrole and erlotinib. In another embodiment, therapy for the treatment of lung cancer according to the invention utilizes a combination of therapeutically effective amount of a composition comprising a combination of 2-(4-ethoxyphenyl)-4-methyl-1-(4-sulfamoylphenyl)-pyrrole and erlotinib and one of the following antineoplastic agents: vincristine, docetaxel, camptothecin, topotecan cisplatin, carboplatin, cyclophosphamide, epirubicin (high dose), etoposide (VP-16) I.V., etoposide (VP-16) oral, isofamide, teniposide (VM-26), doxorubicin, and amrubicin. Other preferred single-agents chemotherapeutic agents that may be used in the present disclosure include BCNU (carmustine), vindesine, hexamethylmelamine (altretamine), methotrexate, nitrogen mustard, and CCNU (lomustine). Other chemotherapeutic agents under investigation that have shown activity against SCLC include iroplatin, gemcitabine, lonidamine, and taxol.

Glioma

A glioma is a type of primary central nervous system (CNS) tumor that arises from glial cells. The most common site of involvement of gliomas is the brain, but they can also affect the spinal cord or any other part of the CNS, such as the optic nerves. Treatment for brain gliomas depends on the location and the grade. Often, treatment is a combined approach, using surgery, radiation therapy, and chemotherapy. The radiation therapy is in the form of external beam radiation or the stereotactic approach using radiosurgery. Spinal cord tumors can be treated by surgery and radiation. Temozolomide is a chemotherapeutic drug that is able to cross the blood-brain barrier effectively and is being used in therapy.

EGFR is frequently amplified, overexpressed, or mutated in glioblastomas, but generally only 10 to 20% of patients have a response to EGFR inhibitors. It has been shown that glioblastoma that overexpresses the EGFRvIII oncogene and are PTEN tumor suppressor wildtype are sensitive to erlotinib treatment.

Therapy for the treatment of glioma according to one embodiment of the invention utilizes a combination of therapeutically effective amount of a composition comprising a combination of 2-(4-ethoxyphenyl)-4-methyl-1-(4-sulfamoylphenyl)-pyrrole and erlotinib. In another embodiment, therapy for the treatment of glioma according to the invention utilizes a combination of therapeutically effective amount of a composition comprising a combination of 2-(4-ethoxyphenyl)-4-methyl-1-(4-sulfamoylphenyl)-pyrrole and erlotinib and temozolomide.

Head and Neck Cancer

Head and neck cancer includes cancers of the mouth, nose, sinuses, salivary glands, throat and lymph nodes in the neck. Most begin in the moist tissues that line the mouth, nose and throat. Symptoms include a lump or sore that does not heal, a sore throat that does not go away, trouble swallowing and a change or hoarseness in the voice. Using tobacco or alcohol increases cancer risk. Treatments of head and neck cancer may include surgery, radiation therapy, chemotherapy or a combination. Treatments can affect eating, speaking or even breathing, so patients may need rehabilitation.

Head and neck cancer is often complex, with many different sites and staging systems. However, current therapy offers several alternatives, including surgery, radiation, and chemotherapy, either alone or in combination.

Combined modality therapy is becoming the principal method of treating patients with locally advanced head and neck cancers. Meanwhile, researchers are actively investigating new treatments such as gene therapy. Newer chemotherapy agents (e.g., paclitaxel [Taxol®], docetaxel [Taxotere®], gemcitabine [Gemzar®], doxorubicin [Doxil®]) may be combined with established chemotherapeutic agents (e.g., methotrexate [Trexall®, Methotrex®]) to improve results.

In March 2006, the Food and Drug Administration (FDA) approved cetuximab (Erbitux®), in combination with radiation, for patients with squamous cell carcinoma of the head and neck that cannot be treated surgically. Cetuximab also may be used alone (called monotherapy) in patients with head and neck cancer that has spread (metastasized) following standard chemotherapy.

Therapy for the treatment of head and neck cancer according to one embodiment of the invention utilizes a combination of therapeutically effective amount of a composition comprising a combination of 2-(4-ethoxyphenyl)-4-methyl-1-(4- sulfamoylphenyl)-pyrrole and erlotinib. In another embodiment, therapy for the treatment of head and neck cancer according to the invention utilizes a combination of therapeutically effective amount of a composition comprising a combination of 2-(4-ethoxyphenyl)-4-methyl-1-(4-sulfamoylphenyl)-pyrrole and erlotinib and one or more chemotherapy agents (e.g., paclitaxel [Taxol®], docetaxel [Taxotere®], gemcitabine [Gemzar®], doxorubicin [Doxil®]) which may be further combined with established chemotherapeutic agents (e.g., methotrexate [Trexall®, Methotrex®]). In another embodiment, therapy for the treatment of head and neck cancer according to the invention utilizes a combination of therapeutically effective amount of a composition comprising a combination of 2-(4-ethoxyphenyl)-4-methyl-1-(4-sulfamoylphenyl)-pyrrole and erlotinib and Erbitux®.

Colorectal Cancer

Figure 1B:
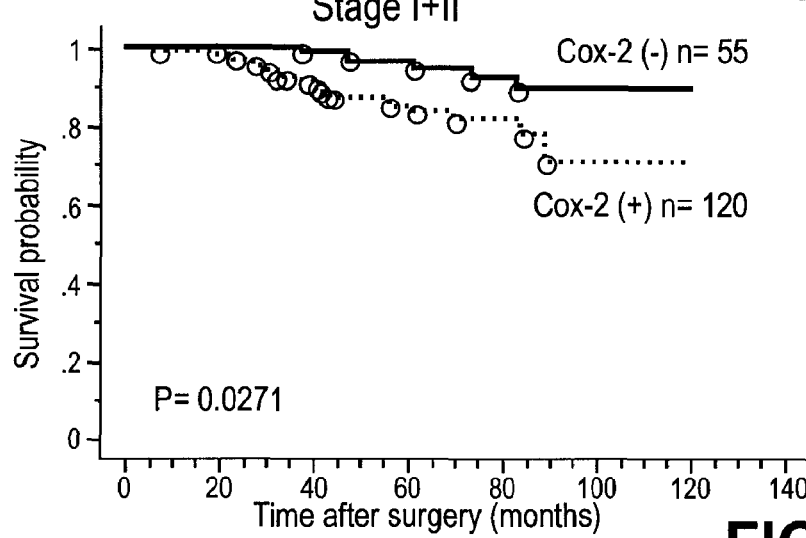
Figure 1C:
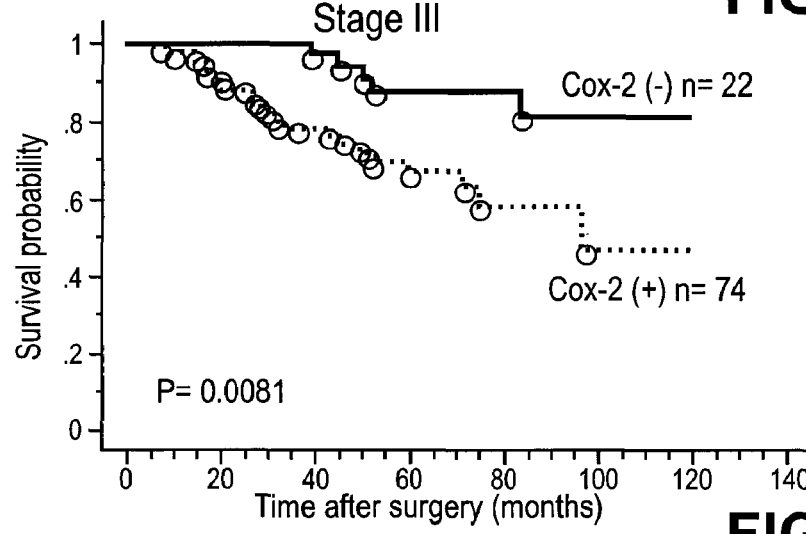

COX-2 expression levels correlate with survival rates in colorectal cancer (see FIG. 1.) Survival from colorectal cancer depends on the stage and grade of the tumor, for example precursor adenomas to metastatic adenocarcinoma. Generally, colorectal cancer can be treated by surgically removing the tumor, but overall survival rates remain between 45 and 60 percent. Colonic excision morbidity rates are fairly low and are generally associated with the anastomosis and not the extent of the removal of the tumor and local tissue. In patients with a high risk of reoccurrence, however, chemotherapy has been incorporated into the treatment regimen in order to improve survival rates.

Tumor metastasis prior to surgery is generally believed to be the cause of surgical intervention failure and up to one year of chemotherapy is required to kill the non-excised tumor cells. As severe toxicity is associated with the chemotherapeutic agents, only patients at high risk of recurrence are placed on chemotherapy following surgery. Thus, the incorporation of an antiangiogenesis inhibitor into the management of colorectal cancer plays an important role in the treatment of colorectal cancer and lead to overall improved survival rates for patients diagnosed with colorectal cancer.

One embodiment of the invention provides a combination therapy for the treatment of colorectal cancer including surgery, followed by a regimen of a composition comprising a combination of 2-(4-ethoxyphenyl)-4-methyl-1-(4-sulfamoylphenyl)-pyrrole and erlotinib. Further, another embodiment of the invention provides a combination therapy for the treatment of colorectal cancer including surgery, followed by a regimen of a composition comprising a combination of 2-(4-ethoxyphenyl)-4-methyl-1-(4-sulfamoylphenyl)-pyrrole and erlotinib, and one or more antiangiogenic agents including an MMP inhibitor, or an integrin antagonist, cycled over a one year time period. A further embodiment of the invention provides a combination therapy for the treatment of colorectal cancer including a regimen of a composition comprising a combination of 2-(4-ethoxyphenyl)-4-methyl-1-(4-sulfamoylphenyl)-pyrrole and erlotinib, followed by surgical removal of the tumor from the colon or rectum and then followed be a regimen of a composition comprising a combination of 2-(4-ethoxyphenyl)-4-methyl-1-(4-sulfamoylphenyl)-pyrrole and erlotinib cycled over a one year time period. Another therapy for the treatment of colon cancer comprises administering a combination of therapeutically effective amounts of a composition comprising a combination of 2-(4-ethoxyphenyl)-4-methyl-1-(4-sulfamoylphenyl)-pyrrole and erlotinib.

A further therapy for the treatment of colon cancer is a combination of a treatment with a composition comprising a combination of 2-(4-ethoxyphenyl)-4-methyl-1-(4-sulfamoylphenyl)-pyrrole and erlotinib in combination with the following antineoplastic agents: fluorouracil, Levamisole, camptothecin, oxaliplatin, bevacizumab, cetuximab, panitumumab, irinotecan, leucovorin, and capecitabine.

Breast Cancer

Today, among women in the United States, breast cancer remains the most frequent diagnosed cancer. One in 8 women in the United States is at risk of developing breast cancer in their lifetime. Age, family history, diet, and genetic factors have been identified as risk factors for breast cancer. Breast cancer is the second leading cause of death among women.

Different chemotherapeutic agents are known in art for treating breast cancer. Cytoxic agents used for treating breast cancer include doxorubicin, cyclophosphamide, methotrexate, 5-fluorouracil, mitomycin C, mitoxantrone, paclitaxel, taxane formulations such as by way of example only, Abraxane® (ABI-007), Paclitaxel-Cremophor EL, Paclitaxel poliglumex, and Paclitaxel injectable emulsion (PIE), gemcitabine, docetaxel, capecitabine, lapatanib, trastuzumab, anastrozole, letrozole, exemestane, and epirubicin. In the treatment of locally advanced noninflammatory breast cancer, a composition comprising a combination of 2-(4-ethoxyphenyl)-4-methyl-1-(4-sulfamoylphenyl)-pyrrole and erlotinib can be used to treat the disease. Additionally, in combination with surgery, radiation therapy or with chemotherapeutic or other antiangiogenic agents. Other combinations of chemotherapeutic agents, that can be used in combination with the present disclosure include, but are not limited to anastrozole, capecitabine, docetaxel, epirubicin, exemestane, fulvestrant, epothilone A, B or D, goserelin acetate, letrozole, bevacizumab, paclitaxel, pamidronate, tamoxifen, toremifene, and trastuzumab.

Hormone Positive

Many breast cancers require the hormone oestrogen to grow. In women who have had their menopause, the main source of oestrogen is through the conversion of androgens into oestrogens. This process is carried out by the aromatase enzyme. In the treatment of hormone positive breast cancer a composition comprising a combination of 2-(4-ethoxyphenyl)-4-methyl-1-(4-sulfamoylphenyl)-pyrrole and erlotinib can be used to treat the disease in combination with other agents, such as, aromatase inhibitors, for e.g., exemestane, letrozole, and anastrozole.

HER2/neu Positive Breast Cancer

In the treatment of HER2/neu positive breast cancer, compositions comprising a combination of 2-(4-ethoxyphenyl)-4-methyl-1-(4-sulfamoylphenyl)-pyrrole and erlotinib can be used to treat the disease in combination with other antiangiogenic agents, or in combination with surgery, radiation therapy or with chemotherapeutic agents. Other chemotherapeutic agents include, for example, trastuzumab, lapatinib, and CL-387785.

Triple Negative Breast Cancer

In the treatment of triple negative breast cancer wherein the cancer is estrogen receptor-negative, progesterone receptor-negative and HER2-negative, compositions comprising a combination of 2-(4-ethoxyphenyl)-4-methyl-1-(4-sulfamoylphenyl)-pyrrole and erlotinib can be used to treat the disease in combination with other therapeutic agents. Such agents include, by way of example only, cetuximab, paclitaxel, docetaxel, taxane formulations, for example, Abraxane® (ABI-007), Paclitaxel-Cremophor EL, Paclitaxel poliglumex, and Paclitaxel injectable emulsion (PIE).

Ovarian Cancer

Celomic epithelial carcinoma accounts for approximately 90% of ovarian cancer cases. One therapy for the treatment of ovary cancer is a combination of therapeutically effective amounts of a composition comprising a combination of 2-(4-ethoxyphenyl)-4-methyl-1-(4-sulfamoylphenyl)-pyrrole and erlotinib.

Other agents that can be used in combination with a composition comprising a combination 2-(4-ethoxyphenyl)-4-methyl-1-(4-sulfamoylphenyl)-pyrrole and erlotinib include, but are not limited to: alkylating agents, ifosfamide, cisplatin, carboplatin, paclitaxel, docetaxel, PEGylated liposomal doxorubicin, gemcitabine, doxorubicin, epothilone A, B, or D, topotecan, liposomal doxorubicin 5-fluorouracil, methotrexate, mitomycin, hexamethylmelamine, progestins, antiestrogens, prednimustine, dihydroxybusulfan, galactitol, interferon alpha, and interferon gama.

Other combinations for the treatment of celomic epithelial carcinoma is a combination of therapeutically effective amounts of a composition comprising a combination of 2-(4-ethoxyphenyl)-4-methyl-1-(4-sulfamoylphenyl)-pyrrole and erlotinib and one of the following combinations of antineoplastic agents: 1) cisplatin, doxorubicin, cyclophosphamide; 2) hexamethylmelamine, cyclosphamide, doxorubicin, cisplatin; 3) cyclophosphamide, hexamethylmelamine, 5-fluorouracil, cisplatin; 4) melphalan, hexamethylmelamine, cyclophosphamide; 5) melphalan, doxorubicin, cyclophosphamide; 6) cyclophosphamide, cisplatin, carboplatin; 7) cyclophosphamide, doxorubicin, hexamethylmelamine, cisplatin; 8) cyclophosphamide, doxorubicin, hexamethylmelamine, carboplatin; 9) cyclophosphamide, cisplatin; 10) hexamethylmelamine, doxorubicin, carboplatin; 11) cyclophosphamide, hexamethimelamine, doxorubicin, cisplatin; 12) carboplatin, cyclophosphamide; 13) cisplatin, cyclophosphamide.

Cancer of the fallopian tube accounts for approximately 400 new cancer cases per year in the United States. One therapy according to the invention is for the treatment of fallopian tube cancer which includes administering a combination of therapeutically effective amount of a composition comprising a combination of 2-(4-ethoxyphenyl)-4-methyl-1-(4-sulfamoylphenyl)-pyrrole and erlotinib. Other agents that can be used in combination with a composition comprising a combination 2-(4-ethoxyphenyl)-4-methyl-1-(4-sulfamoylphenyl)-pyrrole and erlotinib include, but are not limited to: alkylating agents, ifosfamide, cisplatin, carboplatin, paclitaxel, docetaxel, PEGylated liposomal doxorubicin, gemcitabine, doxorubicin, epothilone A, B, or D, topotecan, liposomal doxorubicin, 5-fluorouracil, methotrexate, mitomycin, hexamethylmelamine, progestins, antiestrogens, prednimustine, dihydroxybusulfan, galactitol, interferon α, and interferon γ.

Germ cell ovarian cancer accounts for approximately 5% of ovarian cancer cases. Germ cell ovarian carcinomas are classified into two main groups: dysgerminoma, and nondysgerminoma. Nondysgerminoma is further classified into teratoma, endodermal sinus tumor, embryonal carcinoma, choricarcinoma, polyembryoma, and mixed cell tumors. One therapy for the treatment of germ cell carcinoma is a combination of therapeutically effective amount of a composition comprising a combination of 2-(4-ethoxyphenyl)-4-methyl-1-(4-sulfamoylphenyl)-pyrrole and erlotinib.

One therapy according to the invention is for the treatment of germ cell carcinoma which comprises administering a combination of a therapeutically effective amount of a composition comprising a combination of 2-(4-ethoxyphenyl)-4-methyl-1-(4-sulfamoylphenyl)-pyrrole and erlotinib and the following combinations of antineoplastic agents: 1) vincristine, actinomycin D, cyclophosphamide; 2) bleomycin, etoposide, cisplatin; 3) vinblastine, bleomycin, cisplatin.

Pancreatic Cancer

Approximately 2% of new cancer cases diagnosed in the United States are pancreatic cancer. Pancreatic cancer is generally classified into two clinical types: 1) adenocarcinoma (metastatic and non-metastatic), and 2) cystic neoplasms (serous cystadenomas, mucinous cystic neoplasms, papillary cystic neoplasms, acinar cell systadenocarcinoma, cystic choriocarcinoma, cystic teratomas, angiomatous neoplasms). Erlotinib in combination with gemcitabine is indicated for treatment of patients with locally advanced, unresectable or metastatic pancreatic cancer.

Combinations of therapy for the treatment of non-metastatic adenocarcinoma that may be used in the present disclosure include the use of a composition comprising a combination of 2-(4-ethoxyphenyl)-4-methyl-1-(4-sulfamoylphenyl)-pyrrole and erlotinib along with preoperative biliary tract decompression (patients presenting with obstructive jaundice); surgical resection, including standard resection, extended or radial resection and distal pancreatectomy (tumors of body and tail); adjuvant radiation; anti-angiogenic therapy; and chemotherapy.

For the treatment of metastatic adenocarcinoma, a combination therapy consists of a composition comprising a combination of 2-(4-ethoxyphenyl)-4-methyl-1-(4-sulfamoylphenyl)-pyrrole and erlotinib of the present disclosure in combination with continuous treatment of 5-fluorouracil, followed by weekly cisplatin therapy.

Another combination therapy for the treatment of cystic neoplasms is the use of a composition comprising a combination of 2-(4-ethoxyphenyl)-4-methyl-1-(4-sulfamoylphenyl)-pyrrole and erlotinib in combination with gemcitabine.

Pharmaceutical Compositions

Provided herein is a pharmaceutical composition for treating cancer comprising a combination of a 1,2-diphenylpyrrole derivative and an EGFR inhibitor; and a pharmaceutically acceptable excipient or carrier.

In one embodiment, the invention provides a pharmaceutical composition comprising a combination of 2-(4-ethoxyphenyl)-4-methyl-1-(4-sulfamoylphenyl)-pyrrole and erlotinib as an active ingredient, or a pharmaceutically acceptable salt, solvate, or prodrug thereof, in a pharmaceutically acceptable vehicle, carrier, diluent, or excipient, or a mixture thereof; and one or more pharmaceutically acceptable excipients or carriers.

In another embodiment, the 1,2-diphenylpyrrole derivative is 2-(4-ethoxyphenyl)-4-methyl-1-(4-sulfamoylphenyl)-pyrrole and a pharmaceutically acceptable excipient or carrier. In another embodiment, the EGFR inhibitor is erlotinib and a pharmaceutically acceptable excipient or carrier. In a further embodiment the 1,2-diphenylpyrrole derivative is 2-(4-ethoxyphenyl)-4-methyl-1-(4-sulfamoylphenyl)-pyrrole and the EGFR inhibitor is erlotinib and a pharmaceutically acceptable excipient or carrier.

In one embodiment, the invention provides a pharmaceutical composition for treating cancer comprising a combination of a 1,2-diphenylpyrrole derivative selected from the group consisting of: 4-methyl-2-(4-methylphenyl)-1-(4-sulfamoylphenyl)pyrrole; 2-(4-methoxyphenyl)-4-methyl-1-(4-sulfamoylphenyl)pyrrole; 2-(4-chlorophenyl)-4-methyl-1-(4-sulfamoylphenyl)pyrrole; 4-methyl-2-(4-methylthiophenyl)-1-(4-sulfamoylphenyl)pyrrole; 2-(4-ethoxyphenyl)-4-methyl-1-(4-sulfamoylphenyl)pyrrole; 2-(4-methoxy-3-methylphenyl)-4-methyl-1-(4-sulfamoylphenyl)pyrrole; 2-(3-fluoro-4-methoxyphenyl)-4-methyl-1-(4-sulfamoylphenyl)pyrrole; 2-(3,4-dimethylphenyl)-4-methyl-1-(4-sulfamoylphenyl)pyrrole; 4-methyl-1-(4-methylthiophenyl)-2-(4-sulfamoylphenyl)pyrrole; 1-(4-acetylaminosulfonylphenyl)-4-methyl-2-(4-methoxyphenyl)

pyrrole; and 1-(4-acetylaminosulfonylphenyl)-4-methyl-2-(3,4-dimethylphenyl)pyrrole. In another embodiment, the invention provides a method wherein the 1,2-diphenylpyrrole derivative is 2-(4-ethoxyphenyl)-4-methyl-1-(4-sulfamoylphenyl)-pyrrole and an EGFR inhibitor; and a pharmaceutically acceptable excipient or carrier.

Provided herein are pharmaceutical compositions comprising a combination of a 1,2-diphenylpyrrole derivative and an EGFR inhibitor as an active ingredient, or a pharmaceutically acceptable salt, solvate, or prodrug thereof, in a pharmaceutically acceptable vehicle, carrier, diluent, or excipient, or a mixture thereof; and one or more pharmaceutically acceptable excipients or carriers.

Also provided herein are pharmaceutical compositions comprising a combination of a 1,2-diphenylpyrrole derivative and an EGFR inhibitor as an active ingredient, or a pharmaceutically acceptable salt, solvate, or prodrug thereof, in a pharmaceutically acceptable vehicle, carrier, diluent, or excipient, or a mixture thereof; and one or more release controlling excipients as described herein. Provided herein are pharmaceutical compositions comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof, in a pharmaceutically acceptable vehicle, carrier, diluent, or excipient, or a mixture thereof, and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. The pharmaceutical compositions may also comprise non-release controlling excipients.

Provided herein are pharmaceutical compositions in film-coated dosage forms, which comprise a combination of a 1,2-diphenylpyrrole derivative and an EGFR inhibitor as an active ingredient, or a pharmaceutically acceptable salt, solvate, or prodrug thereof, and one or more tabletting excipients to form a tablet core using conventional tabletting processes and subsequently coating the core. The tablet cores can be produced using conventional granulation methods, for example wet or dry granulation, with optional comminution of the granules and with subsequent compression and coating. Granulation methods are described, for example, in Voigt, pages 156-69 (Voigt, R. (1984): Lehrbuch der pharmazeutischen Technologie (Textbook of Pharmaceutical Technology); Verlag Chemie Weinheim—Beerfield Beach/Florida—Basle).

Suitable excipients for the production of granules are, for example pulverulent fillers optionally having flow-conditioning properties, for example talcum, silicon dioxide, for example synthetic amorphous anhydrous silicic acid of the Syloid® type (Grace), for example SYLOID 244 FP, microcrystalline cellulose, for example of the Avicel® type (FMC Corp.), for example of the types AVICEL PH101, 102, 105, RC581 or RC 591, Emcocel® type (Mendell Corp.) or Elcema® type (Degussa); carbohydrates, such as sugars, sugar alcohols, starches or starch derivatives, for example lactose, dextrose, saccharose, glucose, sorbitol, mannitol, xylitol, potato starch, maize starch, rice starch, wheat starch or amylopectin, tricalcium phosphate, calcium hydrogen phosphate or magnesium trisilicate; binders, such as gelatin, tragacanth, agar, alginic acid, cellulose ethers, for example methylcellulose, carboxymethylcellulose or hydroxypropylmethylcellulose, polyethylene glycols or ethylene oxide homopolymers, especially having a degree of polymerization of approximately from $2.0 \times 10^3$ to $1.0 \times 10^5$ and an approximate molecular weight of about from $10 \times 10^5$ to $5.0 \times 10^6$, for example excipients known by the name Polyox® (Union Carbide), polyvinylpyrrolidone or povidones, especially having a mean molecular weight of approximately 1000 and a degree of polymerization of approximately from about 500 to about 2500, and also agar or gelatin; surface-active substances, for example anionic surfactants of the alkyl sulfate type, for example sodium, potassium or magnesium n-dodecyl sulfate, n-tetradecyl sulfate, n-hexadecyl sulfate or n-octadecyl sulfate, of the alkyl ether sulfate type, for example sodium, potassium or magnesium n-dodecyloxyethyl sulfate, n-tetradecyloxyethyl sulfate, n-hexadecyloxyethyl sulfate or n-octadecyloxyethyl sulfate, or of the alkanesulfonate type, for example sodium, potassium or magnesium n-dodecanesulfonate, n-tetradecanesulfonate, n-hexadecanesulfonate or n-octadecanesulfonate, or non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethylene glycol 400 stearate, polyethylene glycol 2000 stearate, especially ethylene oxide/propylene oxide block polymers of the Pluronics® (BWC) or Synperonic® (ICI) type Further provided herein are pharmaceutical compositions in enteric coated dosage forms, which comprise a combination of a 1,2-diphenylpyrrole derivative and an EGFR inhibitor as an active ingredient, or a pharmaceutically acceptable salt, solvate, or prodrug thereof; and one or more release controlling excipients for use in an enteric coated dosage form. Provided herein are pharmaceutical compositions in enteric coated dosage forms comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof, in a pharmaceutically acceptable vehicle, carrier, diluent, or excipient, or a mixture thereof; and one or more release controlling excipients for use in an enteric coated dosage form. The pharmaceutical compositions may also comprise non-release controlling excipients.

Further provided herein are pharmaceutical compositions in effervescent dosage forms, which comprise a combination of a 1,2-diphenylpyrrole derivative and an EGFR inhibitor as an active ingredient, or a pharmaceutically acceptable salt, solvate, or prodrug thereof; and one or more release controlling excipients for use in effervescent dosage forms. Also provided herein are pharmaceutical compositions in effervescent dosage forms comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof, in a pharmaceutically acceptable vehicle, carrier, diluent, or excipient, or a mixture thereof; and one or more release controlling excipients for use in an effervescent dosage forms. The pharmaceutical compositions may also comprise non-release controlling excipients.

Additionally provided are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a combination of a 1,2-diphenylpyrrole derivative and an EGFR inhibitor as an active ingredient, or a pharmaceutically acceptable salt, solvate, or prodrug thereof; and one or more release controlling and non-release controlling excipients, such as those excipients suitable for a disruptable semi-permeable membrane and as swellable substances. Additionally, the invention provides pharmaceutical compositions comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof; and one or more release controlling and non-release controlling excipients, such as those excipients suitable for a disruptable semi-permeable membrane and as swellable substances.

Provided herein also are pharmaceutical compositions in a dosage form for oral administration to a subject, which comprises a combination of a 1,2-diphenylpyrrole derivative and an EGFR inhibitor as an active ingredient, or a pharmaceutically acceptable salt, solvate, or prodrug thereof, and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer. Additionally, the invention provides pharmaceutical compositions in a dosage form for oral administration to a subject comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib enclosed in an intermediate reactive layer comprising a gastric juice-resistant polymeric layered material partially neutralized with alkali and having cation exchange capacity and a gastric juice-resistant outer layer.

Provided herein are pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 200 mg, about 300 mg, about 400 mg, about 500 mg, about 600 mg, about 800 mg, about 1200 mg of a combination of a 1,2-diphenylpyrrole derivative and an EGFR inhibitor as an active ingredient, or a pharmaceutically acceptable salt, solvate, or prodrug thereof, in the form of enteric-coated granules, as delayed-release capsules for oral administration. Also, the invention provides for pharmaceutical compositions that comprise about 0.1 to about 1000 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg of a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof, in the form of enteric-coated granules, as delayed-release capsules for oral administration.

Provided herein are pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg, about 600 mg, about 800 mg, about 1200 mg of a combination of a 1,2-diphenylpyrrole derivative and an EGFR inhibitor as an active ingredient, or a pharmaceutically acceptable salt, solvate, or prodrug thereof in the form of enteric-coated pellets, as delayed-release capsules for oral administration. Also, the invention provides for pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg, about 600 mg, about 800 mg, about 1200 mg of a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof in the form of enteric-coated pellets, as delayed-release capsules for oral administration. The pharmaceutical compositions further comprise glyceryl monostearate 40-50, hydroxypropyl cellulose, hypromellose, magnesium stearate, methacrylic acid copolymer type C, polysorbate 80, sugar spheres, talc, and triethyl citrate.

Provided herein are pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg, about 600 mg, about 800 mg, about 1200 mg of a combination of a 1,2-diphenylpyrrole derivative and an EGFR inhibitor as an active ingredient, or a pharmaceutically acceptable salt, solvate, or prodrug thereof, as enteric-coated delayed-release tablets for oral administration. Also, the pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg, about 600 mg, about 800 mg, about 1200 mg of a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof, as enteric-coated delayed-release tablets for oral administration. The pharmaceutical compositions further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

Provided herein are pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg, about 600 mg, about 800 mg, about 1200 mg of a combination of a 1,2-diphenylpyrrole derivative and an EGFR inhibitor as an active ingredient, or a pharmaceutically acceptable salt, solvate, or prodrug thereof, as enteric-coated delayed-release tablets for oral administration. Also provided herein are pharmaceutical compositions that comprise about 0.1 to about 1200 mg, about 1 to about 500 mg, about 2 to about 100 mg, about 1 mg, about 2 mg, about 3 mg, about 5 mg, about 10 mg, about 20 mg, about 30 mg, about 40 mg, about 50 mg, about 100 mg, about 500 mg, about 600 mg, about 800 mg, about 1200 mg of a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib as an active ingredient, or a pharmaceutically acceptable salt, solvate, or prodrug thereof, as enteric-coated delayed-release tablets for oral administration. The pharmaceutical compositions further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The pharmaceutical compositions provided herein may be provided in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The compositions provided herein may be administered alone, or in combination with one or more other compounds provided herein, one or more other active ingredients. The pharmaceutical compositions that comprise a compound provided herein may be formulated in various dosage forms for oral, parenteral, buccal, intranasal, epidural, sublingual, pulmonary, local, rectal, transdermal, or topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the combinations may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the combinations may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

As described herein, the compositions and methods for using the composition comprising a combination of a 1,2-diphenylpyrrole derivative and an EGFR inhibitor, may be formulated without carriers or excipients or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to about 5% of suspending agent, syrups containing, for example, from about 10 to about 50% of sugar, and elixirs containing, for example, from about 20 to about 50% ethanol, and the like. Such pharmaceutical preparations may contain, for example, from about 0.05 up to about 90% of the active ingredient in combination with the carrier, more usually between about 5% and about 60% by weight. Also, the compositions and methods for using the composition comprising a combination of a 1,2-diphenylpyrrole derivative and an EGFR inhibitor wherein the 1,2-diphenylpyrrole derivative is 2-(4-ethoxyphenyl)-4-methyl-1-(4-sulfamoylphenyl)-pyrrole and the EGFR inhibitor is erlotinib, may be formulated without carriers or excipients or may be combined with one or more pharmaceutically acceptable carriers for administration.

The effective dosage of each active ingredient employed may vary depending on the particular compound employed, the mode of administration and the severity of the condition being treated. The projected daily dosage of the EGFR inhibitor will depend on many factors. Numerous methods for evaluating and comparing 1,2-diphenylpyrrole derivative inhibitor potency are known to one of skill in the art. In one embodiment, an oral daily dosage of the 1,2-diphenylpyrrole derivative inhibitor is in the range of about 0.01 to about 30 mg/kg, and the projected daily dosage of the EGFR inhibitor is in the range of about 0.3 to about 8 mg/kg. This dosage regimen may be adjusted to provide the optimal therapeutic response. For example, several divided doses may be administered daily or the dose may be proportionally reduced as indicated by the exigencies of the therapeutic situation. The 1,2-diphenylpyrrole derivative inhibitor and the EGFR inhibitor may also be administered as a combined dosage unit, or as separate components. When administered as separate components, each component may be administered at the same time, or at different times during the treatment period.

It is understood, however, that a specific dose level for any particular patient will depend upon a variety of factors such as, for example, decreases in the liver and kidney function.

Treatment dosages generally may be titrated to optimize safety and efficacy. Typically, dosage-effect relationships from in vitro studies initially can provide useful guidance on the proper doses for patient administration. Studies in animal models also generally may be used for guidance regarding effective dosages for treatment of cancers in accordance with the present disclosure. In terms of treatment protocols, it should be appreciated that the dosage to be administered will depend on several factors, including the particular agent that is administered, the route administered, the condition of the particular patient, etc. Determination of these parameters are well within the skill of the art. These considerations, as well as effective formulations and administration procedures are well known in the art and are described in standard textbooks.

Oral Formulations

Oral formulations containing the active combinations described herein may comprise any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Oral Administration

As described herein, the combination regimen can be given simultaneously or can be given in a staggered regimen, with a 1,2-diphenylpyrrole derivative being given at a different time during the course of chemotherapy than an EGFR inhibitor. This time differential may range from several minutes, hours, days, weeks, or longer between administration of the two compounds. Therefore, the term combination does not necessarily mean administered at the same time or as a unitary dose, but that each of the components are administered during a desired treatment period. The agents may also be administered by different routes. As is typical for chemotherapeutic regimens, a course of chemotherapy may be repeated several weeks later, and may follow the same timeframe for administration of the two compounds, or may be modified based on patient response.

In other embodiments, the pharmaceutical compositions provided herein may be provided in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

In other embodiments, the pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Miccellar dosage forms can be prepared as described in U.S. Pat. No. 6,350,458.

In other embodiments, the pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

In further embodiments, the pharmaceutical compositions provided herein may be co-formulated with other active ingredients which do not impair the desired therapeutic action, or with substances that supplement the desired action, such as other cholinergic agents, other serotoninergic agents, alpha adrenergic agents, $CCK_A$ antagonists, $5$-$HT_3$ antagonists, NMDA receptor antagonists, opioids, prokinetics, tachykinins, antalarmin, and Z-338.

Parenteral Administration

In some embodiments, the pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

In other embodiments, the pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

In some embodiments, the pharmaceutical compositions provided herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Modified Release

In other embodiments, the pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

Matrix Controlled Release Devices

In some embodiments, the pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

In other embodiments, the pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

In some embodiments, the pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semi-permeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semi-permeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semi-permeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semi-permeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In other embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

In some embodiments, the pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

In some embodiments, the pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975;

6,004,534; 5,985,307; 5,972,366; 5,900,252; 5,840,674; 5,759,542; and 5,709,874, all of which are incorporated herein by their entirety.

Immediate Release

In some embodiments, the pharmaceutical compositions provided herein in an immediate release dosage form are capable of releasing not less than 75% of the therapeutically active ingredient or combination and/or meet the disintegration or dissolution requirements for immediate release tablets of the particular therapeutic agents or combination included in the tablet core, as set forth in USP XXII, 1990 (The United States Pharmacopeia.)

Topical Administration

In other embodiments, the pharmaceutical compositions provided herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

In further embodiments, the pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

In some embodiments, the pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or an surfactant, such as sorbitan trioleate, oleic acid, or an oligolactic acid.

In another embodiment, the pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

In one embodiment, the pharmaceutical compositions provided herein for topical administration may be formulated to be immediate release or modified release, including delayed-, sustained-, pulsed-, controlled-, targeted, and programmed release.

EXAMPLES

Example 1

Synthesis of 2-(4-ethoxyphenyl)-4-methyl-1-(4-sulfamoylphenyl)-pyrrole

Scheme 1.

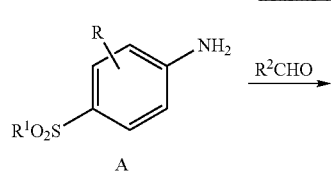

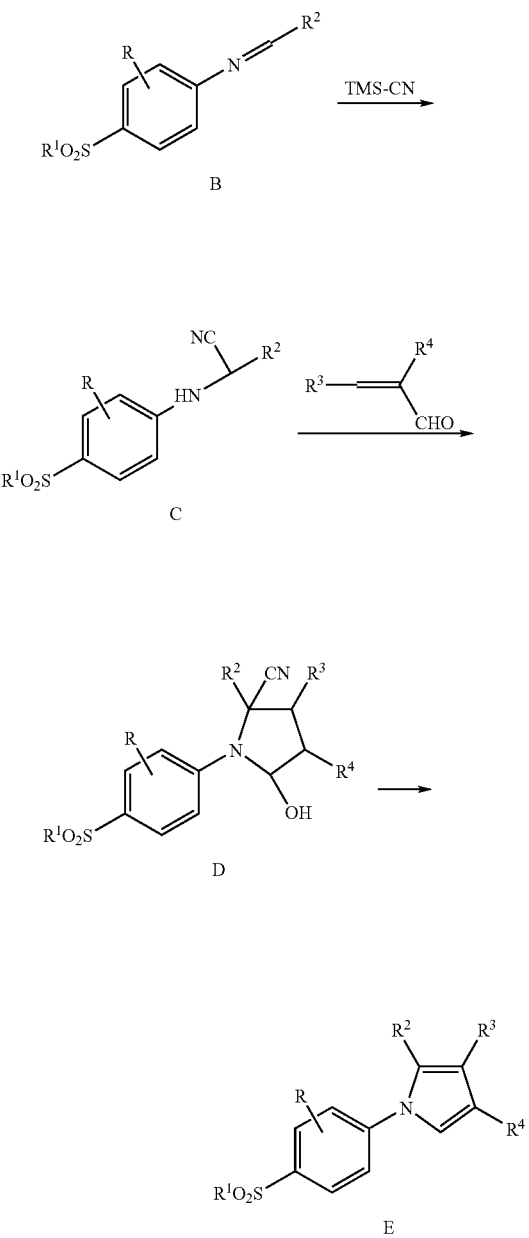

Substituted benzaldehyde undergoes dehydration condensation by reaction with aniline compound A in an inert solvent at a temperature of between 5° C. to 200° C. to give aldimine compound B. Trimethylsilyl cyanide is then reacted with aldimine compound B in the presence of a Lewis acid to afford anilinonitrile C. An α-β-unsaturated aldehyde is then reacted with anilinonitrile C to afford compound D which then undergoes dehydration and dehydrogencyanation under basic conditions in a modification of the method described in Ann. Chem. 589, 176 (1954).

Example 2

Synthesis of Erlotinib

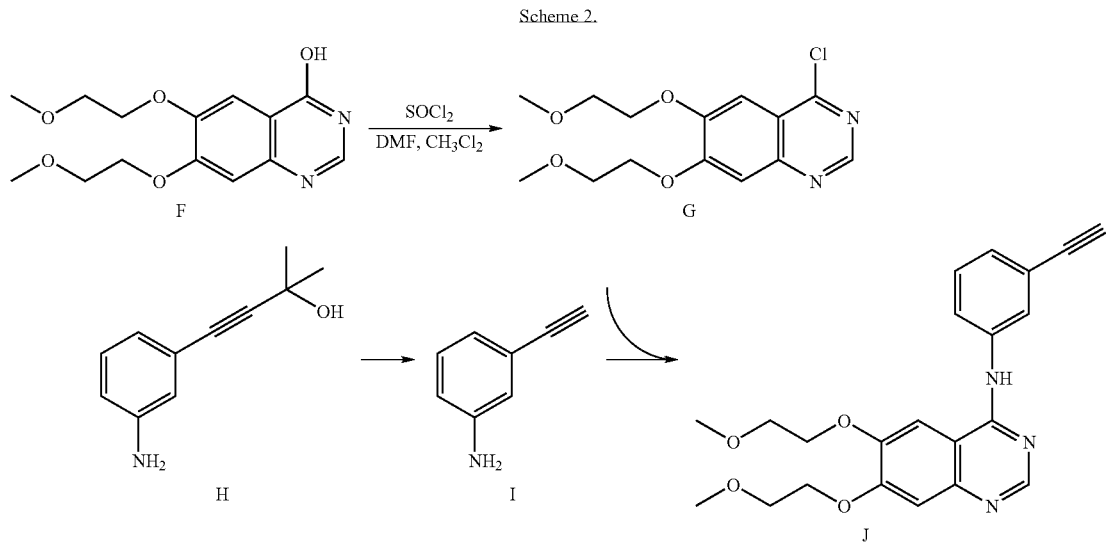

Starting material compound H is heated in a suspension of metal alkali and solvent, then heated to give compound I. Starting material alcohol F, is placed in a solvent mixture of thionyl chloride, methylene chloride and dimethylformamide to give the chloride G. Chloride G is then coupled with compound I to give erlotinib J.

Example 3

Pharmacokinetics and Metabolism of 2-(4-ethoxyphenyl)-4-methyl-1-(4-sulfamoylphenyl)-pyrrole Orally administered 2-(4-ethoxyphenyl)-4-methyl-1-(4-sulfamoylphenyl)-pyrrole was rapidly absorbed in all species examined (mice, rats, dogs, and monkeys). Peak plasma concentrations were achieved between 1 and 3 hours after a dose of 5 mg/kg. The elimination half life ($t_{1/2}$) was 4-5 hours in rodents and dogs, and approximately 2 hours in monkeys. Oral availability was greatest in rodent, and was reduced in dogs and monkeys (59 and 34% respectively). Pharmacokinetics in human subjects demonstrated a linear dose exposure relationship from doses of 2 mg to 800 mg given orally. The half-life in human subjects is 15-18 hours.

Example 4

Toxicology of 2-(4-ethoxyphenyl)-4-methyl-1-(4-sulfamoylphenyl)-pyrrole

Toxicological evaluation of 2-(4-ethoxyphenyl)-4-methyl-1-(4-sulfamoylphenyl)-pyrrole in mice, rats, dogs and monkeys revealed expected findings related to inhibition of cyclooxygenase and consistent with animal safety observations with other COX-2 selective inhibitors. In single dose studies, the minimum lethal dose of 2-(4-ethoxyphenyl)-4-methyl-1-(4-sulfamoylphenyl)-pyrrole was 600 mg/kg in rats and >2000 mg/kg in dogs. An endoscopy study conducted in human subjects demonstrated no increase in gastric or duodenal toxicity compared to placebo.

Example 5

Biological Evaluation

COX-2 Selective Inhibitors
HT-29 Model:

Mice are injected subcutaneously in the left paw ($1\times10^6$ tumor cells suspended in 30% Matrigel) and tumor volume is evaluated using a phlethysmometer twice a week for 30-60 days. Implantation of human colon cancer cells (HT-29) into nude mice produces tumors that will reach 0.6-2 ml between 30-50 days. Blood is drawn twice during the experiment in a 24 h protocol to assess plasma concentration and total exposure by AUC analysis. The data is expressed as the mean +/−SEM. Student's and Mann-Whitney tests are used to assess differences between means using the InStat software package.

A. Mice injected with HT-29 cancer cells are treated with cytoxin i.p at doses of 50 mg/kg on days 5, 7 and 9 in the presence or absence of a composition comprising a combination of 2-(4-ethoxyphenyl)-4-methyl-1-(4-sulfamoylphenyl)-pyrrole with erlotinib in the diet. The efficacy of both agents are determined by measuring tumor volume. The results from these studies may demonstrate that a composition comprising a combination of 2-(4-ethoxyphenyl)-4-methyl-1-(4-sulfamoylphenyl)-pyrrole with erlotinib administered in the diet to tumor bearing mice can delay the growth of tumors and metastasis when administered as sole therapy.

B. In a second assay, mice are injected with HT-29 cancer cells are then treated with 5-FU on days 12 through 15. Mice injected with HT-29 cancer cells are treated with 5-FU i.p at doses of 50 mg/kg on days 12, 13, 14, and 15 in the presence or absence of a composition comprising a combination of 2-(4-ethoxyphenyl)-4-methyl-1-(4-sulfamoylphenyl)-pyrrole with erlotinib in the diet. The efficacy of both agents are determined by measuring tumor volume. Treatment using the composition may reduce tumor volume by up to 70%. In the same assay, 5-FU decreases tumor volume by 61%. Further, the composition and 5-FU may decrease tumor volume by 83%.

C. In a third assay, mice injected with HT-29 colon cancer cells are treated with 5-FU i.p 50 mg/kg on days 14 through 17 in the presence or absence of a composition comprising a combination of 2-(4-ethoxyphenyl)-4-methyl-1-(4-sulfamoylphenyl)-pyrrole with erlotinib (1600 ppm) and valdecoxib (160 ppm) in the diet. The efficacy of both agents are determined by measuring tumor volume. Treatment with 5-FU may result in a 35% reduction in tumor volume. Treatment with the composition and valdecoxib may reduce tumor volume by 52% and 69%, respectively. In the same assay, the combination of 5-FU and the composition may decrease tumor volume by 72% while the combination of 5-FU and valdecoxib may decrease tumor volume by 74%.

Example 6

In Vitro Inhibition of EGFR Kinase Activity

The in vitro activity of the combinations described herein in inhibiting the receptor tyrosine kinase may be determined by the following procedure. The activity of the combinations of the present disclosure, in vitro, can be determined by the amount of inhibition of the phosphorylation of an exogenous substrate (e.g., $Lys_3$—Gastrin or polyGluTyr (4:1) random copolymer (Posner et al., *J. Biol. Chem.*, 1992, 267 (29), 20638-472)) on tyrosine by epidermal growth factor receptor kinase by a test compound relative to a control. Affinity purified, soluble human EGF receptor (96 ng) is obtained according to the procedure in G. N. Gill, W. Weber, *Methods in Enzymology*, 1987, 146, 82-8 from A431 cells (American Type Culture Collection, Rockville, Md.) and preincubated in a microfuge tube with EGF (2 µg/ml) in phosphorylation buffer+vanadate (PBV: 50 mM HEPES, pH 7.4; 125 mM NaCl; 24 mM $MgCl_2$; 100 µM sodium orthovanadate), in a total volume of 10 µl, for 20-30 minutes at room temperature. The composition comprising a combination of 2-(4-ethoxyphenyl)-4-methyl-1-(4-sulfamoylphenyl)-pyrrole with erlotinib, dissolved in dimethylsulfoxide (DMSO), is diluted in PBV, and 10 µl is mixed with the EGF receptor/EGF mix, and incubated for 10-30 minutes at 30° C. The phosphorylation reaction is initiated by addition of 20 µl $^{33}$P-ATP/substrate mix (120 µM $Lys_3$-Gastrin (sequence in single letter code for amino acids, KKKGPWLEEEEEAYGWLDF), 50 mM Hepes pH 7.4, 40 µM ATP, 2 pCi .gamma.-[$^{33}$P]-ATP) to the EGFr/EGF mix and incubated for 20 minutes at room temperature. The reaction is stopped by addition of 10 µl stop solution (0.5 M EDTA, pH 8; 2 mM ATP) and 6 µl 2N HCl. The tubes are centrifuged at 14,000 RPM, 4° C., for 10 minutes. 35 µl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., $lys_3$-gastrin) is subtracted from all values as a background and percent inhibition is calculated relative to controls without the composition present. Such assays, carried out with a range of doses of test combinations, allow the determination of an approximate $IC_{50}$ value for the in vitro inhibition of EGFR kinase activity. Other methods for determining the activity of the combinations presented herein are described in U.S. Pat. No. 5,747,498, the disclosure of which is incorporated herein.

Example 7

Pharmaceutical Compositions and Dosage Forms

Dosage formulations comprising pharmaceutical excipients and carriers and a pharmaceutical composition comprising a combination of erlotinib (A) and 2-(4-ethoxyphenyl)-4-methyl-1-(4-sulfamoylphenyl)-pyrrole (B) include:

| Combination | Amount of A per tablet (mg) | Amount of B per tablet (mg) |
| --- | --- | --- |
| A/B | 25 | 1, 5, 10, 25, 50, 100, 200, 300, 400, 600, 800, 1000, 1200 |
| A/B | 100 | 1, 5, 10, 25, 50, 100, 200, 300, 400, 600, 800, 1000, 1200 |
| A/B | 150 | 1, 5, 10, 25, 50, 100, 200, 300, 400, 600, 800, 1000, 1200 |
| A/B | 200 | 1, 5, 10, 25, 50, 100, 200, 300, 400, 600, 800, 1000, 1200 |
| A/B | 300 | 1, 5, 10, 25, 50, 100, 200, 300, 400, 600, 800, 1000, 1200 |
| A/B | 450 | 1, 5, 10, 25, 50, 100, 200, 300, 400, 600, 800, 1000, 1200 |

Dosage formulations described herein, including the formulations set forth in the above table, may be administered in a single fixed dose comprising a combination of 2-(4-ethoxyphenyl)-4-methyl-1-(4-sulfamoylphenyl)-pyrrole and erlotinib or as a separate administration of a single dose of 2-(4-ethoxyphenyl)-4-methyl-1-(4-sulfamoylphenyl)-pyrrole and a single dose of erlotinib.

Example 8

Biological Evaluation

Figure 3:
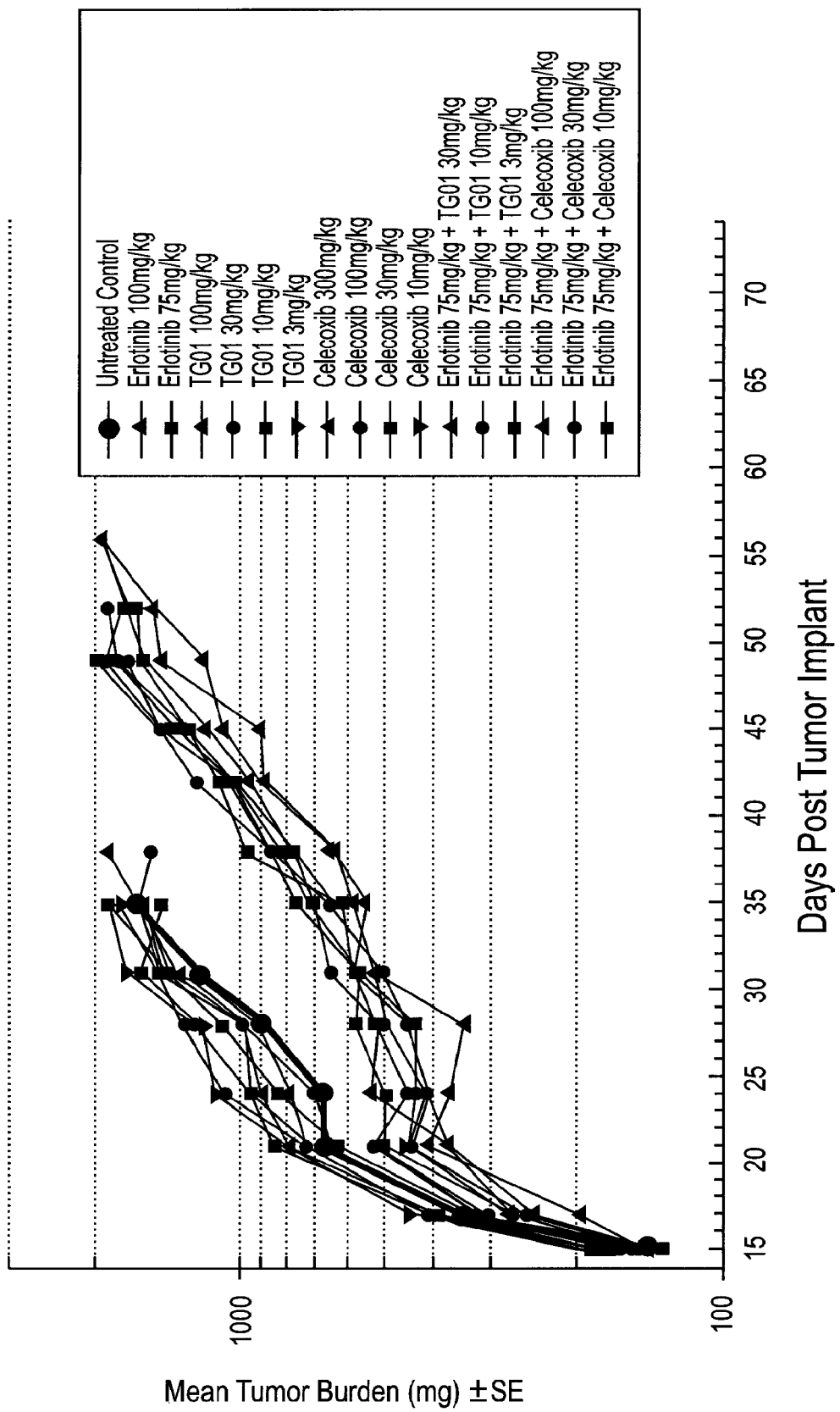
FIG. 3 provides a graph illustrating the results of a A431 squamous vulvar carcinoma xenograft study.

COX-2 Selective Inhibitors
A431 Squamous Vulvar Carcinoma Model
Mice are injected subcutaneously in the left paw ($1 \times 10^6$ tumor cells suspended in 30% Matrigel) and tumor volume is evaluated using a phlethysmometer twice a week for 30-60 days. Implantation of squamous vulvar carcinoma (A431) into nude mice produces tumors that reach 0.6-2 ml between 30-50 days. Blood is drawn twice during the experiment in a 24 h protocol to assess plasma concentration and total exposure by AUC analysis. The data is expressed as the mean +/−SEM. Student's and Mann-Whitney tests are used to assess differences between means using the InStat software package.
Mice injected with A431 cancer cells are treated with a composition comprising one of the following: 1. erlotinib (75 or 100 mg/kg); 2. 2-(4-ethoxyphenyl)-4-methyl-1-(4-sulfamoylphenyl)-pyrrole (3, 10, 30, or 100 mg/kg); 3. celecoxib (10, 30, 100, or 300 mg/kg); 4. erlotinib (75 mg/kg) and 2-(4-ethoxyphenyl)-4-methyl-1-(4-sulfamoylphenyl)-pyrrole (3, 10, or mg/kg); 4. erlotinib (75 mg/kg) and celecoxib (10, 30, or 100 mg/kg). The efficacy is determined by measuring tumor volume. The results from these studies, shown in FIG. 3, demonstrate that a composition comprising a combination of 2-(4-ethoxyphenyl)-4-methyl-1-(4-sulfamoylphenyl)-pyrrole with erlotinib administered to tumor bearing mice delayed the growth of tumors by 55% compared to erlotinib alone. The combination of erlotinib and celecoxib demonstrated a tumor growth delay of only 36%.

Example 9

Study of 2-(4-ethoxyphenyl)-4-methyl-1-(4-sulfamoylphenyl)-pyrrole in Combination with Erlotinib in Metastatic or Recurrent Non-Small Cell Lung Cancer (NSCLC) Patients Methods: Subjects with recurrent or metastatic NSCLC were treated with erlotinib (150 mg/day PO) and escalating doses of 2-(4-ethoxyphenyl)-4-methyl-1-(4-sulfamoylphenyl)-pyrrole (100-1200 mg/day PO). Pharmacokinetics for 2-(4-ethoxyphenyl)-4-methyl-1-(4-sulfamoylphenyl)-pyrrole and erlotinib were evaluated.

Results: Nineteen subjects were treated: 3 at 2-(4-ethoxyphenyl)-4-methyl-1-(4-sulfamoylphenyl)-pyrrole 100 mg; 4 at 2-(4-ethoxyphenyl)-4-methyl-1-(4-sulfamoylphenyl)-pyrrole 200 mg; 12 at 2-(4-ethoxyphenyl)-4-methyl-1-(4-sulfamoylphenyl)-pyrrole 400 mg. The optimal biologic dose selected was 400 mg. 2-(4-ethoxyphenyl)-4-methyl-1-(4-sulfamoylphenyl)-pyrrole pharmacokinetics reveal a median $T_{max}$ of 2 hours (range 1.54), mean (SD) T1/2 of 11.8 (5.3) hours, Cmax of 313.0 (99.6) ng/ml and AUC (0-t) of 2816 (1204) ng h/ml. The results show that 2-(4-ethoxyphenyl)-4-methyl-1-(4-sulfamoylphenyl)-pyrrole and erlotinib have been safely administered in this study.

Example 10

Study of 2-(4-ethoxyphenyl)-4-methyl-1-(4-sulfamoylphenyl)-pyrrole in Combination with Erlotinib in Metastatic or Recurrent Non-Small Cell Lung Cancer (NSCLC) Patients This study compares the anti-tumor efficacy of 2-(4-ethoxyphenyl)-4-methyl-1-(4-sulfamoylphenyl)-pyrrole and erlotinib with placebo and erlotinib as measured by time to disease progression. The experimental arm consists of 400 mg/day 2-(4-ethoxyphenyl)-4-methyl-1-(4-sulfamoylphenyl)-pyrrole, in combination with 150 mg/day erlotinib. The placebo arm consists of 400 mg/day placebo tablets, in combination with 150 mg/day erlotinib.

Example 11

Study of 2-(4-ethoxyphenyl)-4-methyl-1-(4-sulfamoylphenyl)-pyrrole in Combination with Erlotinib and Gemcitabine in Advanced Pancreatic Cancer Patients This study compares the anti-tumor efficacy of 2-(4-ethoxyphenyl)-4-methyl-1-(4-sulfamoylphenyl)-pyrrole and erlotinib/gemcitabine with placebo and erlotinib/gemcitabine as measured by time to disease progression. The experimental arm will consist of 400 mg/day 2-(4-ethoxyphenyl)-4-methyl-1-(4-sulfamoylphenyl)-pyrrole, in combination with 100 mg/day erlotinib, and gemcitabine administered as an intravenous infusion of a 1000 mg/m² dose over 30 minutes once a week for up to 7 weeks followed by one week of rest and then subsequent cycles of weekly infusions for 3 weeks of a 4 week cycle. The placebo arm consists of 400 mg/day placebo tablets, in combination with 100 mg/day erlotinib, and gemcitabine administered as an intravenous infusion of a 1000 mg/m² dose over 30 minutes once a week for up to 7 weeks followed by one week of rest and then subsequent cycles of weekly infusions for 3 weeks of a 4 week cycle.

Example 12

Treatment of Non-Small Cell Lung Cancer

A method for treating a subject having non-small cell lung cancer comprising administering to the subject a therapeutically effective amount of a combination comprising 2-(4-ethoxyphenyl)-4-methyl 1-(4-sulfamoylphenyl)-pyrrole and erlotinib or their respective pharmaceutically acceptable salt, solvate or prodrug is contemplated. The subject is treated using a single dosage form of a combination of 2-(4-ethoxyphenyl)-4-methyl 1-(4-sulfamoylphenyl)-pyrrole in about 100, about 200, about 300, about 400, about 600, about 800, and about 1000 and about 1200 mg aliquots and erlotinib in about a 150 mg aliquot. The treatment of the subject using a separate administration of 2-(4-ethoxyphenyl)-4-methyl 1-(4-sulfamoylphenyl)-pyrrole in about 200, about 400, and about 800 mg aliquots and erlotinib in about a 150 mg aliquot is also contemplated. The maximum tolerated dose of this combination will be an endpoint for this study.

Example 13

Treatment of Breast Cancer

A method for treating a subject having breast cancer comprising administering to the subject a therapeutically effective amount of a combination comprising 2-(4-ethoxyphenyl)-4-methyl 1-(4-sulfamoylphenyl)-pyrrole and erlotinib or their respective pharmaceutically acceptable salt, solvate or prodrug is contemplated. Combined treatment with erlotinib and 2-(4-ethoxyphenyl)-4-methyl 1-(4-sulfamoylphenyl)-pyrrole is expected to achieve increased tumor inhibition compared with erlotinib administered as a single agent.

Example 14

Treatment of Colorectal Cancer

A method for treating a subject having colorectal cancer comprising administering to the subject a therapeutically effective amount of a combination comprising 2-(4-ethoxyphenyl)-4-methyl 1-(4-sulfamoylphenyl)-pyrrole and erlotinib or their respective pharmaceutically acceptable salt, solvate or prodrug is contemplated. Combined treatment with erlotinib and 2-(4-ethoxyphenyl)-4-methyl 1-(4-sulfamoylphenyl)-pyrrole are expected to achieve significantly increased tumor inhibition compared with either 2-(4-ethoxyphenyl)-4-methyl 1-(4-sulfamoylphenyl)-pyrrole or erlotinib administered as single agents.

Example 15

Treatment of Glioma

A method for treating a subject having glioma comprising administering to the subject a therapeutically effective amount of a combination comprising 2-(4-ethoxyphenyl)-4-methyl 1-(4-sulfamoylphenyl)-pyrrole and erlotinib or their respective pharmaceutically acceptable salt, solvate or prodrug is contemplated. The subject is treated using a single dosage form of a combination of 2-(4-ethoxyphenyl)-4-methyl 1-(4-sulfamoylphenyl)-pyrrole in about 1, about 5, about 10, about 25, about 50, about 100, about 200, about 300, about 400, about 600, about 800, about 1000, and about 1200 mg aliquots and erlotinib in about a 25 mg aliquot. The treatment of the subject using a separate administration of 2-(4-ethoxyphenyl)-4-methyl 1-(4-sulfamoylphenyl)-pyrrole in about 1, about 5, about 10, about 25, about 50, about 100, about 200, about 300, about 400, about 600, about 800, about 1000, and about 1200 mg aliquots and erlotinib in about 100, 150, 200, 300, or 450 mg aliquot is also contemplated. The treatment will also be administered in subjects with $2^{nd}$ temozolomide failures.

Example 16

Treatment of Head and Neck Cancer

A method for treating a subject having head and neck cancer comprising administering to the subject a therapeutically effective amount of a combination comprising 2-(4-ethoxyphenyl)-4-methyl 1-(4-sulfamoylphenyl)-pyrrole and erlotinib or their respective pharmaceutically acceptable salt, solvate or prodrug is contemplated. The subject is treated using a single dosage form of a combination of 2-(4-ethoxyphenyl)-4-methyl 1-(4-sulfamoylphenyl)-pyrrole in about 1, about 5, about 10, about 25, about 50, about 100, about 200, about 300, about 400, about 600, about 800, about 1000, and about 1200 mg aliquots and erlotinib in about a 25 mg aliquot. The treatment of the subject using a separate administration of 2-(4-ethoxyphenyl)-4-methyl 1-(4-sulfamoylphenyl)-pyrrole in about 1, about 5, about 10, about 25, about 50, about 100, about 200, about 300, about 400, about 600, about 800, about 1000, and about 1200 mg aliquots and erlotinib in about 100, 150, 200, 300, or 450 mg aliquot is also contemplated. The treatment will also be administered in conjunction with one or one or more chemotherapy agents (e.g., paclitaxel [Taxol®], docetaxel [Taxotere®], gemcitabine [Gemzar®], doxorubicin [Doxil®]) which may be further combined with established chemotherapeutic agents (e.g., methotrexate [Trexall®, Methotrex®]). In another embodiment, therapy for the treatment of head and neck cancer according to the invention utilizes a combination of therapeutically effective amount of a composition comprising a combination of 2-(4-ethoxyphenyl)-4-methyl 1-(4-sulfamoylphenyl)-pyrrole and erlotinib and Erbitux®.

What is claimed is:

1. A method for treating a subject having non-small cell lung cancer, comprising administering to the subject, a therapeutically effective amount of a combination of active agents consisting of a 1,2-diphenylpyrrole derivative and an EGFR inhibitor or their respective pharmaceutically acceptable salt, wherein the pyrrole derivative is 2-(4-ethoxyphenyl)-4-methyl-1-(4-sulfamoylphenyl)-pyrrole and the EGFR inhibitor is erlotinib.

2. The method of claim 1 wherein the 1,2-diphenylpyrrole derivative and the EGFR inhibitor are administered sequentially in either order or simultaneously.

3. The method of claim 1 wherein the 1,2-diphenylpyrrole derivative is administered first.

4. The method of claim 1 wherein the EGFR inhibitor is administered first.

5. The method of claim 1 wherein administering the combination enhances treatment of the subject.

6. The method of claim 1 wherein administering the combination reduces the side effects of the treatment of cancer compared to a treatment of the EGFR inhibitor alone or a treatment of the 1,2-diphenylpyrrole derivative alone.

7. The method of claim 1 wherein administering the combination is through oral, parenteral, buccal, intranasal, epidural, sublingual, pulmonary, local, rectal, or transdermal administration.

8. The method of claim 7 wherein administering the combination is through parenteral administration.

9. The method of claim 8 wherein parenteral administration is intravenous, subcutaneous, intrathecal, or intramuscular.

10. The method of claim 7 wherein oral administration is in a single dosage form.

11. The method of claim 10 wherein the single dosage form enhances patient compliance and/or reduces pill burden.

12. The method of claim 10 wherein the single dosage form is a single capsule or a single tablet.

13. The method of claim 12 wherein the single dosage form is a single tablet.

14. The method of claim 13 wherein the single tablet comprises from about 1 mg to about 1200 mg of 2-(4-ethoxyphenyl)-4-methyl-1-(4-sulfamoylphenyl)-pyrrole and from about 25 mg to about 450 mg of erlotinib.

15. The method of claim 14 wherein the single tablet comprises from about 1 mg to about 1200 mg 2-(4-ethoxyphenyl)-4-methyl-1-(4-sulfamoylphenyl)-pyrrole and about 25 mg of erlotinib.

16. The method of claim 14 wherein the single tablet comprises from about 1 mg to about 1200 mg 2-(4-ethoxyphenyl)-4-methyl-1-(4-sulfamoylphenyl)-pyrrole and about 100 mg of erlotinib.

17. The method of claim 14 wherein the single tablet comprises from about 1 mg to about 1200 mg 2-(4-ethoxyphenyl)-4-methyl-1-(4-sulfamoylphenyl)-pyrrole and about 150 mg of erlotinib.

18. The method of claim 14 wherein the single tablet comprises from about 1 mg to about 1200 mg 2-(4-ethoxyphenyl)-4-methyl-1-(4-sulfamoylphenyl)-pyrrole and about 200 mg of erlotinib.

19. The method of claim 14 wherein the single tablet comprises from about 1 mg to about 1200 mg 2-(4-ethoxyphenyl)-4-methyl-1-(4-sulfamoylphenyl)-pyrrole and about 300 mg of erlotinib.

20. The method of claim 14 wherein the single tablet comprises from about 1 mg to about 1200 mg 2-(4-ethoxyphenyl)-4-methyl-1-(4-sulfamoylphenyl)-pyrrole and about 450 mg of erlotinib.

21. A method for treating a subject having non-small cell lung cancer, comprising administering to the subject, a therapeutically effective amount of a combination of active agents consisting of 2-(4-ethoxyphenyl)-4-methyl-1-(4-sulfamoylphenyl)-pyrrole, erlotinib and gemcitabine, or their respective pharmaceutically acceptable salt.

22. The method of claim 21 wherein the 2-(4-ethoxyphenyl)-4-methyl-1-(4-sulfamoylphenyl)-pyrrole is administered at a dose of 100-1200 mg per day, the erlotinib is administered at a dose of 50-250 mg per day, and the gemcitabine is administered at a dose of 500-1500 mg per meter squared of body surface area per weekly intravenous administration.

23. The method of claim 22 wherein the 2-(4-ethoxyphenyl)-4-methyl-1-(4-sulfamoylphenyl)-pyrrole is administered at a dose of 400 mg per day, the erlotinib is administered at a dose of 100 mg per day, and the gemcitabine is administered at a dose of 1000 mg per meter squared of body surface area per weekly intravenous administration.

24. The method of claim 22 wherein the 2-(4-ethoxyphenyl)-4-methyl-1-(4-sulfamoylphenyl)-pyrrole is administered at a dose of 400 mg per day, the erlotinib is administered at a dose of 150 mg per day, and the gemcitabine is administered at a dose of 1000 mg per meter squared of body surface area per weekly intravenous administration.

* * * * *